US009540322B2

(12) United States Patent
Jorgensen et al.

(10) Patent No.: US 9,540,322 B2
(45) Date of Patent: Jan. 10, 2017

(54) MIF MODULATORS

(75) Inventors: William L. Jorgensen, Deep River, CT (US); Richard J. Bucala, Cos Cob, CT (US)

(73) Assignee: Yale University, New Haven, CT (US)

( * ) Notice: Subject to any disclaimer, the term of this patent is extended or adjusted under 35 U.S.C. 154(b) by 1192 days.

(21) Appl. No.: 13/100,922

(22) Filed: May 4, 2011

(65) Prior Publication Data
US 2012/0004261 A1 Jan. 5, 2012

Related U.S. Application Data

(63) Continuation-in-part of application No. 12/773,430, filed on May 4, 2010, which is a continuation-in-part of application No. PCT/US2009/004704, filed on Aug. 18, 2009.

(60) Provisional application No. 61/189,327, filed on Aug. 18, 2008.

(51) Int. Cl.
| C07D 249/06 | (2006.01) |
| C07D 413/04 | (2006.01) |
| C07D 417/04 | (2006.01) |
| C07D 209/18 | (2006.01) |
| C07D 235/12 | (2006.01) |
| C07D 235/24 | (2006.01) |
| C07D 263/58 | (2006.01) |
| C07D 275/04 | (2006.01) |
| C07D 307/80 | (2006.01) |
| C07D 307/83 | (2006.01) |
| C07D 401/04 | (2006.01) |
| C07D 401/06 | (2006.01) |
| C07D 403/04 | (2006.01) |
| C07D 405/06 | (2006.01) |

(52) U.S. Cl.
CPC .......... *C07D 209/18* (2013.01); *C07D 235/12* (2013.01); *C07D 235/24* (2013.01); *C07D 249/06* (2013.01); *C07D 263/58* (2013.01); *C07D 275/04* (2013.01); *C07D 307/80* (2013.01); *C07D 307/83* (2013.01); *C07D 401/04* (2013.01); *C07D 401/06* (2013.01); *C07D 403/04* (2013.01); *C07D 405/06* (2013.01); *C07D 413/04* (2013.01); *C07D 417/04* (2013.01)

(58) Field of Classification Search
CPC .... C07D 249/06; C07D 413/04; C07D 417/04
USPC .......................................... 514/359; 548/255
See application file for complete search history.

(56) References Cited

U.S. PATENT DOCUMENTS

| 3,846,491 A | 11/1974 | Shindarov et al. |
| 6,774,227 B1 | 8/2004 | Bucala et al. |
| 8,071,593 B2 | 12/2011 | Schadt et al. |
| 2003/0166658 A1 | 9/2003 | Hofmann et al. |
| 2003/0195194 A1 | 10/2003 | Gaeta et al. |
| 2004/0132786 A1 | 7/2004 | Chyba et al. |
| 2005/0032786 A1 | 2/2005 | Kajino et al. |
| 2006/0194801 A1 | 8/2006 | Kelly |
| 2007/0219189 A1 | 9/2007 | Billich et al. |
| 2007/0281924 A1 | 12/2007 | Gaeta |
| 2008/0317744 A1 | 12/2008 | Boyce et al. |
| 2009/0163545 A1 | 6/2009 | Goldfarb |
| 2009/0270326 A1 | 10/2009 | Kimura |
| 2010/0267714 A1 | 10/2010 | Jorgensen et al. |
| 2012/0040974 A1 | 2/2012 | Jorgensen et al. |

FOREIGN PATENT DOCUMENTS

| CA | 1019749 | 10/1977 |
| DE | 111 637 | 3/1975 |
| EP | 0 200 345 | 3/1986 |
| EP | 0 768 305 | 4/1997 |
| EP | 1 074 257 | 2/2001 |
| EP | 1 125 936 | 8/2001 |
| EP | 1 316 550 | 11/2002 |
| EP | 1 555 267 | 7/2005 |
| FR | 2 150 833 | 4/1973 |
| FR | 2 244 506 | 4/1975 |
| KR | 10-2007-0072598 | 7/2007 |
| WO | WO 97/38665 | 10/1997 |
| WO | WO 97/43239 | 11/1997 |
| WO | WO 01/97979 | 4/2001 |
| WO | WO 01/94340 | 12/2001 |
| WO | WO 02/06246 | 1/2002 |
| WO | WO 02/07720 | 1/2002 |
| WO | WO 02/14315 | 2/2002 |
| WO | WO 02/051819 | 7/2002 |
| WO | WO 02/062290 | 8/2002 |
| WO | WO 02/074763 | 9/2002 |
| WO | WO 02/094203 | 11/2002 |
| WO | WO 02/100332 | 12/2002 |
| WO | WO 03/020719 | 3/2003 |
| WO | WO 03/072553 | 9/2003 |
| WO | WO 03/104178 | 12/2003 |
| WO | WO 03/104203 | 12/2003 |

(Continued)

OTHER PUBLICATIONS

Livi, "Ester, amide and ether derivatives of 1-( -phenyl-substituted)-1,2,3-triazoles", Journal of Heterocyclic Chemistry, 20, 1983, pp. 1729-1733.*
Biagi, "N-Benzyl-4-phenyl-1,2,3-triazole derivatives as in vitro inhibitors of the prostaglandin synthesis", Farmaco, Edizione Scientifica (1986), 41(8), pp. 597-610.*
Andersen, "Efficient one-pot synthesis of 1-aryl 1,2,3-triazoles from aryl halides and terminal alkynes in the presence of sodium azide", Synlett (2005), (19), 2941-2947.*
Dong, "Syntheses of some new 1-aryl-4,5-substituted-1,2,3-triazoles", Indian Journal of Heterocyclic Chemistry (2006), 15(4), 415-416.*

(Continued)

*Primary Examiner* — Sahar Javanmard
(74) *Attorney, Agent, or Firm* — Fish & Richardson P.C.

(57) ABSTRACT

The invention provides novel heterocyclic compounds, pharmaceutical compositions and methods of treatment that modulate levels of MIF expression and treat disorders associated with high or low levels of MIF expression.

29 Claims, No Drawings

(56) References Cited

FOREIGN PATENT DOCUMENTS

| | | |
|---|---|---|
| WO | WO 2004/037829 | 5/2004 |
| WO | WO 2004/089927 | 10/2004 |
| WO | WO 2005/021546 | 3/2005 |
| WO | WO 2005/033104 | 4/2005 |
| WO | WO 2005/094338 | 10/2005 |
| WO | WO 2006/019831 | 2/2006 |
| WO | WO 2006/045505 | 5/2006 |
| WO | WO 2006/049835 | 5/2006 |
| WO | WO 2006/066133 | 6/2006 |
| WO | WO 2006/090169 | 8/2006 |
| WO | WO 2006/122011 | 11/2006 |
| WO | WO 2006/129164 | 12/2006 |
| WO | WO 2007/070961 | 6/2007 |
| WO | WO 2007/076161 | 7/2007 |
| WO | WO 2007/084391 | 7/2007 |
| WO | WO 2007/093827 | 8/2007 |
| WO | WO 2007/103550 | 9/2007 |
| WO | WO 2007/140263 | 12/2007 |
| WO | WO 2008/013622 | 1/2008 |
| WO | WO 2008/035823 | 3/2008 |
| WO | WO 2008/045905 | 4/2008 |
| WO | WO 2008/148449 | 12/2008 |
| WO | WO 2009/055514 | 4/2009 |
| WO | WO 2009/094445 | 7/2009 |
| WO | WO 2009/108720 | 9/2009 |
| WO | WO 2010/021693 | 2/2010 |
| WO | WO 2011/140202 | 11/2011 |

OTHER PUBLICATIONS

Aidouni et al., "Microwave-Assisted Synthesis of N-Heterocyclic Carbene Precursors," Synlett, 3:493-495, (2006).
Alouane et al., "Remarkably Efficient Charcoal-Promoted Ring-Closing Carbonylations," Synthesis, 860-864, (2006).
Barreca et al., "Computational Strategies in Discovering Novel Non-nucleoside Inhibitors of HIV-1 RT", Journal of Medicinal Chemistry, vol. 48, 2005, pp. 3433-3437.
Bernhagen et al., "Purification, Bioactivity, and Secondary Structure Analysis of Mouse and Human Macrophage Migration Inhibitory Factor (MIF)," Biochemistry, 33:14144-14155, (1994).
Bernhagen et al., "MIF is a Pituitary-derived cytokine that potentiates lethal endotoxaemia ," Nature, 365:756-759, (1993).
Bose et al., "Synthesis of 2-Arylbenzothiazoles by DDQ-Promoted Cyclization of Thioformanilides: A Solution-Phase Strategy for Library Synthesis," Synthesis, 819-823, (2007).
Bravo et al., "Antimicrobial Activity of Natural 2-Benzoxazolinones and Related Derivatives", Journal of Agricultural and Food Chemistry, vol. 45, No. 8, pp. 3255-3257, 1997.
Cheng and Al-Abed, "Critical modifications of the ISO-1 scaffold improve its potent inhibition of macrophage migration inhibitory factor (MIF) tautomerase activity," Bioorg. Med. Chem. Left., 2006, 16:3376-3379.
Cook and Martin, "Remington's Practice of Pharmacy, a Treatise," The Mack Publishing Company, title page, table of contents and subject index (104 pgs), (1951).
Deng et al.,"Reaction of N-Monosubstituted Hydrazones with Nitroolefins: A Novel Regioselective Pyrazole Synthesis," Org. Lett., 2006, 8, 3505-3508.
Dios et al., "Inhibition of MIF Bioactivity by Rational Design of Pharmacological Inhibitors of MIF Tautomerase Activity," J. Med. Chem., 45:2410-2416, (2002).
Erol et al., "Synthesis of ethanone derivatives of 2-benzoxazolinones and their antimicrobial activities", Arzneimittel-Forschung, vol. 46, No. 2, pp. 205-206, 1996.
Escobar et al., "Evaluation of DIMBOA analogs as antifeedants and antibiotics towards the aphid Sitobion avenae in artificial diets", Journal of Chemical Ecology, vol. 25, No. 7, pp. 1543-1554, 1999.
Gershon et al., "Reexamination of the thermolytic rearrangement of 4-halophenyl azides to 2-aminophenols and other products", Monatshefte Fuer Chemie, vol. 124, No. 4, pp. 367-376, 1993.

Itoh et al., "Introduction of a Hydroxy Group at the Para Position and N-Iodophenylation of N-Arylamides Using Phenyliodine (III) Bis(Trifluoroacetate)," J. Org. Chem., 67:7424-7428, (2002).
Jorgensen, "The Many Roles of Computation in Drug Discovery," Science, 2004, 303:1813-1818.
Jorgensen, "Efficient Drug Lead Discovery and Optimization," Accounts of Chemical Research, vol. 42, No. 6, pp. 724-733, Jun. 2009.
Kim et al., "KSP Inhibitor ARRY-520 as a Substitute for Paclitaxel in Type I Ovarian Cancer Cells," J. Transl Med., 2009, 7:63.
Korhonen et al., "Predictive Three-Dimensional Quantitative Structure-Activity Relationship of Cytochrome P450 1A2 Inhibitors", Journal of Medicinal Chemistry, vol. 48, No. 11, pp. 3808-3815, 2005.
Lee, H., "Isoindol-1, 3-dione and isoindol-1-onederivatives with high binding affinity to β-amyloaid fibrils," Bioorganic & Medicinal Chemistry Letters, vol. 18, Issue 5, Mar. 1, 2008, pp. 1628-1631.
Leng et al., "MIF signal transduction initiated by binding to CD74.3," Exp. Med., 2003, 197:1467-1476.
Liégault et al., "Intramolecular Pd(II)-Catalyzed Oxidative Biaryl Synthesis Under Air: Reaction Development and Scope," J. Org. Chem., 73, 5022-5028 (2008).
Lipshutz et al.,"Heterogeneous Copper-in-Charcoal-Catalyzed Click Chemistry," Angew. Chem. Int. Ed., 2006, 45, 8235-8238.
Liu et al., "Assembly of Conjugated Enynes and Substituted Indoles via CuI-Amino Acid-Catalyzed Coupling of 1-Alkynes with Vinyl Iodides and 2-Bromotrifluoroacetanilides," J. Org. Chem., 72, 4844-4850 (2007).
Liu et al., "Synthesis of Indazoles by the [3+2] Cycloaddition of Diazo Compounds with Arynes and Subsequent Acyl Migration," J. Org. Chem., 73, 219-226 (2008).
Lolis and Bucala, "Crystal structure of macrophage migration inhibitory factor (MIF), a glucocorticoid-induced regulator of cytokine production, reveals a unique architecture," Proc. Assoc. Amer. Physicians, 1996, 108:415-9.
Lolis and Bucala, "Macrophage migration inhibitory factor," Expert Opin. Therap. Targets, 2003, 7:153-164.
Lubetsky et al., "Pro-1 of macrophage migration inhibitory factor functions as a catalytic base in the phenylpymvate tautomerase activity," Biochemistry, 1999, 38, 7346-54.
Lubetsky et al., "The tautomerase active site of macrophage migration inhibitory factor is a potential target for discovery of novel anti-inflammatory agents 3," Biol. Chem., 2002, 277:24976-24982.
Luvino, D. et al., "Sequential Seyferth-Gilbert/CuAAC Reactions: Application to the One-Pot Synthesis of Triazoles from Aldehydes," Synlett, 2007, 3037-3041.
Martyniuk et al., "Effects of Some Benzoxazinoids on in Vitro Growth of Cephalosporium Gramineum and Other Fungi Pathogenic to Cereals and on Cephalosporium Stripe of Winter Weat", Journal of Agricultural and Food Chemistry, vol. 54, No. 4, pp. 1036-1039, 2006.
Mesangeau et al., "Conversion of a Highly Selective Sigma-1 Receptor-Ligand to Sigma-2 Receptor Preferring Ligands with Anticocaine Activity", Journal of Medicinal Chemistry, vol. 51, No. 5, pp. 1482-1486, 2008.
Minakata et al., "Practical and Convenient Synthesis of N-Heterocycles: Stereoselective Cyclization of N-Alkenylamides with t-BuO1 under Neutral Conditions," Org. Lett., 2006, 8, 3335-3337.
Morand et al., "MIF: a new cytokine link between rheumatoid arthritis and atherosclerosis," Nature Rev. Drug Disc., 2006, 5, 399-411.
Nerenberg et al., "Design and synthesis of N-alkylated saccharins as selective α-1A adrenergic receptor antagonists", Bioorganic & Medicinal Chemistry Letters, vol. 8, No. 18, pp. 2467-2472, 1998.
Orita et al., "Coumarin and Chromen-4-one Analogues as Tautomerase Inhibitors of Macrophage Migration Inhibitory Factor: Discovery and X-ray Crystallography," J. Med. Chem. 2001, 44:540-547.
Orita et al., "Macrophage migration inhibitory factor and the discovery of tautomerase inhibitors," Curr. Pharm. Res., 2002, 8:1297-1317.

(56) References Cited

OTHER PUBLICATIONS

Park et al.,"Heterogeneous Copper Catalyt for the Cycloaddition of Azides and Alkynes without Additives under Ambient Conditions," Org. Lett., 2008, 10, 497-500.

Pirrung et al., "Mechanistic and stereochemical study ofphenylpyruvate tautomerase," J. Am. Chem. Soc., 1993, 115:7103-10.

Rosengren et al., "The immunoregulatory mediator macrophage migration inhibitory factor (MIF) catalyzes a tautomerization reaction," Molec. Med., 1996, 2:143-149.

Rosengren et al., "The macrophage migration inhibitory factor MIF is a phenylpyruvate tautomerase," FEBS Lett., 1997, 17:85-8.

Ryabukhin et al., "Synthesis of Fused Imidazoles and Benzothiazoles from (Hetero) Aromatic ortho-Diamines or ortho-Aminothiophenol and Aldehydes Promoted by Chlorotrimethylsilane," Synthesis, 3715-3726 (2006).

Sakai et al., InBr3-Promoted Divergent Approach to Polysubstituted Indoles and Quinolines from 2-Ethynylanilines: Switch from an Intramoledulcar Cyclization to an Intermolecular Dimerization by a Type of Terminal Substituent Group, J. Org. Chem., 73, 4160-4165 (2008).

Seijas J. A., et al.,"Lawesson's Reagent and Microwaves: A New Efficient Access to Benzoxazoles and Benzothiazoles from Carboxylic Acids under Solvent-Free Conditions," Synlett, 313-316 (2007).

Senter et al., "Inhibition of macrophage migration inhibitory factor (MIF) tautomerase and biological activities by acetaminophen metabolites," Proc. Nat. Acad. Sci. USA, 2002, 99:144-9.

Shankaran et al, "Inhibition of nitric oxide synthase by benzoxazolones", Bioorganic & Medicinal Chemistry Letters, vol. 7, No. 22, pp. 2887-2892, 1997.

Sheng et al., One-Pot Synthesis of 3-Substituted Isoxazoles from Phenyl Vinylic Selenide, Synthesis, 2003, 2763-2764.

Stamps et al., "Mechanism of the Phenylpymvate Tautomerase Activity of Macrophage Migration Inhibitory Factor: Properties of the P1G, P1A, Y95F, and N97A Mutants," Biochemistry, 2000, 39:9671-9678.

Sun et al., Crystal structure at 2.6-A resolution of human macrophage migration inhibitory factor. Proc. Nat. Acad. Sci. USA, 1996, 93:5191-5196.

Ucar et al., "'Fries Like' Rearrangement: a novel and efficient method for the synthesis of 6-acyl-2(3H)-benzoxazolones and 6-acyl-2(3H)-benzothiazolones", Tetrahedron, vol. 54, No. 9, pp. 1763-1772, 1998.

Ucar et al., "Synthesis and Anticonvulsant Activity of 2(3H)-Benzoxazolone and 2(3H)-Benzothiazolone Derivatives," J. Med. Chem. 1998, 41, pp. 1138-1145.

Varma et al., "Synthesis and antibacterial activity of certain 3-substituted benzoxazolinones", Journal of Pharmaceutical Sciences, vol. 57, No. 1, 39-44, 1968.

Virre et al.,"Copper-Catalyzed Domino Annulation Approaches to the Synthesis of Benzoxazoles under Microwave-Accelerated and Conventional Thermal Conditions," J. Org. Chem., 73, 3452-3459 (2008).

Weiss and Goodnought, "Anemia of Chronic Disease", N. Engl. J. Med., 352(10): 1011-23 (2005).

Zhang and Bucala, "Inhibition of macrophage migration inhibitory factor (MIF) tautomerase activity by dopachrome analogs," Bioorg. Med. Chem. Lett., 1999, 9:3193-3198.

Zhu et al., "Discovery and SAR of oxinodole-pyridine-based protein kinase B/Akt inhibitors for treating cancers", Bioorganic & Medicinal Chemistry Letters, vol. 16, No. 13, pp. 3424-3429, 2006.

International Preliminary Report on Patentability dated Feb. 22, 2011 for International Appln. No. PCT/US2009/004704 (4 pgs.).

International Preliminary Report on Patentability and Written Opinion dated Nov. 6, 2012 for International Appln. No. PCT/US2011/035161, 8 pgs.

International Search Report dated Apr. 26, 2010 for International Appln. No. PCT/US2009/004704 (3 pgs.).

International Search Report and Written Opinion dated Sep. 3, 2012 for International Appln. No. PCT/US2011/035161 (11 pgs).

Supplementary European Search Report dated Feb. 10, 2012 for European Appln. No. 09 80 849.9 (27 pgs).

European Examination Report dated Mar. 4, 2013 for European Appln. No. 09 808 499.9, 10 pgs.

Cramer et al., "Prospective Identification of Biologically Active Structures by Topomer Shape Similarity Searching," *J. Med. Chem.*, 1999, 42, 3919-3933.

\* cited by examiner

MIF MODULATORS

RELATED APPLICATIONS

This application is a continuation-in-part of U.S. application Ser. No. 12/773,430, filed May 4, 2010, which is a continuation-in-part of PCT International Application No. PCT/US2009/004704 (WO2010021693) filed Aug. 18, 2009, which claims the benefit of U.S. Provisional Application Ser. No. 61/189,327, filed Aug. 18, 2008. The entire contents of the aforementioned related applications are incorporated by reference herein.

RESEARCH SUPPORT

The invention described herein was supported, in whole or in part, by the National Institute of Health Grant Nos. AI043210, AR049610, AR050498, and GM032136. Consequently, the United States government has certain rights in the invention.

FIELD OF THE INVENTION

The present invention relates to novel heterocyclic compounds, pharmaceutical compositions and their use in modulating levels of MIF expression and in treating disorders associated with high or low levels of MIF expression.

BACKGROUND OF THE INVENTION

Macrophage migration inhibitory factor (MIF) is a pro-inflammatory cytokine that is released by T-cells and macrophages. It is viewed to play a key role in a wide range of diseases including rheumatoid arthritis, sepsis, atherosclerosis, asthma, and acute respiratory distress syndrome. MIF also is involved in cell proliferation and differentiation, and anti-MIF antibodies suppress tumor growth and angiogenesis. The biology of MIF and potential biomedical significance of MIF-inhibition are striking, as reviewed elsewhere. Orita, et al., (2002), Macrophage migration inhibitory factor and the discovery of tautomerase inhibitors, *Curr. Pharm. Res.* 8, 1297-1317 ("Orita 2002"); Lolis, et al. (2003), Macrophage migration inhibitory factor, *Expert Opin. Therap. Targets* 7, 153-164; Morand, et al., (2006), MIF: a new cytokine link between rheumatoid arthritis and atherosclerosis. *Nature Rev. Drug Disc.* 5, 399-411. The crystal structure for MIF, which was solved by Prof. Elias Lolis at Yale, revealed a new structural superfamily (Sun, H. et al. (1996) Crystal structure at 2.6-A resolution of human macrophage migration inhibitory factor. *Proc. Nat. Acad. Sci. USA* 93, 5191-5196; Lolis, E. & Bucala, R. (1996) Crystal structure of macrophage migration inhibitory factor (MIF), a glucocorticoid-induced regulator of cytokine production, reveals a unique architecture. *Proc. Assoc. Amer. Physicians* 108, 415-9); the 114-residue MIF monomer has a β/α/β motif and three monomers associate to form a symmetrical trimer. The trimer is toroidal with a solvent-filled central channel. MIF was also found to show structural homology to two prokaryotic tautomerases, and phenylpyruvate and D-dopachrome were discovered to be MIF tautomerase substrates. Rosengren, E.; et al., (1996) The immunoregulatory mediator macrophage migration inhibitory factor (MIF) catalyzes a tautomerization reaction. *Molec. Med.* 2, 143-149; Rosengren, E.; et al. (1997), The macrophage migration inhibitory factor MIF is a phenylpyruvate tautomerase. *FEBS Lett.* 417, 85-8.

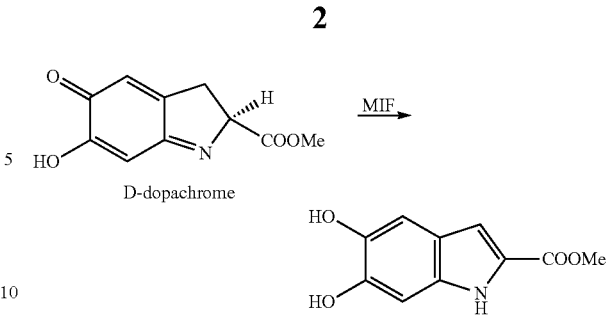

Though L-dopachromes are substrates for a response mechanism of invertebrates to microbial invasion, the catalytic activity of mammalian MIF is likely vestigial. Site-directed mutagenesis and crystallography have identified the MIF active site, and mechanisms for the tautomerase activity have been proposed with key roles for Pro1 as a base and Lys32 as a proton donor (Lubetsky, J. et al. (1999), Pro-1 of macrophage migration inhibitory factor functions as a catalytic base in the phenylpyruvate tautomerase activity. *Biochemistry* 38, 7346-54; Lolis, et al. (2003), Macrophage migration inhibitory factor, *Expert Opin. Therap. Targets* 7, 153-164). Each MIF trimer has three tautomerase active sites, which are well defined cavities located at the interfaces of the monomer subunits. There is also evidence that the interaction of MIF with its receptor, CD74, occurs in this vicinity and MIF inhibition is often directly competitive with MIF-CD74 binding. Senter, P. D., et al., (2002) Inhibition of macrophage migration inhibitory factor (MIF) tautomerase and biological activities by acetaminophen metabolites. *Proc. Nat. Acad. Sci. USA* 99, 144-9 ("Senter 2002"). However, some potent tautomerase inhibitors do not inhibit the biological activity of MIF (Senter 2002).

Discovery of small molecule inhibitors of MIF is clearly important to provide further probes into the biology of MIF and potential therapeutic agents for MIF-related diseases. As reviewed in *Orita* 2002, initial efforts provided some dopachrome (Zhang, X. & Bucala, R. (1999), Inhibition of macrophage migration inhibitory factor (MIF) tautomerase activity by dopachrome analogs. *Bioorg. Med. Chem. Lett.* 9, 3193-3198), glutathione, and hydroxycinnamate analogs in the μM to mM range. Subsequently, a virtual screening exercise with the DOCK program on the Available Chemicals Directory, followed by purchase and assaying of 524 compounds delivered 14 leads with $K_i$ values below 10 μM. However, the diversity is low since all 14 compounds are coumarin derivatives or close analogs (Orita, M., et al. (2001). Coumarin and Chromen-4-one Analogues as Tautomerase Inhibitors of Macrophage Migration Inhibitory Factor: Discovery and X-ray Crystallography. *J. Med. Chem.* 44, 540-547). Coumarins are generally viewed as poor drug leads owing to their promiscuity as protein binders. These authors also reported a crystal structure for a 7-hydroxycoumarin derivative complexed with MIF. Shortly thereafter, the activities of several phenyl-dihydroisoxazoles were published along with the crystal structure for the MIF complex with the most potent one, ISO-1 (Lubetsky, J. B. et al. (2002), The tautomerase active site of macrophage migration inhibitory factor is a potential target for discovery of novel anti-inflammatory agents. *J. Biol. Chem.* 277, 24976-24982). A key feature in the X-ray structures is a hydrogen bond between the phenolic OH and the side-chain CO of Asn97, which forms a backstop for the active site channel. Further optimization enhanced the potency from 7 μM for (R)-ISO-1 to 550 nM for (R)-17 (Cheng, K. F. & Al-Abed, Y. (2006) Critical modifications of the ISO-1 scaffold improve its potent inhibition of macrophage migration inhibitory factor (MIF) tautomerase activity. *Bioorg. Med. Chem. Lett.* 16, 3376-3379).

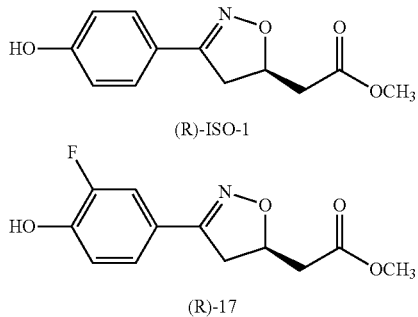

PCT WO2006045505 discloses MIF inhibitors. The MIF inhibitors of PCT WO2006045505 are 3,4-dihydro-benzo[e][1,3]oxazin-2-ones which are substituted at the nitrogen atom by unsubstituted or substituted ($C_3$-8)cycloalkyl, ($C_1$-4)alkyl($C_3$-8)cycloalkyl, ($C_6$-18)aryl or ($C_6$-18)aryl($C_1$-4) alkyl. PCT WO2007070961 discloses MIF-inhibiting benzimidazolone analogues and derivatives.

Given the extent and severity of MIF-associated disorders, there is a continuing need for novel compounds, pharmaceutical compositions, and methods of treatment that modulate levels of MIF expression.

OBJECTS OF THE INVENTION

Various objects of the invention relate to chemical compounds which modulate Macrophage migration inhibitory factor (MIF).

Additional objects of the invention relate to pharmaceutical compounds, methods of modulating MIF and/or treating disease states and/or conditions where MIF modulation (especially agonist and antagonist activity is relevant).

Any one or more of these and/or other aspects of the invention may be readily gleaned from a review of the description of the invention which follows.

BRIEF DESCRIPTION OF THE INVENTION

The present inventors have pursued the development of novel inhibitors and agonists for the interaction of MIF with its receptor, CD74. The work combines computer-aided compound design, synthetic organic chemistry, and biological assaying. Lead generation proceeded by both de novo design and molecular docking of large libraries of commercially available compounds. See Jorgensen, W. L. (2004), The Many Roles of Computation in Drug Discovery. *Science* 303, 1813-1818, and Jorgensen W. L., *Accounts of Chemical Research*, Vol. 42, No. 6, pp. 724-733 (June, 2009), relevant portions of which are incorporated by reference herein.

Accordingly, in one embodiment, the present invention is directed to bicyclic compounds according to the chemical structure (I):

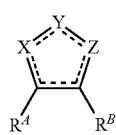

(I)

where X is O, S, N—$R^{XN1}$ or $CR^{XC1}R^{XC2}$;
Y is N—$R^{YN1}$ or $CR^{YC1}R^{YC2}$; and
Z is O, S, N—$R^{ZN1}$ or $CR^{ZC1}R^{ZC2}$, with the proviso that at least one of X or Z is N—$R^{YN1}$ and X and Z are other than O, when Y is O;

$R^{XN1}$ is absent (N is —N═, thus forming a double bond with an adjacent atom), H or an optionally substituted $C_1$-$C_8$ alkyl, alkene or alkyne group, an optionally substituted $C_1$-$C_7$ acyl group, an optionally substituted $(CH_2)_j$-phenyl group or an optionally substituted $(CH_2)_m$-heterocyclic (preferably heteroaryl) group, or an optionally substituted carbonyl phenyl group, or an optionally substituted carbonyl heteroaryl group;

$R^{YN1}$ is absent, H, an optionally substituted $C_1$-$C_8$ alkyl, alkene or alkyne group, an optionally substituted $C_1$-$C_8$ acyl group, an optionally substituted $(CH_2)_j$-phenyl group or an optionally substituted $(CH_2)_m$-heterocyclic (preferably heteroaryl) group, or an optionally substituted carbonyl phenyl group, or an optionally substituted carbonyl heteroaryl group;

$R^{ZN1}$ is absent, H, an optionally substituted $C_1$-$C_8$ alkyl, alkene or alkyne group, an optionally substituted $C_1$-$C_8$ acyl group, an optionally substituted $(CH_2)_j$-phenyl group or an optionally substituted $(CH_2)_m$-heterocyclic (preferably heteroaryl) group, or an optionally substituted carbonyl phenyl group, or an optionally substituted carbonyl heteroaryl group;

$R^{XC1}$ is absent (C is —C═, thus forming a double bond with an adjacent atom), H, an optionally substituted $C_1$-$C_3$ alkyl, or together with $R^{XC2}$ forms a ═O (keto) or ═C group, (preferably $R^{XC1}$ is absent);

$R^{XC2}$ is H, halogen, cyano, an optionally substituted $C_1$-$C_8$ alkyl, alkene or alkyne group (preferably $R^{XC2}$ is an optionally substituted $C_1$-$C_3$ group when $R^{XC1}$ is an optionally substituted $C_1$-$C_3$ group), an optionally substituted $C_1$-$C_8$ acyl group, an optionally substituted $C_2$-$C_8$ ester (hydroxyester) or carboxyester group, an optionally substituted $C_1$-$C_7$ alkoxy group, an optionally substituted $C_2$-$C_8$ ether group, an optionally substituted $C_1$-$C_7$ amido or carboxamido group, a $C_1$-$C_7$ urethane or urea group, an optionally substituted $(CH_2)_j$-phenyl group or an optionally substituted $(CH_2)_m$-heterocyclic (preferably heteroaryl) group, or together with $R^{XC1}$ forms a ═O (keto) or ═C group, which is optionally substituted with a $C_1$-$C_6$ alkyl group, an optionally substituted $(CH_2)_j$-phenyl group or an optionally substituted $(CH_2)_m$-heterocyclic (preferably heteroaryl) group;

$R^{YC1}$ is absent, H, an optionally substituted $C_1$-$C_3$ alkyl, or together with $R^{YC2}$ forms a ═O (keto) or ═C which is optionally substituted with a heterocyclic group;

$R^{YC2}$ is H, halogen, cyano, an optionally substituted $C_1$-$C_8$ alkyl, alkene or alkyne group (preferably $R^{YC2}$ is an optionally substituted $C_1$-$C_3$ group when $R^{YC1}$ is an optionally substituted $C_1$-$C_3$ group), an optionally substituted $C_1$-$C_7$ acyl group, an optionally substituted $C_2$-$C_8$ ester or carboxyester group, an optionally substituted $C_1$-$C_{10}$ alkoxy group, an optionally substituted $C_2$-$C_8$ ether group, an optionally substituted $C_1$-$C_7$ amido or carboxamido group, a $C_1$-$C_7$ urethane or urea group, an optionally substituted $(CH_2)_j$-phenyl group or an optionally substituted $(CH_2)_m$-heterocyclic (preferably heteroaryl) group, or together with $R^{YC1}$ forms a ═O (keto) or ═C group, which is optionally substituted with a $C_1$-$C_6$ alkyl group, an optionally substituted (CH₂)j-phenyl group or an optionally substituted (CH₂)m-heterocyclic (preferably heteroaryl) group;

$R^{ZC1}$ is absent, H, an optionally substituted $C_1$-$C_3$ alkyl, or together with $R^{ZC2}$ forms a =O (keto) group or a =C group, (preferably $R^{ZC1}$ is absent);

$R^{ZC2}$ is H, halogen, cyano, an optionally substituted $C_1$-$C_8$ alkyl, alkene or alkyne group (preferably $R^{ZC2}$ is an optionally substituted $C_1$-$C_3$ group when $R^{ZC1}$ is an optionally substituted $C_1$-$C_3$ group), an optionally substituted $C_1$-$C_8$ acyl group, an optionally substituted $C_2$-$C_8$ ester or carboxyester group, an optionally substituted $C_1$-$C_7$ alkoxy group, an optionally substituted $C_2$-$C_8$ ether group, an optionally substituted $C_1$-$C_7$ amido or carboxamido group, a $C_1$-$C_7$ urethane or urea group, an optionally substituted (CH₂)j-phenyl group or an optionally substituted (CH₂)m-heterocyclic (preferably heteroaryl) group, or together with $R^{ZC1}$ forms a =O (keto) or =C group, which is optionally substituted with a $C_1$-$C_6$ alkyl group, an optionally substituted (CH₂)j-phenyl group or an optionally substituted (CH₂)m-heterocyclic (preferably heteroaryl) group;

$R^A$ and $R^B$ together form an optionally substituted 5, 6 or 7 membered carbocyclic or heterocyclic ring (preferably an optionally substituted 6-membered aromatic or heteroaromatic ring, more preferably an optionally substituted phenyl ring or a heteroaromatic ring containing one nitrogen group, preferably a pyridyl group);

each j is independently 0, 1, 2, 3, 4 or 5; and each m is 0, 1, 2, 3, 4, or 5;

or a pharmaceutically acceptable salt, enantiomer, solvate or polymorph thereof;

In certain preferred embodiments, the present invention is directed to 6:5 fused ring compounds according to the structure (II):

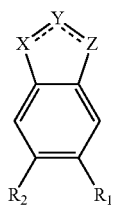

II where X, Y Z are as described above for compound (I); and $R_1$ and $R_2$ are each independently H, OH, COOH, halogen (F, Cl, Br, I), CN, OH, optionally substituted $C_1$-$C_8$ alkyl, optionally substituted O—($C_1$-$C_6$)alkyl, SH, S—($C_1$-$C_6$) alkyl, optionally substituted $C_1$-$C_8$ acyl, optionally substituted $C_2$-$C_8$ ether, optionally substituted $C_2$-$C_8$ ester or carboxyester, optionally substituted $C_2$-$C_8$ thioester, amide optionally substituted with a $C_1$-$C_6$ alkyl group, carboxyamide optionally substituted with one or two $C_1$-$C_6$ alkyl or alkanol groups, and amine optionally substituted with one or two $C_1$-$C_6$ alkyl or alkanol groups. Preferably $R_1$ and $R_2$ are independently H, $CH_3$, $CH_2CH_3$, $NH_2$, $NHCH_3$, $N(CH_3)_2$, OH, $OCH_3$, SH, $SCH_3$, F, Cl, Br or I.

In another aspect, compounds according to the present invention have the chemical structure (II)(A):

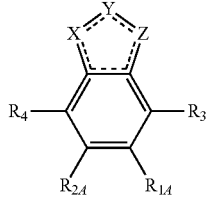

(II)(A)

wherein X is O, S, N—$R^1$ or $CR^{XC1}R^{XC2}$;

Y is N—$R^{YN1}$ or $CR^{YC1}R^{YC2}$;

Z is O, S, N—$R^{ZN1}$ or $CR^{ZC1}R^{ZC2}$, with the proviso that one of X, Y, or Z is, respectively, $CR^{XC1}R^{XC2}$, $CR^{YC1}R^{YC2}$, or $CR^{ZC1}R^{ZC2}$;

$R^{XN1}$ is absent (N is —N=, thus forming a double bond with an adjacent atom), H or an optionally substituted $C_1$-$C_8$ alkyl, alkene or alkyne group, an optionally substituted $C_1$-$C_7$ acyl group, an optionally substituted (CH₂)j-phenyl group or an optionally substituted (CH₂)$_m$-heterocyclic (preferably heteroaryl) group, or an optionally substituted carbonyl phenyl or an optionally substituted carbonyl heteroaryl group;

$R^{YN1}$ is absent, H, an optionally substituted $C_1$-$C_8$ alkyl, alkene or alkyne group; an optionally substituted $C_1$-$C_8$ acyl group, an optionally substituted (CH₂)j-phenyl group or an optionally substituted (CH₂)m-heterocyclic (preferably heteroaryl) group, or an optionally substituted carbonyl phenyl or an optionally substituted carbonyl heteroaryl group;

$R^{ZN1}$ is absent, H, an optionally substituted $C_1$-$C_8$ alkyl, alkene or alkyne group, an optionally substituted $C_1$-$C_8$ acyl group, an optionally substituted (CH₂)j-phenyl group or an optionally substituted (CH₂)m-heterocyclic (preferably heteroaryl) group, or an optionally substituted carbonyl phenyl or an optionally substituted carbonyl heteroaryl group;

$R^{XC1}$ is absent (C is —C=, thus forming a double bond with an adjacent atom), H, an optionally substituted $C_1$-$C_3$ alkyl, or together with $R^{XC2}$ forms a =O (keto) or =C group, (preferably $R^{XC1}$ is absent);

$R^{XC2}$ is H, halogen, cyano, an optionally substituted $C_1$-$C_8$ alkyl, alkene or alkyne group (preferably $R^{XC2}$ is an optionally substituted $C_1$-$C_3$ group when $R^{XC1}$ is an optionally substituted $C_1$-$C_3$ group), an optionally substituted $C_1$-$C_8$ acyl group, an optionally substituted $C_2$-$C_8$ ester (hydroxyester) or carboxyester group, an optionally substituted $C_1$-$C_7$ alkoxy group, an optionally substituted $C_2$-$C_8$ ether group, an optionally substituted $C_1$-$C_7$ amido or carboxamido group, a $C_1$-$C_7$ urethane or urea group, an optionally substituted (CH₂)j-phenyl group or an optionally substituted (CH₂)m-heterocyclic (preferably heteroaryl) group, or together with $R^{XC1}$ forms a =O (keto) or =C group, which is optionally substituted with a $C_1$-$C_6$ alkyl group, an optionally substituted (CH₂)j-phenyl group or an optionally substituted (CH₂)m-heterocyclic (preferably heteroaryl) group, or an optionally substituted carbonyl phenyl or an optionally substituted carbonyl heteroaryl group;

$R^{YC1}$ is absent, H, an optionally substituted $C_1$-$C_3$ alkyl, or together with $R^{YC2}$ forms a =O (keto) or =C which is optionally substituted with a heterocyclic group;

$R^{YC2}$ is H, halogen, cyano, an optionally substituted $C_1$-$C_8$ alkyl, alkene or alkyne group (preferably $R^{YC2}$ is an optionally substituted $C_1$-$C_3$ group when $R^{YC1}$ is an optionally substituted $C_1$-$C_3$ group), an optionally substituted $C_1$-$C_7$ acyl group, an optionally substituted $C_2$-$C_8$ ester or carboxyester group, an optionally substituted $C_1$-$C_{10}$ alkoxy group, an optionally substituted $C_2$-$C_8$ ether group, an optionally substituted $C_1$-$C_7$ amido or carboxamido group, a $C_1$-$C_7$ urethane or urea group, an optionally substituted $(CH_2)$j-phenyl group or an optionally substituted $(CH_2)$m-heterocyclic (preferably heteroaryl) group, or together with $R^{YC1}$ forms a =O (keto) or =C group, which is optionally substituted with a $C_1$-$C_6$ alkyl group, an optionally substituted $(CH_2)$j-phenyl group or an optionally substituted $(CH_2)$m-heterocyclic (preferably heteroaryl) group, or an optionally substituted carbonyl phenyl or an optionally substituted carbonyl heteroaryl group;

provided that when $R^{XC1}$ and $R^{YC1}$ are absent, $R^{XC2}$ and $R^{YC2}$ can together form an optionally substituted 5, 6 or 7 membered carbocyclic or heterocyclic ring (preferably an optionally substituted 6-membered aromatic or heteroaromatic ring, more preferably an optionally substituted phenyl ring or a heteroaromatic ring);

$R^{ZC1}$ is absent, H, an optionally substituted $C_1$-$C_3$ alkyl, or together with $R^{ZC2}$ forms a =O (keto) group or a =C group, (preferably $R^{ZC1}$ is absent);

$R^{ZC1}$ is H, halogen, cyano, an optionally substituted $C_1$-$C_8$ alkyl, alkene or alkyne group (preferably $R^{ZC2}$ is an optionally substituted $C_1$-$C_3$ group when $R^{ZC1}$ is an optionally substituted $C_1$-$C_3$ group), an optionally substituted $C_1$-$C_8$ acyl group, an optionally substituted $C_2$-$C_8$ ester or carboxyester group, an optionally substituted $C_1$-$C_7$ alkoxy group, an optionally substituted $C_2$-$C_8$ ether group, an optionally substituted $C_1$-$C_7$ amido or carboxamido group, a $C_1$-$C_7$ urethane or urea group, an optionally substituted $(CH_2)$j-phenyl group or an optionally substituted $(CH_2)$m-heterocyclic (preferably heteroaryl) group, or together with $R^{ZC1}$ forms a =O (keto) or =C group, which is optionally substituted with a $C_1$-$C_6$ alkyl group, an optionally substituted $(CH_2)$j-phenyl group or an optionally substituted $(CH_2)$m-heterocyclic (preferably heteroaryl) group, or an optionally substituted carbonyl phenyl group or an optionally substituted carbonyl heteroaryl group;

each j is independently 0, 1, 2, 3, 4 or 5;

each m is 0, 1, 2, 3, 4, or 5;

$R_{1A}$, $R_{2A}$, $R_3$, and $R_4$ are the same or different and are each independently H, OH, COOH, halogen (F, Cl, Br, I), CN, OH, an optionally substituted $C_1$-$C_8$ alkyl, alkene or alkyne group, optionally substituted O—($C_1$-$C_8$ alkyl, alkene or alkyne) group, SH, S—($C_1$-$C_6$)alkyl, optionally substituted $C_1$-$C_8$ acyl, optionally substituted $C_2$-$C_8$ ether, optionally substituted $C_2$-$C_8$ ester or carboxyester, optionally substituted $C_2$-$C_8$ thioester, amide optionally substituted with a $C_1$-$C_6$ alkyl group, carboxyamide optionally substituted with one or two $C_1$-$C_6$ alkyl or alkanol groups, amine optionally substituted with one or two $C_1$-$C_6$ alkyl or alkanol groups, an optionally substituted $(CH_2)$j-phenyl group, an optionally substituted $(CH_2)_m$-heterocyclic (preferably heteroaryl) group, an optionally substituted —O—$(CH_2)$j-phenyl group or an optionally substituted —O—$(CH_2)_m$-heterocyclic (preferably heteroaryl) group, or an optionally substituted carbonyl phenyl or an optionally substituted carbonyl heteroaryl group;

or a pharmaceutically acceptable salt, stereoisomer (e.g. enantiomer or diastereomer), solvate or polymorph thereof; provided that the compound is not MIF009, MIF010, MIF011, MIF014, MIF015, MIF016, MIF017, MIF018, MIF019, MIF22, MIF23, MIF24, MIF25, MIF26, MIF27, MIF28, MIF29, MIF38, MIF39, MIF40, MIF41, MIF42, MIF43, MIF44, MIF45, or MIF64.

In preferred aspects of compounds of formula (II)(A):

(1) X is N—$R^{XN1}$, $R^{XN1}$ is absent, Y is $CR^{YC1}R^{YC2}$, $R^{YC1}$ is absent, $R^{YC2}$ is an optionally substituted $(CH_2)$j-phenyl group, an optionally substituted $(CH_2)_m$-heterocyclic (preferably heteroaryl) group, an optionally substituted carbonyl phenyl group, an optionally substituted carbonyl heteroaryl group, or $R^{YC1}$ together with $R^{YC2}$ forms a =O (keto) group, and Z is S; or (2) X is $CR^{XC1}R^{XC2}$, $R^{XC1}$ is absent and $R^{XC2}$ is H, OH, COOH, halogen (F, Cl, Br, I), CN, OH, an optionally substituted $C_1$-$C_8$ alkyl, alkene or alkyne group, optionally substituted O—($C_1$-$C_8$ alkyl, alkene or alkyne) group, Y is $CR^{YC1}R^{YC2}$, $R^{YC1}$ is absent and $R^{YC2}$ is an optionally substituted $(CH_2)$j-phenyl group, an optionally substituted $(CH_2)_m$-heterocyclic (preferably heteroaryl) group, an optionally substituted carbonyl phenyl group, an optionally substituted carbonyl heteroaryl group, and Z is N—$R^{ZN1}$, $R^{ZN1}$ is absent, H, OH, COOH, halogen (F, Cl, Br, I), CN, OH, an optionally substituted $C_1$-$C_8$ alkyl, alkene or alkyne group, optionally substituted O—($C_1$-$C_8$ alkyl, alkene or alkyne) group, or an optionally substituted $C_1$-$C_8$ acyl group; or (3) X is N—$R^{XN1}$, $R^{XN1}$ is absent, Y is N—$R^{YN1}$, $R^{YN1}$ is an optionally substituted $(CH_2)$j-phenyl group, an optionally substituted $(CH_2)$m-heterocyclic (preferably heteroaryl) group, an optionally substituted carbonyl phenyl group, an optionally substituted carbonyl heteroaryl group, and Z is $CR^{ZC1}R^{ZC2}$, $CR^{ZC1}$ is absent and $R^{ZC2}$ is H, OH, COOH, halogen (F, Cl, Br, I), CN, OH, an optionally substituted $C_1$-$C_8$ alkyl, alkene or alkyne group, an optionally substituted O—($C_1$-$C_8$ alkyl, alkene or alkyne) group, or an optionally substituted $C_1$-$C_8$ acyl group; or (4) X is N—$R^{XN1}$, $R^{XN1}$ is absent, Y is $CR^{YC1}R^{YC2}$, $R^{YC1}$ is absent and $R^{YC2}$ is an optionally substituted $(CH_2)$j-phenyl group, an optionally substituted $(CH_2)_m$-heterocyclic (preferably heteroaryl) group, an optionally substituted carbonyl phenyl group, an optionally substituted carbonyl heteroaryl group, and Z is N—$R^{ZN1}$, $R^{ZN1}$ is absent, H, OH, COOH, halogen (F, Cl, Br, I), CN, OH, an optionally substituted $C_1$-$C_8$ alkyl, alkene or alkyne group, an optionally substituted O—($C_1$-$C_8$ alkyl, alkene or alkyne) group, or an optionally substituted $C_1$-$C_8$ acyl group; or (5) X is O, Y is $CR^{YC1}R^{YC2}$, $R^{YC1}$ together with $R^{YC2}$ forms a =O (keto) group, and Z is N—$R^{ZN1}$, $R^{ZN1}$ is H, OH, COOH, halogen (F, Cl, Br, I), CN, OH, an optionally substituted $C_1$-$C_8$ alkyl, alkene or alkyne group, an optionally substituted O—($C_1$-$C_8$ alkyl, alkene or alkyne) group, an optionally substituted $C_1$-$C_8$ acyl group, an optionally substituted $(CH_2)$j-phenyl group, an optionally substituted $(CH_2)_m$-heterocyclic (preferably heteroaryl) group, an optionally substituted carbonyl phenyl group, or an optionally substituted carbonyl heteroaryl group; or (6) X is $CR^{XC1}R^{XC2}$, $R^{XC1}$ together with $R^{XC2}$ forms a =O (keto) group, Y is N—$R^{YN1}$, $R^{YN1}$ is an optionally substituted $(CH_2)$j-phenyl group, an optionally substituted $(CH_2)_m$-heterocyclic (preferably heteroaryl) group, an optionally substituted carbonyl phenyl group, an optionally substituted carbonyl heteroaryl group, and Z is S; or (7) X is $CR^{XC1}R^{XC2}$, $R^{XC1}$ together with $R^{XC2}$ forms a =O (keto) group, Y is N—$R^{YN1}$, $R^{YN1}$ is an optionally substituted $(CH_2)$j-phenyl group, an optionally substituted $(CH_2)_m$-heterocyclic (preferably heteroaryl) group, an optionally substituted carbonyl phenyl group, an optionally substituted carbonyl heteroaryl group, Z is $CR^{ZC1}R^{ZC2}$, and $CR^{ZC1}$ and $R^{ZC2}$ are H; or (8) X is O, Y is $CR^{YC1}R^{YC2}$, $R^{YC1}$ is absent and $R^{YC2}$ is an optionally substituted carbonyl phenyl group, an optionally substituted carbonyl heteroaryl group, an optionally substituted $(CH_2)$j-phenyl group, or an optionally substituted $(CH_2)_m$ heterocyclic (preferably heteroaryl) group, and Z is $CR^{ZC1}R^{ZC2}$, $CR^{ZC1}$ is absent and $R^{ZC2}$ is H; or (9) X is $CR^{XC1}R^{XC2}$, $R^{XC1}$ is absent and $R^{XC2}$ is H, an optionally substituted acyl group, Y is $CR^{YC1}R^{YC2}$, $R^{YC1}$ is absent and $R^{YC2}$ is an optionally substituted carbonyl phenyl group, an optionally substituted carbonyl heteroaryl group, an optionally substituted $(CH_2)$j-phenyl group, or an optionally substituted $(CH_2)_m$ heterocyclic (preferably heteroaryl) group, and Z is O; or

(10) X is $CR^{XC1}R^{XC2}$, $R^{XC1}$ is absent, Y is $CR^{YC1}R^{YC2}$, $R^{YC1}$ is absent, $R^{XC2}$ and $R^{YC2}$ together form an optionally substituted 6-membered aromatic or heteroaromatic ring, and Z is O, S or N—$R^{ZN1}$, and $R^{ZN1}$ is H, an optionally substituted $C_1$-$C_8$ alkyl, alkene or alkyne group, an optionally substituted $C_1$-$C_8$ acyl group, an optionally substituted $(CH_2)$j-phenyl group, an optionally substituted $(CH_2)$m-heterocyclic (preferably heteroaryl) group, an optionally substituted carbonyl phenyl or an optionally substituted carbonyl heteroaryl group.

In still other preferred aspects of compounds of formula (II)(A):

(1)(A) X is N—$R^{XN1}$, $R^{XN1}$ is absent, Y is $CR^{YC1}R^{YC2}$, $R^{YC1}$ is absent, $R^{YC2}$ is an optionally substituted $(CH_2)$j-phenyl group, and Z is S; or (2)(A) X is $CR^{XC1}R^{XC2}$, $R^{XC1}$ is absent and $R^{XC2}$ is H, Y is $CR^{YC1}R^{YC2}$, $R^{YC1}$ is absent and $R^{YC2}$ is an optionally substituted $(CH_2)$j-phenyl group or an optionally substituted $(CH_2)_m$ heterocyclic (preferably heteroaryl) group, and Z is N—$R^{ZN1}$, $R^{ZN1}$ is absent, H, an optionally substituted $C_1$-$C_8$ alkyl, alkene or alkyne group, or an optionally substituted $C_1$-$C_8$ acyl group; or (3)(A) X is N—$R^{XN1}$, $R^{XN1}$ is absent, Y is N—$R^{YN1}$, $R^{YN1}$ is an optionally substituted $(CH_2)$j-phenyl group, and Z is $CR^{ZC1}R^{ZC2}$, $CR^{ZC1}$ an is absent and $R^{ZC2}$ is H; or (4)(A) X is N—$R^{XN1}$, $R^{XN1}$ is absent, Y is $CR^{YC1}R^{YC2}$, $R^{YC1}$ is absent and $R^{YC2}$ is an optionally substituted $(CH_2)$j-phenyl group, and Z is N—$R^{ZN1}$, $R^{ZN1}$ is absent, H, an optionally substituted $C_1$-$C_8$ alkyl, alkene or alkyne group, or an optionally substituted $C_1$-$C_8$ acyl group; or (5)(A) X is O, Y is $CR^{YC1}R^{YC2}$, $R^{YC1}$ together with $R^{YC2}$ forms a =O (keto) group, and Z is N—$R^{ZN1}$, $R^{ZN1}$ is an optionally substituted $(CH_2)$j-phenyl group; or (6)(A) X is $CR^{XC1}R^{XC2}$, $R^{XC1}$ together with $R^{XC2}$ forms a =O (keto) group, Y is N—$R^{YN1}$, $R^{YN1}$ is an optionally substituted $(CH_2)$j-phenyl group, and Z is S; or (7)(A) X is $CR^{XC1}R^{XC2}$, $R^{XC1}$ together with $R^{XC2}$ forms a =O (keto) group, Y is N—$R^{N1}$, $R^{YN1}$ is an optionally substituted $(CH_2)$j-phenyl group, Z is $CR^{ZC1}R^{ZC2}$, and $CR^{ZC1}$ and $R^{ZC2}$ are H; or (8)(A) X is O, Y is $CR^{YC1}R^{YC}2$, $R^{YC1}$ is absent and $R^{YC2}$ is an optionally substituted carbonyl phenyl group, Z is $CR^{ZC1}R^{ZC2}$, $R^{ZC1}$ is absent, and $R^{ZC2}$ is H; or (9)(A) X is $CR^{XC1}R^{XC2}$, $R^{XC1}$ is absent and $R^{XC2}$ is H, Y is $CR^{YC1}R^{YC2}$, $R^{YC1}$ is absent and $R^{YC2}$ is an optionally substituted carbonyl phenyl group, and Z is O; or

(10) X is $CR^{XC1}R^{XC2}$, $R^{XC1}$ is absent, Y is $CR^{YC1}R^{YC2}$, $R^{YC1}$ is absent $R^{XC2}$ and $R^{YC2}$ together form a substituted 6-membered aromatic ring, and Z is O or S, and at least one of $R_{1A}$, $R_{2A}$$R_3$, and $R_4$ are not H.

Non-limiting examples of formula (II)(A) compounds include, together with any additional novel compounds set forth hereinbelow, (or as defined or depicted in tables 1-25).

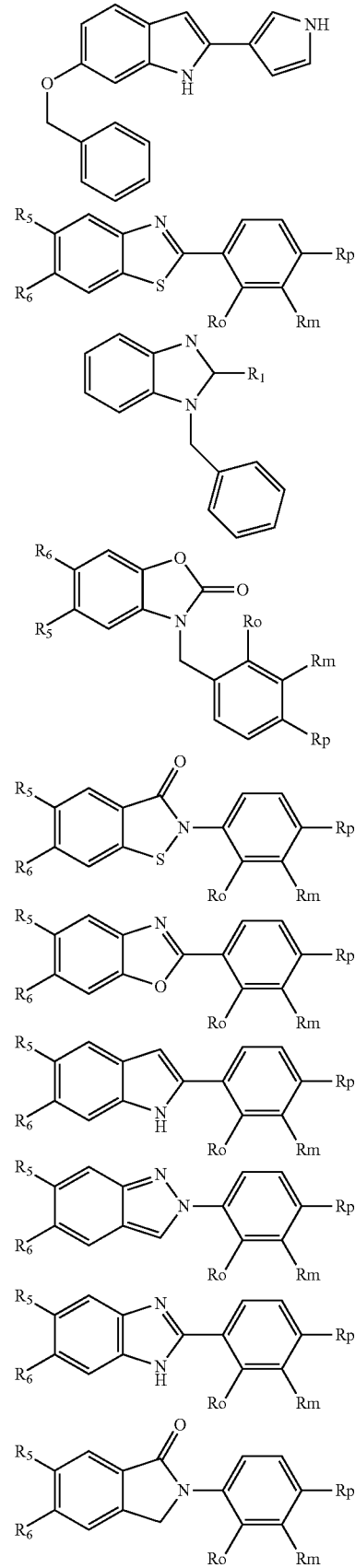

MIF-001

-continued

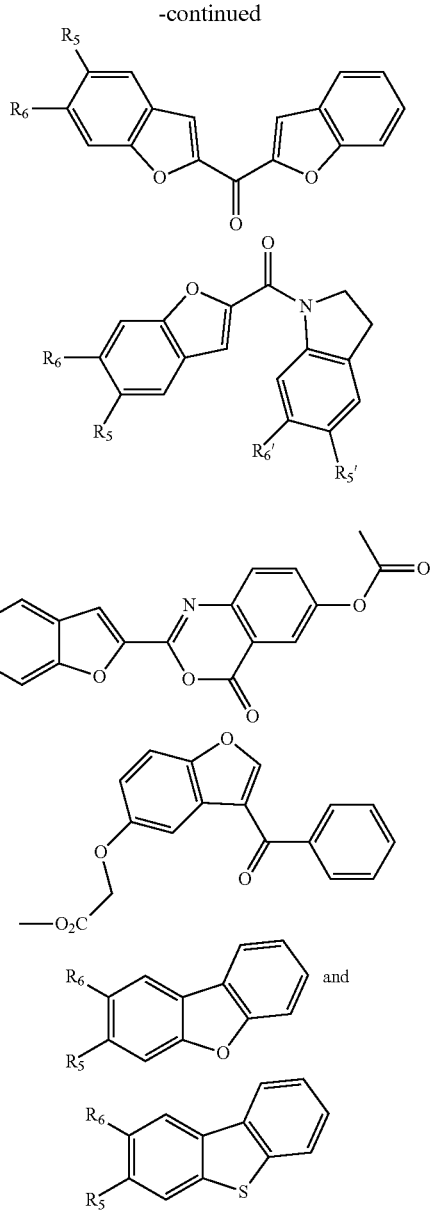

MIF: 17 where $R_5$, $R_6$, $R_5^1$, $R_6^1$, $R_7$, $R_o$, $R_m$, and $R_p$ have the same definition as $R_{1-4}$, $R_2$, $R_3$, and $R_4$ in formula (II)(A) (most preferably, $R_5$, $R_6$, $R_5^1$, $R_6^1$, $R_7$ are the same or different and are independently H, halo, CN, an optionally substituted $C_1$-$C_8$ alkyl, alkene or alkyne group, or an optionally substituted O—($C_1$-$C_8$ alkyl, alkene or alkyne) group and $R_o$, $R_m$, and $R_p$ are the same or different and are independently H, halo, CN, an optionally substituted $C_1$-$C_8$ alkyl, alkene or alkyne group, an optionally substituted O—($C_1$-$C_8$ alkyl, alkene or alkyne) group, an optionally substituted $C_1$-$C_8$ acyl, an optionally substituted $C_2$-$C_8$ ether, an optionally substituted $(CH_2)_j$-phenyl group, an optionally substituted $(CH_2)_m$-heterocyclic (preferably heteroaryl) group, an optionally substituted —O—$(CH_2)_j$-phenyl group or an optionally substituted —O—$(CH_2)_m$-heterocyclic (preferably heteroaryl) group.

Particularly preferred examples of formula (II)(A) compounds according to (1)-(10) or (1)(A)-(10)(A) above include:

MF103

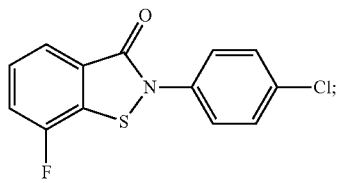

MF107

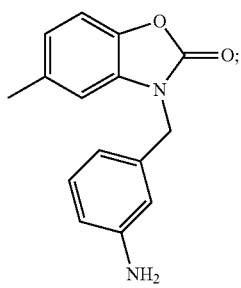

MF112

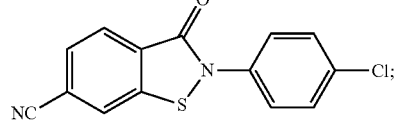

MF108

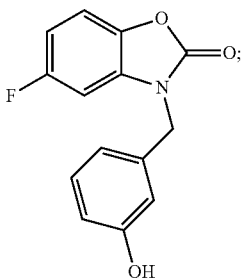

The compound MIF098 and its possible primary metabolites, shown below:

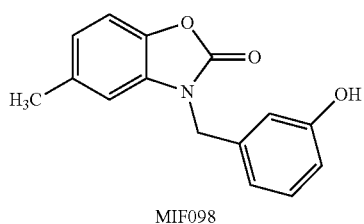

MIF098

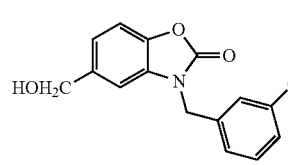
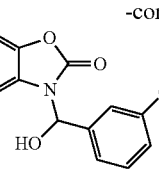
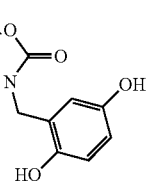
and the analogs of the compound MIF098 shown below:
In another aspect of the present invention, compounds according to the present invention have the following chemical structures A-N as depicted below
MIF139
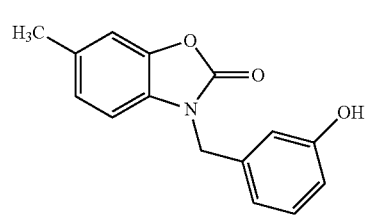
MIF108
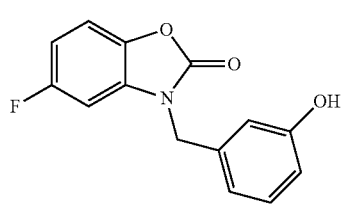
MIF046
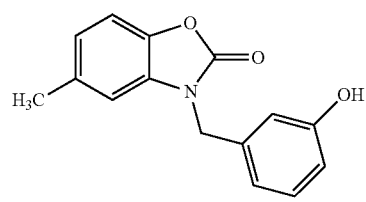
MIFhom
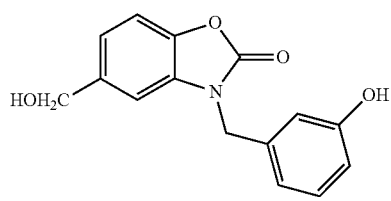
MIFacid
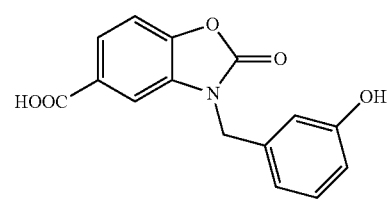
A
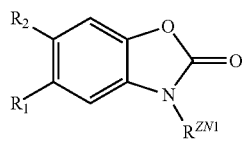
B
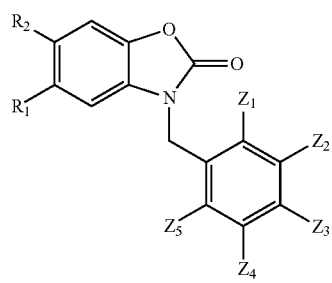
C
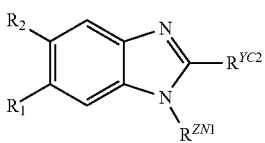
D
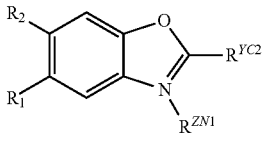
E
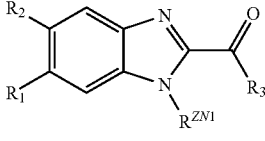
F
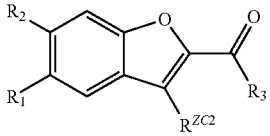

-continued

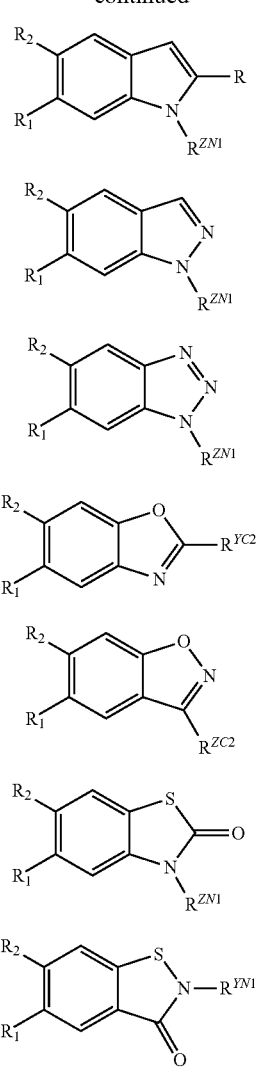

G

H

J

K

L

M

N wherein $R^{YN1}$, $R^{ZN1}$, $R^{YC2}$ and $R^{ZC2}$ are as described above for compound (II);

$R_1$, $R_2$, $Z_1$, $Z_2$, $Z_3$, $Z_4$ and $Z_5$ are each independently H, hydroxyl, optionally substituted $C_1$-$C_8$ alkyl, alkene or alkyne group, optionally substituted $C_1$-$C_8$ acyl group, optionally substituted $C_2$-$C_8$ ether, optionally substituted or $C_2$-$C_8$ ester group, an optionally substituted $C_5$-$C_{11}$ $(CH_2)_j$-carbocyclic group wherein said carbocyclic group forms an optionally substituted 5, 6 or 7-membered ring (preferably, a $(CH_2)_j$-phenyl group, where the phenyl group is optionally substituted), or an optionally substituted $(CH_2)_m$-heterocyclic group (preferably, an optionally substituted heteroaryl) group, alkoxy, halogen, carboxylic acid, cyano, ether, ester, acyl, nitro, amine (including mono- or di-alkyl substituted amines), or $(CH_2)_j$—OH;

$R_3$ is H, an optionally substituted $C_1$-$C_6$ alkyl group, an optionally substituted O—$(C_1$-$C_6)$alkyl, an optionally substituted aryl group or heterocyclic group;

each j is independently 0, 1, 2, 3, 4 or 5; and each m is 0, 1, 2, 3, 4, or 5;

or a pharmaceutically acceptable salt, enantiomer, solvate or polymorph thereof. In certain preferred aspects of this invention, $R_1$ and $R_2$ are H, $CH_3$, $CH_2CH_3$, $NH_2$, $NHCH_3$, $N(CH_3)_2$, OH, $OCH_3$, SH, $SCH_3$, F, Cl, Br or I. $R_3$ is preferably an optionally substituted phenyl group or an optionally substituted heterocyclic group, preferably an optionally substituted heteroaryl group containing a single ring or fused rings (preferably 6:5) such as benzofuran, indole or 2,3-dihydroindole.

In these aspects of the invention compound (A) represents benooxazolone derivatives, including N-benzyl analogs (B). (C) and (D) represent benzoimidazole and benzofuran derivatives, including acyl analogs (E) and (F) where $R_3$ can be a small group or another mono or bicyclic heterocycle such as a benzofuran, indole or 2,3-dihydroindole. Additional representative structures are substituted indoles G, benzopyrazoles H, benzotriazoles J, benzooxazoles K, benzoisoxazoles L, benzothiazolones M, and benzoisothiazolones N, and corresponding compounds with oxygen replacing sulfur or vice versa. In certain embodiments of the compounds of chemical structure (A-N), $R_1$ and $R_2$ are each independently H, $CH_3$, $CH_2CH_3$, $NH_2$, $NHCH_3$, $N(CH_3)_2$, OH, $OCH_3$, SH, $SCH_3$, F, Cl, Br or I. In other aspects of the invention, $R_1$ and $R_2$ are each independently selected from the group consisting of H, hydroxyl, optionally substituted $C_1$-$C_8$ alkyl, or $(CH_2)_j$—OH; and at least one of $Z_1$-$Z_5$ is a $C_1$-$C_6$ alkoxy group.

In one embodiment, compounds of the invention provide benzoxazolone derivatives, A, including the N-benzyl analogs B. Wherein $R_1$, $R_2$ and $Z_1$-$Z_5$ are each independently small aliphatic or heteroatom containing groups; primary examples are H, $CH_3$, $CH_2CH_3$, $NH_2$, $NHCH_3$, $N(CH_3)_2$, OH, $OCH_3$, SH, $SCH_3$, F, Cl, Br, and I.

In another more particular aspect of the present invention, compounds according to the present invention have the following chemical structure (III):

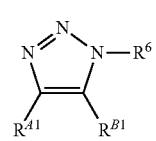

(III)

wherein $R^{A1}$ and $R^{B1}$ are independently H, halogen, cyano, an optionally substituted $C_1$-$C_8$ alkyl, alkene or alkyne group, an optionally substituted an optionally substituted acyl group, an optionally substituted $C_2$-$C_8$ ester or carboxyester group, an optionally substituted $C_1$-$C_{10}$ alkoxy group, an optionally substituted $C_2$-$C_8$ ether group, an optionally substituted $C_1$-$C_7$ amido or carboxamido group, a $C_1$-$C_7$ urethane or urea group, =O, an optionally substituted $(CH_2)_j$-phenyl group, an optionally substituted $(CH_2)$m-heterocyclic group, an optionally substituted carbonyl phenyl group, or an an optionally substituted carbonyl heteroaryl group;

or $R^{A1}$ and $R^{B1}$ form a 5, 6 or 7 membered optionally substituted carbocyclic ring or heterocyclic group;

$R^6$ is H, an optionally substituted $C_1$-$C_8$ alkyl, alkene or alkyne group, an optionally substituted $C_5$-$C_{14}$ $(CH_2)_j$-carbocyclic group wherein said carbocyclic group preferably forms an optionally substituted 5, 6 or 7-membered ring (preferably, a $(CH_2)_j$-aryl group, e.g., a $(CH_2)_j$-phenyl group, wherein the aryl or phenyl group is optionally substituted), an optionally substituted acyl group (preferably an optionally substituted carbonyl phenyl or an optionally substituted carbonyl heteroaryl group), or an optionally substituted $C_4$-$C_{13}$ $(CH_2)_m$-heterocyclic group (preferably, an optionally substituted heteroaryl) group;

each j is independently 0, 1, 2, 3, 4 or 5; and each m is independently 0, 1, 2, 3, 4, or 5;

or a pharmaceutically acceptable salt, enantiomer, solvate or polymorph thereof.

In other preferred embodiments of the compounds of chemical structure (III):

(1) $R^6$ is an optionally substituted $C_5$-$C_{11}$ $(CH_2)_j$-carbocyclic group wherein said carbocyclic group forms a 5, 6 or 7-membered ring (preferably, an optionally substituted $(CH_2)_j$-phenyl group), or an optionally substituted $(CH_2)_m$-heterocyclic group (preferably, an optionally substituted $(CH_2)_m$-heteroaryl) group; and $R^{A1}$ and $R^{B1}$ form an optionally substituted phenyl or pyridyl group, or (2) $R^6$ is an optionally substituted $(CH_2)_j$-phenyl group, an optionally substituted $(CH_2)_m$-heterocyclic (preferably heteroaryl) group, or an optionally substituted acyl group, an optionally substituted carbonyl phenyl group, or an optionally substituted carbonyl heteroaryl group, $R^{B1}$ is H, and $R^{A1}$ is an optionally substituted $(CH_2)_j$-phenyl group, an optionally substituted $(CH_2)_m$-heterocyclic (preferably heteroaryl) group, or an optionally substituted acyl group, an optionally substituted carbonyl phenyl group, or an optionally substituted carbonyl heteroaryl group.

Preferred compounds of formula (III) include:

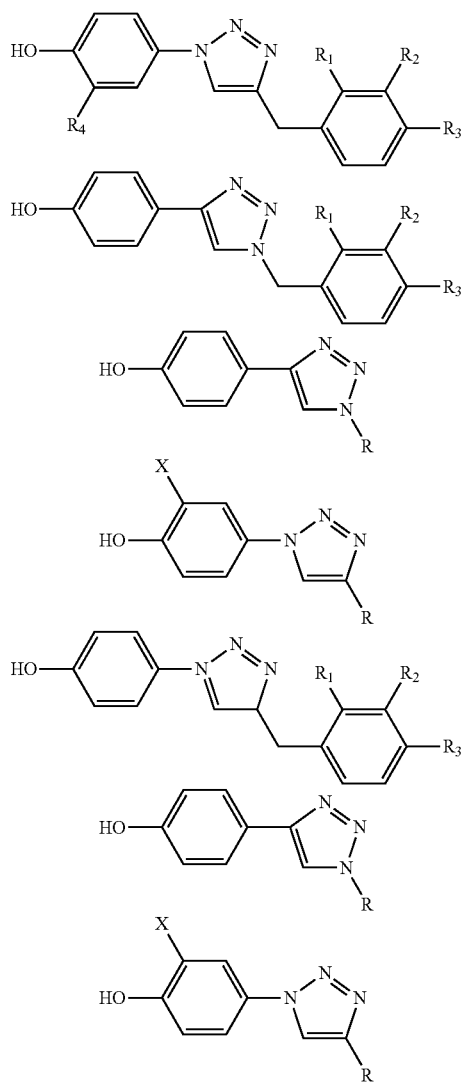

wherein R has the same definition as $R_6$ in formula (III) (most preferably, R is an optionally substituted $(CH_2)_j$-phenyl group, an optionally substituted $(CH_2)$m-heterocyclic (preferably heteroaryl) group), or an optionally substituted acyl group, an optionally substituted carbonyl phenyl group, or an optionally substituted carbonyl heteroaryl group), X is halo, and $R_1$, $R_2$, $R_3$, and $R_4$ are independently H, —OH, halogen, cyano, an optionally substituted $C_1$-$C_8$ alkyl, alkene or alkyne group, an optionally substituted acyl group, an optionally substituted $C_2$-$C_8$ ester or carboxyester group, an optionally substituted $C_1$-$C_{10}$ alkoxy group, an optionally substituted $C_2$-$C_8$ ether group, an optionally substituted $C_1$-$C_7$ amido or carboxamido group, or a $C_1$-$C_7$ urethane or urea group.

Other preferred compounds of formula (III) include:

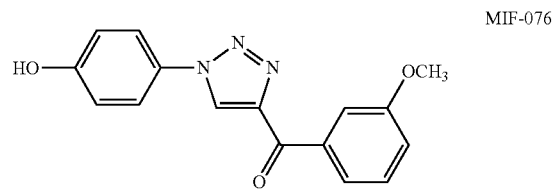 [SMILES: COc1cccc(C(=O)c2cn(-c3ccc(O)cc3)nn2)c1]

MIF-076

In another preferred embodiment of the compounds of chemical structure (III):

(1) $R^6$ is an optionally substituted $(CH_2)_j$-phenyl group, or an optionally substituted $(CH_2)_m$-heterocyclic group (preferably, an optionally substituted $(CH_2)_m$-heteroaryl) group; and (2) one of $R^{A1}$ and $R^{B1}$ is H and the other is an optionally substituted $(CH_2)_j$-phenyl group.

In still another preferred embodiment of the compounds of chemical structure (III), $R^6$ is (a) $(CH_2)_j$-phenyl group, which is optionally substituted with no more than three substituents selected from halogen (especially fluoro and chloro), $CH_3$, $CH_2CH_3$, $CF_3$, $CH_2OH$, $CH_2OCH_3$, $OCH_3$, and CN, or is (b) a $(CH_2)_m$-heteroaryl group, which is optionally substituted with no more than three substituents selected from halogen (especially fluoro and chloro), $CH_3$, $CH_2CH_3$, $CF_3$, $CH_2OH$, $CH_2OCH_3$, $OCH_3$, and CN; (2) $R^{A1}$ and $R^{B1}$ form a phenyl group which is optionally substituted with no more than three substituents selected from halogen (especially fluoro and chloro), $CH_3$, $CH_2CH_3$, $CF_3$, $CH_2OH$, $CH_2OCH_3$, $OCH_3$, and CN.

Also provided are compounds according to the formulae III-A, III-B, III-C, III-D, III-E, III-F, III-G, III-H and III-J:

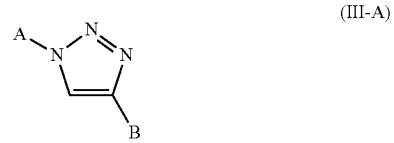

(III-A)

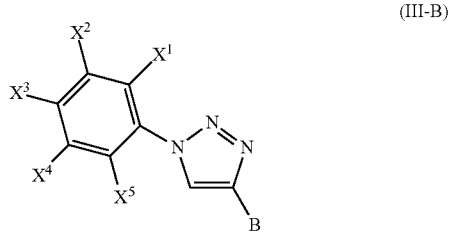

(III-B)

-continued (III-C) 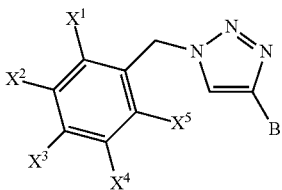

(III-D) 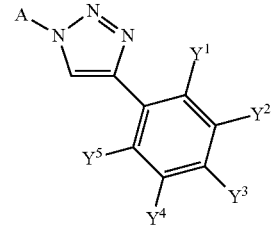

(III-E)

(III-F) 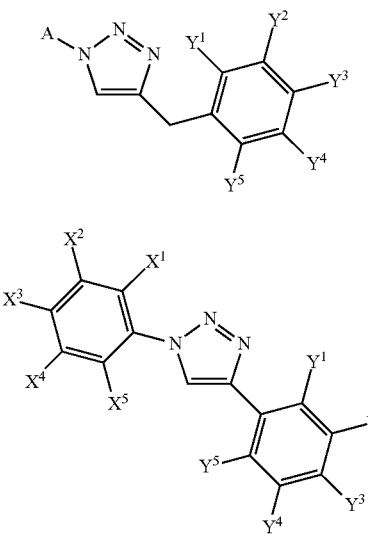

(III-G)

(III-H) 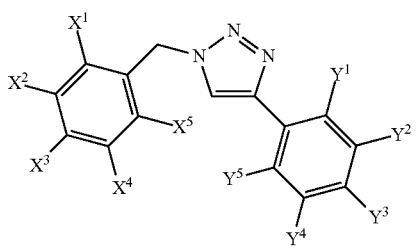

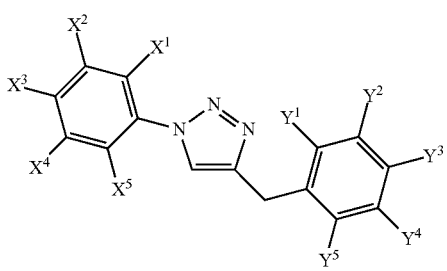

-continued (III-J) 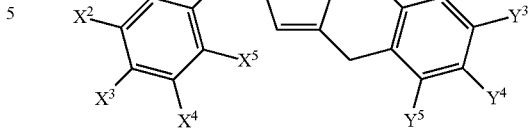

wherein

A is selected from the group consisting of —Ar$^1$ and —CH$_2$Ar$^1$;

B is selected from the group consisting of —Ar$^2$, —C(O)Ar$^2$ and —CH$_2$Ar$^2$;

Ar$^1$ is an unsubstituted or substituted aromatic ring which is phenyl, naphthyl, or a 5, 6, 8, 9, or 10-membered monocyclic or bicyclic heteroaryl group containing 0, 1, 2, 3 or 4 nitrogen atoms, 0, 1 or 2 oxygen atoms, and 0, 1 or 2 sulfur atoms as heteroatoms;

Ar$^2$ is an unsubstituted or substituted aromatic ring which is phenyl, naphthyl, or a 5, 6, 8, 9, or 10-membered monocyclic or bicyclic heteroaryl group containing 0, 1, 2, 3 or 4 nitrogen atoms, 0, 1 or 2 oxygen atoms, and 0, 1 or 2 sulfur atoms as heteroatoms;

wherein the optional substituents of Ar$^1$ and Ar$^2$ are each independently selected from —R$^a$; —OH; —OR$^a$; (C$_2$-C$_6$)alkenyl; (C$_2$-C$_6$)alkynyl; halogen; —C≡N; —NO$_2$; —C(=O)R$^b$; —C(=O)OR$^b$; —C(=O)NR$^c_2$; —C(=NR$^b$)NR$^c_2$; —OC(=O)(C$_1$-C$_6$)alkyl; —OC(=O)O(C$_1$-C$_6$)alkyl; —OC(=O)NR$^c_2$; —NR$^c_2$; —NR$^b$C(=O)R$^b$; —NR$^b$C(=O)O(C$_1$-C$_6$)alkyl; —NR$^b$C(=O)NR$^c_2$; —NR$^b$SO$_2$R$^b$; —SR$^b$; —S(O)R$^b$; —SO$_2$R$^b$; —OSO$_2$(C$_1$-C$_6$)alkyl; and —SO$_2$NR$^c_2$;

each X$^1$ is selected from —H; —R$^a$; —OH; —OR$^a$; (C$_2$-C$_6$)alkenyl; (C$_2$-C$_6$)alkynyl; halogen; —C≡N; —NO$_2$; —C(=O)R$^b$; —C(=O)OR$^b$; —C(=O)NR$^c_2$; —C(=NR$^b$)NR$^c_2$; —OC(=O)(C$_1$-C$_6$)alkyl; —OC(=O)O(C$_1$-C$_6$)alkyl; —OC(=O)NR$^c_2$; —NR$^c_2$; —NR$^b$C(=O)R$^b$; —NR$^b$C(=O)O(C$_1$-C$_6$)alkyl; —NR$^b$C(=O)NR$^c_2$; —NR$^b$SO$_2$R$^b$; —SR$^b$; —S(O)R$^b$; —SO$_2$R$^b$; —OSO$_2$(C$_1$-C$_6$)alkyl; and —SO$_2$NR$^c_2$;

each X$^2$ is selected from —H; —R$^a$; —OH; —OR$^a$; (C$_2$-C$_6$)alkenyl; (C$_2$-C$_6$)alkynyl; halogen; —C≡N; —NO$_2$; —C(=O)R$^b$; —C(=O)OR$^b$; —C(=O)NR$^c_2$; —C(=NR$^b$)NR$^c_2$; —OC(=O)(C$_1$-C$_6$)alkyl; C(=O)O(C$_1$-C$_6$)alkyl; —OC(=O)NR$^c_2$; —NR$^c_2$; —NR$^b$C(=O)R$^b$; —NR$^b$C(=O)O(C$_1$-C$_6$)alkyl; —NR$^b$C(=O)NR$^c_2$; —NR$^b$SO$_2$R$^b$; —SR$^b$; —S(O)R$^b$; —SO$_2$R$^b$; —OSO$_2$(C$_1$-C$_6$)alkyl; and —SO$_2$NR$^G_2$;

each X$^3$ is selected from —H; —R$^a$; —OH; —OR$^a$; (C$_2$-C$_6$)alkenyl; (C$_2$-C$_6$)alkynyl; halogen; —C≡N; —NO$_2$; —C(=O)R$^b$; —C(=O)OR$^b$; —C(=O)NR$^c_2$; —C(=NR$^b$)NR$^c_2$; —OC(=O)(C$_1$-C$_6$)alkyl; —OC(=O)O(C$_1$-C$_6$)alkyl; —OC(=O)NR$^c_2$; —NR$^c_2$; —NR$^b$C(=O)R$^b$; —NR$^b$C(=O)O(C$_1$-C$_6$)alkyl; —NR$^b$C(=O)NR$^c_2$; —NR$^b$SO$_2$R$^b$; —SR$^b$; —S(O)R$^b$; —SO$_2$R$^b$; —OSO$_2$(C$_1$-C$_6$)alkyl; and —SO$_2$NR$^G_2$;

each X$^4$ is selected from —H; —R$^a$; —OH; —OR$^a$; (C$_2$-C$_6$)alkenyl; (C$_2$-C$_6$)alkynyl; halogen; —C≡N; —NO$_2$; —C(=O)R$^b$; —C(=O)OR$^b$; —C(=O)NR$^c_2$; —C(=NR$^b$)NR$^c_2$; —CO(=O)(C$_1$-C$_6$)alkyl; —OC(=O)O(C$_1$-C$_6$)alkyl; —OC(=O)NR$^c_2$; —NR$^c_2$; —NR$^b$C(=O)R$^b$; —NR$^b$C(=O)O(C$_1$-C$_6$)alkyl; —NR$^b$C(=O)NR$^c_2$; —NR$^b$SO$_2$R$^b$; —SR$^b$; —S(O)R$^b$; —SO$_2$R$^b$; —OSO$_2$(C$_1$-C$_6$)alkyl; and —SO$_2$NR$^c_2$;

each $X^5$ is selected from —H; —$R^a$; —OH; —$OR^a$; $(C_2$-$C_6)$alkenyl; $(C_2$-$C_6)$alkynyl; halogen; —$NO_2$; —C(=O)$R^b$; —C(=O)$OR^b$; —C(=O)$NR^c{}_2$; —C(=N$R^b$)$NR^c{}_2$; —OC(=O)$(C_1$-$C_6)$alkyl; —OC(=O)O$(C_1$-$C_6)$alkyl; —OC(=O)$NR^c{}_2$; —$NR^c{}_2$; —$NR^b$C(=O)$R^b$; —$NR^b$C(=O)O$(C_1$-$C_6)$alkyl; —$NR^b$C(=O)$NR^c{}_2$; —$NR^b$SO$_2R^b$; —$SR^b$; —S(O)$R^b$; —SO$_2R^b$; —OSO$_2(C_1$-$C_6)$alkyl; and —SO$_2$NR$^c{}_2$;

each $Y^1$ is selected from —H; —$R^a$; —OH; —$OR^a$; $(C_2$-$C_6)$alkenyl; $(C_2$-$C_6)$alkynyl; halogen; —C≡N; —$NO_2$; —C(=O)$R^b$; —C(=O)$OR^b$; —C(=O)$NR^c{}_2$; —C(=N$R^b$)$NR^c{}_2$; —OC(=O)$(C_1$-$C_6)$alkyl; —OC(=O)O$(C_1$-$C_6)$alkyl; —OC(=O)$NR^c{}_2$; —$NR^c{}_2$; —$NR^b$C(=O)$R^b$; —$NR^b$C(=O)O$(C_1$-$C_6)$alkyl; —$NR^b$C(=O)$NR^c{}_2$; —$NR^b$SO$_2R^b$; —$SR^b$; —S(O)$R^b$; —SO$_2R^b$; —OSO$_2(C_1$-$C_6)$alkyl; and —SO$_2$NR$^c{}_2$;

each $Y^2$ is selected from —H; —$R^a$; —OH; —$OR^a$; $(C_2$-$C_6)$alkenyl; $(C_2$-$C_6)$alkynyl; halogen; —C≡N; —$NO_2$; —C(=O)$R^b$; —C(=O)$OR^b$; —C(=O)$NR^c{}_2$; —C(=N$R^b$)$NR^c{}_2$; —OC(=O)$(C_1$-$C_6)$alkyl; —OC(=O)O$(C_1$-$C_6)$alkyl; —OC(=O)$NR^c{}_2$; —$NR^c{}_2$; —$NR^b$C(=O)$R^b$; —$NR^b$C(=O)O$(C_1$-$C_6)$alkyl; —$NR^b$C(=O)$NR^c{}_2$; —$NR^b$SO$_2R^b$; —$SR^b$; —S(O)$R^b$; —SO$_2R^b$; —OSO$_2(C_1$-$C_6)$alkyl; and —SO$_2$NR$^c{}_2$;

each $Y^3$ is selected from —H; —$R^a$; —OH; —$OR^a$; $(C_2$-$C_6)$alkenyl; $(C_2$-$C_6)$alkynyl; halogen; —C≡N; —$NO_2$; —C(=O)$R^b$; —C(=O)$OR^b$; —C(=O)$NR^c{}_2$; —C(=N$R^b$)$NR^c{}_2$; —OC(=O)$(C_1$-$C_6)$alkyl; —OC(=O)O$(C_1$-$C_6)$alkyl; —OC(=O)$NR^c{}_2$; —$NR^c{}_2$; —$NR^b$C(=O)$R^b$; —$NR^b$C(=O)O$(C_1$-$C_6)$alkyl; —$NR^b$C(=O)$NR^c{}_2$; —$NR^b$SO$_2R^b$; —$SR^b$; —S(O)$R^b$; —SO$_2R^b$; —OSO$_2(C_1$-$C_6)$alkyl; and —SO$_2$NR$^c{}_2$;

each $Y^4$ is selected from —H; —$R^a$; —OH; —$OR^a$; $(C_2$-$C_6)$alkenyl; $(C_2$-$C_6)$alkynyl; halogen; —C≡N; —$NO_2$; —C(=O)$R^b$; —C(=O)$OR^b$; —C(=O)$NR^c{}_2$; —C(=N$R^b$)$NR^c{}_2$; —OC(=O)$(C_1$-$C_6)$alkyl; —OC(=O)O$(C_1$-$C_6)$alkyl; —OC(=O)$NR^c{}_2$; —$NR^c{}_2$; —$NR^b$C(=O)$R^b$; —$NR^b$C(=O)O$(C_1$-$C_6)$alkyl; —$NR^b$C(=O)$NR^c{}_2$; —$NR^b$SO$_2R^b$; —$SR^b$; —S(O)$R^b$; —SO$_2R^b$; —OSO$_2(C_1$-$C_6)$alkyl; and —SO$_2$NR$^c{}_2$; and each $Y^5$ is selected from —H; —$R^a$; —OH; —$OR^a$; $(C_2$-$C_6)$alkenyl; $(C_2$-$C_6)$alkynyl; halogen; —C≡N; —$NO_2$; —C(=O)$R^b$; —C(=O)$OR^b$; —C(=O)$NR^c{}_2$; —C(=N$R^b$)$NR^c{}_2$; —OC(=O)$(C_1$-$C_6)$alkyl; —OC(=O)O$(C_1$-$C_6)$alkyl; —OC(=O)$NR^c{}_2$; —$NR^c{}_2$; —$NR^b$C(=O)$R^b$; —$NR^b$C(=O)O$(C_1$-$C_6)$alkyl; —$NR^b$C(=O)$NR^c{}_2$; —$NR^b$SO$_2R^b$; —$SR^b$; —S(O)$R^b$; —SO$_2R^b$; —OSO$_2(C_1$-$C_6)$alkyl; and —SO$_2$NR$^c{}_2$;

each $R^a$ is independently unsubstituted $(C_1$-$C_6)$alkyl or $(C_1$-$C_6)$alkyl substituted with up to five halogen atoms and up to two substituents selected from the group consisting of —C≡N; —C(=O)$R^b$; —C(=O)$OR^b$; —C(=O)$NR^4{}_2$; —$OR^b$; —OC(=O)$(C_1$-$C_6)$alkyl; —OC(=O)O$(C_1$-$C_6)$alkyl; —OC(=O)$NR^c{}_2$; —$NR^c{}_2$; —$NR^b$C(=O)$R^b$; —$NR^b$C(=O)$NR^c{}_2$; —S$(C_1$-$C_6)$alkyl; —S(O)$(C_1$-$C_6)$alkyl; and —SO$_2(C_1$-$C_6)$alkyl;

each $R^b$ is independently hydrogen or $(C_1$-$C_6)$alkyl;

each $R^c$ is independently hydrogen; $(C_1$-$C_6)$alkyl; —$(C_2$-$C_6)$alkylene-$OR^b$; —$(C_1$-$C_6)$alkylene-C(=O)$OR^b$; —$(C_1$-$C_6)$alkylene-OC(=O)$R^b$; —$(C_2$-$C_6)$alkylene-$NR^b{}_2$; —$(C_1$-$C_6)$alkylene-C(=O)$NR^b{}_2$; —$(C_1$-$C_6)$alkylene-$NR^b$C(=O)$R^b$; —$(C_1$-$C_6)$alkylene-$NR^b$C(=O)$NR^b{}_2$; or, optionally, within any occurrence of $NR^c{}_2$, independently of any other occurrence of $NR^c{}_2$, the two $R^c$ groups in combination are —(CH$_2$)$_\alpha$— or —(CH$_2$)$_\beta$Q(CH$_2$)$_2$—;

each α is independently selected from the group consisting of 4, 5, and 6;

each β is independently selected from the group consisting of 2 and 3;

each Q is independently selected from the group consisting of O, S, $NR^b$; NC(=O)$R^b$; NSO$_2R^b$; N$(C_2$-$C_6)$alkylene-$OR^b$; N$(C_1$-$C_6)$alkylene-C(=O)$OR^b$; N$(C_1$-$C_6)$alkylene-OC(=O)$R^b$; N$(C_2$-$C_6)$alkylene-$NR^b{}_2$; N$(C_1$-$C_6)$alkylene-C(=O)$NR^b{}_2$; N$(C_1$-$C_6)$alkylene-$NR^b$C(=O)$R^b$; and N$(C_1$-$C_6)$alkylene-$NR^b$C(=O)$NR^b{}_2$.

or a pharmaceutically acceptable salt, enantiomer, solvate or polymorph thereof.

In some embodiments of such compounds A is —$Ar^1$. In other embodiments of such compounds A is —CH$_2Ar^1$.

In some embodiments of such compounds B is —$Ar^2$. In other embodiments of such compounds B is —CH$_2Ar^2$. In other embodiments of such compounds B is —C(O)$Ar^2$.

In some embodiments of such compounds A is —$Ar^1$ and B is —CH$_2Ar^2$. In other embodiments of such compounds A is —$Ar^1$ and B is —C(O)$Ar^2$. In other embodiments of such compounds A is —CH$_2Ar^1$ and B is —$Ar^2$ In some embodiments, $Ar^1$ is unsubstituted or substituted phenyl. In other embodiments, $Ar^1$ is unsubstituted or substituted naphthyl. In other embodiments, $Ar^1$ is an unsubstituted or substituted 5, 6, 8, 9, or 10-membered monocyclic or bicyclic heteroaryl group, for example 2-, 3-, or 4-pyridyl, 2-, 3-, 4-, 5-, 6-, 7, or 8-quinolyl, or 1-, 3-, 4-, 5-, 6-, 7, or 8-isoquinolyl.

In some embodiments, $Ar^2$ is unsubstituted or substituted phenyl. In other embodiments, $Ar^2$ is unsubstituted or substituted naphthyl. In other embodiments, $Ar^2$ is an unsubstituted or substituted 5, 6, 8, 9, or 10-membered monocyclic or bicyclic heteroaryl group, for example 2-, 3-, or 4-pyridyl, 2-, 3-, 4-, 5-, 6-, 7, or 8-quinolyl, or 1-, 3-, 4-, 5-, 6-, 7, or 8-isoquinolyl.

In some embodiments, the optional substituents of $Ar^1$ are independently selected from the group consisting of —$(C_1$-$C_6)$alkyl; —OH; —O$(C_1$-$C_6)$alkyl; $(C_2$-$C_6)$alkenyl; $(C_2$-$C_6)$alkynyl; halogen; —C≡N; —$NO_2$; —C(=O)$R^b$; —C(=O)$OR^b$; —C(=O)$NR^c{}_2$; —C(=N$R^b$)$NR^c{}_2$; —OC(=O)$(C_1$-$C_6)$alkyl; —OC(=O)O$(C_1$-$C_6)$alkyl; —OC(=O)$NR^c{}_2$; —$NR^c{}_2$; —$NR^b$C(=O)$R^b$; —$NR^b$C(=O)O$(C_1$-$C_6)$alkyl; —$NR^b$C(=O)$NR^c{}_2$; —$NR^b$SO$_2R^b$; —$SR^b$; —S(O)$R^b$; —SO$_2R^b$; —OSO$_2(C_1$-$C_6)$alkyl; and —SO$_2$NR$^c{}_2$. In some embodiments, the optional substituents of $Ar^1$ are independently selected from the group consisting of —$(C_1$-$C_6)$alkyl; —OH; —O$(C_1$-$C_6)$alkyl; $(C_2$-$C_6)$alkenyl; $(C_2$-$C_6)$alkynyl; halogen; —C≡N; —$NO_2$; —C(=O)$R^b$; —C(=O)$OR^b$; —C(=O)$NR^c{}_2$; —C(=N$R^b$)$NR^c{}_2$; —CO(=O)$(C_1$-$C_6)$alkyl; —OC(=O)O$(C_1$-$C_6)$alkyl; —OC(=O)$NR^c{}_2$; —$NR^c{}_2$; —$NR^b$C(=O)$R^b$; —$NR^b$C(=O)O$(C_1$-$C_6)$alkyl; —$NR^b$C(=O)$NR^c{}_2$; —$NR^b$SO$_2R^b$; —$SR^b$; —S(O)$R^b$; —SO$_2R^b$; —OSO$_2(C_1$-$C_6)$alkyl; and —SO$_2$NR$^c{}_2$. In some embodiments, the optional substituents of $Ar^1$ are independently selected from the group consisting of —$(C_1$-$C_6)$alkyl; —OH and —O$(C_1$-$C_6)$alkyl, —C(O)O$(C_1$-$C_6)$alkyl, for example —C(O)OMe or —C(O)OEt, and —C(O)OH. In some embodiments, the optional substituents of $Ar^1$ are independently selected from the group consisting of CH$_3$, CH$_2$CH$_3$, CHCH$_2$, C≡CH, NH$_2$, NHCH$_3$, N(CH$_3$)$_2$, OH, OCH$_3$, SH, SCH$_3$, F, Br and I.

In some embodiments, the optional substituents of $Ar^2$ are independently selected from the group consisting of —$(C_1$-$C_6)$alkyl; —OH; —O$(C_1$-$C_6)$alkyl; $(C_2$-$C_6)$alkenyl; $(C_2$-$C_6)$alkynyl; halogen; —CEN; —$NO_2$; —C(=O)$R^b$; —C(=O)$OR^b$; —C(=O)$NR^c{}_2$; —C(=N$R^b$)$NR^c{}_2$; —OC(=O)$(C_1$-$C_6)$alkyl; —OC(=O)O$(C_1$-$C_6)$alkyl; —OC(=O)$NR^c{}_2$; —$NR^c{}_2$; —$NR^b$C(=O)$R^b$; —$NR^b$C(=O)O$(C_1$-$C_6)$alkyl; —$NR^b$C(=O)$NR^c{}_2$; —$NR^b$SO$_2R^b$; —$SR^b$; —S(O)$R^b$;

—SO$_2$R$^b$; —OSO$_2$(C$_1$-C$_6$)alkyl; and —SO$_2$NR$^c_2$. In some embodiments, the optional substituents of Ar$^2$ are independently selected from the group consisting of —(C$_1$-C$_6$)alkyl; —OH; —O(C$_1$-C$_6$)alkyl; (C$_2$-C$_6$)alkenyl; (C$_2$-C$_6$)alkynyl; halogen; —C≡N; —NO$_2$; —C(=O)R$^b$; —C(=O)OR$^b$; —C(=O)NR$^c_2$; —C(=NR$^b$)NR$^c_2$; —OC(=O)(C$_1$-C$_6$)alkyl; —OC(=O)O(C$_1$-C$_6$)alkyl; —OC(=O)NR$^c_2$; —NR$^c_2$; —NR$^b$C(=O)R$^b$; —NR$^b$C(O)O(C$_1$-C$_6$)alkyl; —NR$^b$C(=O)NR$^c_2$; —NR$^b$SO$_2$R$^b$; —SR$^b$; —S(O)R$^b$; —SO$_2$R$^b$; —OSO$_2$(C$_1$-C$_6$)alkyl; and —SO$_2$NR$^c_2$. In some embodiments, the optional substituents of Ar$^2$ are independently selected from the group consisting of —(C$_1$-C$_6$)alkyl; —OH and —O(C$_1$-C$_6$)alkyl, —C(O)O(C$_1$-C$_6$)alkyl, for example —C(O)OMe or —C(O)OEt, and —C(O)OH. In some embodiments, the optional substituents of Ar$^2$ are independently selected from the group consisting of CH$_3$, CH$_2$CH$_3$, CHCH$_2$, NH$_2$, NHCH$_3$, N(CH$_3$)$_2$, OH, OCH$_3$, SH, SCH$_3$, F, Cl, Br and I.

In some embodiments any one or more of X$^1$, X$^2$, X$^3$, X$^4$, X$^5$, Y$^1$, Y$^2$, Y$^3$, Y$^4$ and Y$^5$ may be selected from the group consisting of —H; —(C$_1$-C$_6$)alkyl; —OH; —O(C$_1$-C$_6$)alkyl; (C$_2$-C$_6$)alkenyl; (C$_2$-C$_6$)alkynyl; halogen; —C≡N; —NO$_2$; —C(=O)R$^b$; —C(=O)OR$^b$; —C(=O)NR$^c_2$; —C(=NR$^b$)NR$^c_2$; —OC(=O)(C$_1$-C$_6$)alkyl; —OC(=O)O(C$_1$-C$_6$)alkyl; —OC(=O)NR$^c_2$; —NR$^c_2$; —NR$^b$C(=O)R$^b$; —NR$^b$C(=O)O(C$_1$-C$_6$)alkyl; —NR$^b$C(=O)NR$^c_2$; —NR$^b$SO$_2$R$^b$; —SR$^b$; —S(O)R$^b$; —SO$_2$R$^b$; —OSO$_2$(C$_1$-C$_6$)alkyl; and —SO$_2$NR$^c_2$. In some embodiments any one or more of X$^1$, X$^2$, X$^3$, X$^4$, X$^5$, Y$^1$, Y$^2$, Y$^3$, Y$^4$ and Y$^5$ may be selected from the group consisting of —H; —(C$_1$-C$_6$)alkyl; —OH; —O(C$_1$-C$_6$)alkyl; (C$_2$-C$_6$)alkenyl; (C$_2$-C$_6$)alkynyl; halogen; —C≡N; —NO$_2$; —C(=O)R$^b$; —C(=O)OR$^b$; —C(=O)NRO$_2$; —C(=NR$^b$)NR$^c_2$; —OC(=O)(C$_1$-C$_6$)alkyl; —OC(=O)O(C$_1$-C$_6$)alkyl; —OC(=O)NR$^c_2$; —NR$^c_2$; —NR$^b$C(=O)R$^b$; —NR$^b$C(=O)O(C$_1$-C$_6$)alkyl; —NR$^b$C(=O)NR$^c_2$; —NR$^b$SO$_2$R$^b$; —SR$^b$; —S(O)R$^b$; —SO$_2$R$^b$; —OSO$_2$(C$_1$-C$_6$)alkyl; and —SO$_2$Nle$_2$. In some embodiments any one or more of X$^1$, X$^2$, X$^3$, X$^4$, X$^5$, Y$^1$, Y$^2$, Y$^3$, Y$^4$ and Y$^5$ may be selected from the group consisting of —H; —(C$_1$-C$_6$)alkyl; —OH and —O(C$_1$-C$_6$)alkyl, —C(O)O(C$_1$-C$_6$)alkyl and —C(O)OH. In some embodiments any one or more of X$^1$, X$^2$, X$^3$, X$^4$, X$^5$, Y$^1$, Y$^2$, Y$^3$, Y$^4$ and Y$^5$ may be selected from the group consisting of —H; H, CH$_3$, CH$_2$CH$_3$, CHCH$_2$, C≡CH, NH$_2$, NHCH$_3$, N(CH$_3$)$_2$, OH, OCH$_3$, SH, SCH$_3$, F, Cl, Br and I.

In some embodiments, any one or more of X$^1$, X$^2$, X$^3$, X$^4$, X$^5$, Y$^1$, Y$^2$, Y$^3$, Y$^4$ and Y$^5$ may be H. In some embodiments, any one or more of X$^1$, X$^2$, X$^3$, X$^4$, X$^5$, Y$^1$, Y$^2$, Y$^3$, Y$^4$ and Y$^5$ may be other than H. In some embodiments X$^1$ is H. In some embodiments X$^2$ is H. In some embodiments X$^3$ is H. In some embodiments X$^4$ is H. In some embodiments X$^5$ is H. In some embodiments, four of X$^1$, X$^2$, X$^3$, X$^4$ and X$^5$, for example X$^1$, X$^2$, X$^4$ and X$^5$ are H. In some embodiments Y$^1$ is H. In some embodiments Y$^2$ is H. In some embodiments Y$^3$ is H. In some embodiments Y$^4$ is H. In some embodiments Y$^5$ is H. In some embodiments, four of Y$^1$, Y$^2$, Y$^3$, Y$^4$ and Y$^5$, for example Y$^1$, Y$^2$, Y$^4$ and Y$^5$ are H. In some embodiments, three of Y$^1$, Y$^2$, Y$^3$, Y$^4$ and Y$^5$ for example Y$^1$, Y$^2$ and Y$^5$ are H.

In some embodiments X$^3$ is —O(C$_1$-C$_6$)alkyl or —OH. In some embodiments, X$^3$ is —OH. These include embodiments in which X$^1$, X$^2$, X$^4$ and X$^5$ are H. These also include embodiments in which X$^1$, X$^2$ and X$^5$ are H but X$^4$ is other than H, for example halogen, —OH, or —O(C$_1$-C$_6$)alkyl. In some embodiments Y$^3$ is —O(C$_1$-C$_6$)alkyl or —OH. In some embodiments, Y$^3$ is —OH. These include embodiments in which Y$^1$, Y$^2$, Y$^4$ and Y$^5$ are H. These also include embodiments in which Y$^1$, Y$^2$ and Y$^5$ are H but Y$^4$ is other than H, for example halogen, —OH, or —O(C$_1$-C$_6$)alkyl.

Other preferred compounds according to the present invention include the following:

17

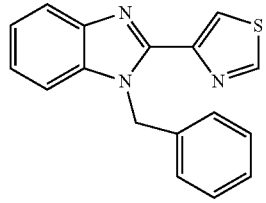

18

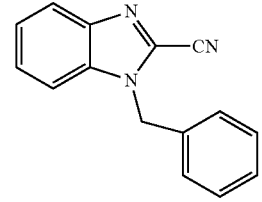

19

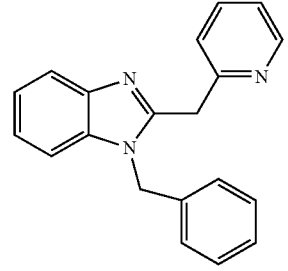

20

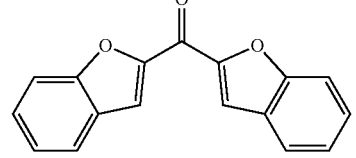

21

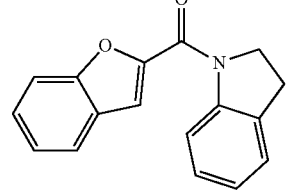

22

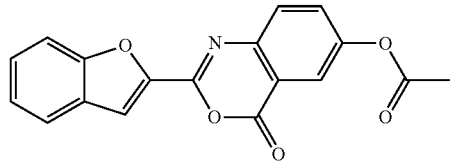

23

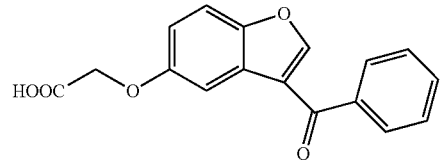

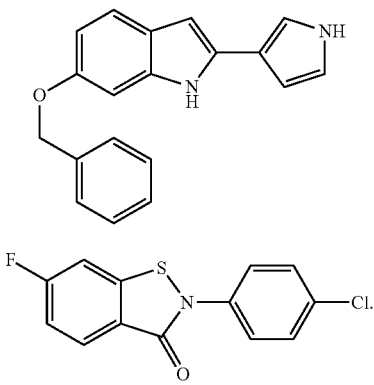

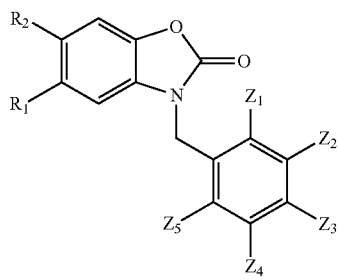

In alternative embodiments according to the present invention, the present invention is directed to a compound according to the chemical structure B:

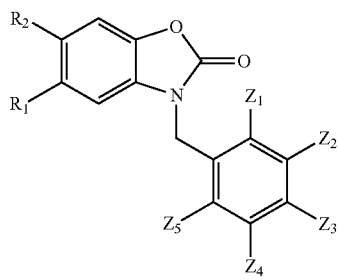

Where $R_1$ and $R_2$ are each independently selected from H, OH, CN, $NO_2$, halogen (F, Cl, Br, I, preferably Br, Cl or F), $C_1$-$C_4$ alkyl which is optionally substituted with at least one hydroxyl (from 1 to 3 hydroxyls) or at least one and preferably at least three halogens, preferably F, or a —$(CH_2)_jOR^a$, —$(CH_2)_jC(O)R^a$ or —$(CH_2)_jOC(O)R^a$ group, where $R^a$ is H, a $C_1$-$C_3$ alkyl group which is optionally substituted with at least one hydroxyl group (1 to 3) or at least one halogen, preferably at least three halogen groups, preferably F and j is 0, 1, 2 or 3;

$Z_1$, $Z_2$, $Z_3$, $Z_4$ and $Z_5$ are each independently H, $C_1$-$C_3$ alkyl group which is optionally substituted with at least one hydroxyl group (from 1 to 3) or at least one halogen, preferably at least three halogen groups, preferably F, or a —$(CH_2)_jOR^a$, —$(CH_2)_jC(O)R^a$ or —$(CH_2)_jOC(O)R^a$ group, where $R^a$ is H, a $C_1$-$C_3$ alkyl group which is optionally substituted with at least one hydroxyl group (1 to 3) or at least one halogen, preferably at least three halogen groups, preferably F; and j is 0, 1, 2 or 3, or a pharmaceutically acceptable salt, enantiomer, solvate or polymorph thereof.

In preferred embodiments, $Z_4$ and $Z_5$ are both H. In alternative preferred embodiments, $R_1$ is H, $CH_3$, $OCH_3$, F or OH; $R_2$ is H, $CH_3$ or OH; $Z_1$ is H or $OCH_3$; $Z_2$ is H, OH or $OCH_3$; $Z_3$ is H or $OCH_3$; $Z_4$ is H and $Z_5$ is H.

Preferred compounds include a compound where $R_1$ is $CH_3$, $R_2$ is H, $Z_1$ is $OCH_3$, $Z_2$ is H, $Z_3$ is H, $Z_4$ is H and $Z_5$ is H; a compound where $R_1$ is $CH_3$, $R_2$ is H, $Z_1$ is H, $Z_2$ is H, $Z_3$ is H, $Z_4$ is H and $Z_5$ is H; a compound where $R_1$ is H, $R_2$ is OH, $Z_1$ is H, $Z_2$ is H, $Z_3$ is $OCH_3$, $Z_4$ is H and $Z_5$ is H; a compound where $R_1$ is F, $R_2$ is H, $Z_1$ is H, $Z_2$ is H, $Z_3$ is H, $Z_4$ is H and $Z_5$ is H; a compound where $R_1$ is $CH_3$, $R_2$ is H, $Z_1$ is H, $Z_2$ is OH, $Z_3$ is H, $Z_4$ is H and $Z_5$ is H; and a compound where $R_1$ is OH, $R_2$ is H, $Z_1$ is $OCH_3$, $Z_2$ is $OCH_3$, $Z_3$ is H, $Z_4$ is H and $Z_5$ is H.

Further embodiments relate to compounds according to the chemical structure:

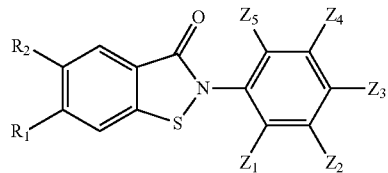

Where $R_1$ and $R_2$ are each independently selected from H, OH, CN, $NO_2$, halogen (F, Cl, Br, I, preferably Br, Cl or F), $C_1$-$C_4$ alkyl which is optionally substituted with at least one hydroxyl (from 1 to 3 hydroxyls) or at least one and preferably at least three halogens, preferably F, or a —$(CH_2)_jOR^a$, —$(CH_2)_jC(O)R^a$ or —$(CH_2)_jOC(O)R^a$ group, where $R^a$ is H, a $C_1$-$C_3$ alkyl group which is optionally substituted with at least one hydroxyl group (1 to 3) or at least one halogen, preferably at least three halogen groups, preferably F; and j is 0, 1, 2 or 3;

$Z_1$, $Z_2$, $Z_3$, $Z_4$ and $Z_5$ are each independently H, $C_1$-$C_3$ alkyl group which is optionally substituted with at least one hydroxyl group (from 1 to 3) or at least one halogen, preferably at least three halogen groups, preferably F, or a —$(CH_2)_jOR^a$, —$(CH_2)_jC(O)R^a$ or —$(CH_2)_j$—$OC(O)R^a$ group, where $R^a$ is H, a $C_1$-$C_3$ alkyl group which is optionally substituted with at least one hydroxyl group (1 to 3) or at least one halogen, preferably at least three halogen groups, preferably F; and j is 0, 1, 2 or 3, or a pharmaceutically acceptable salt, enantiomer, solvate or polymorph thereof.

Preferred compounds include a compound where $R_1$ is H, $R_2$ is F, $Z_1$ is H, $Z_2$ is H, $Z_3$ is $C_1$, $Z_4$ is H and $Z_5$ is H; a compound where $R_1$ is F, $R_2$ is H, $Z_1$ is H, $Z_2$ is H, $Z_3$ is $C_1$, $Z_4$ is H and $Z_5$ is H; a compound where $R_1$ is F, $R_2$ is H, $Z_1$ is H, $Z_2$ is $CH_2OAc$, $Z_3$ is H, $Z_4$ is H and $Z_5$ is H; and a compound where $R_1$ is CN, $R_2$ is H, $Z_1$ is H, $Z_2$ is H, $Z_3$ is $C_1$, $Z_4$ is H and $Z_5$ is H.

In still another aspect, the invention provides compounds of the formula (IV)(A) and (IV)(B):

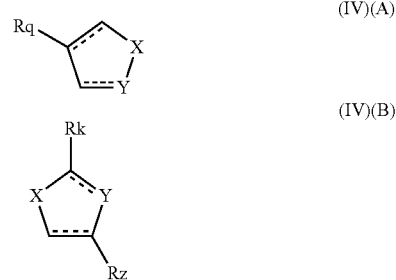

wherein X is O or N—$R^{XN1}$;
Y is O or N—$R^{YN1}$;
provided that X and Y are not both O;
$R^{XN1}$ and $R^{YN1}$, j, and m are as defined for compounds of formula (II)(A);

Rq is an optionally substituted $(CH_2)_j$-phenyl group, an optionally substituted $(CH_2)_m$-heterocyclic (preferably heteroaryl) group, or an optionally substituted acyl group, an optionally substituted carbonyl phenyl group, or an optionally substituted carbonyl heteroaryl group;

$R_k$, together with the carbon to which it is bound, forms a carbonyl group, or $R_k$ is H, halogen, cyano, an optionally substituted $C_1$-$C_8$ alkyl, alkene or alkyne group, an optionally substituted acyl group, an optionally substituted carbonyl phenyl group, an optionally substituted carbonyl heteroaryl group, an optionally substituted $C_2$-$C_8$ ester or carboxyester group, an optionally substituted $C_1$-$C_{10}$ alkoxy group, an optionally substituted $C_2$-$C_8$ ether group, an optionally substituted $C_1$-$C_7$ amido or carboxamido group, a $C_1$-$C_7$ urethane or urea group, an optionally substituted $(CH_2)_j$-phenyl group, or an optionally substituted $(CH_2)_m$-heterocyclic (preferably heteroaryl) group; and $R_z$ is H, halogen, cyano, an optionally substituted $C_1$-$C_8$ alkyl, alkene or alkyne group, an optionally substituted acyl group, an optionally substituted carbonyl phenyl group, an optionally substituted carbonyl heteroaryl group, an optionally substituted $C_2$-$C_8$ ester or carboxyester group, an optionally substituted $C_1$-$C_{10}$ alkoxy group, an optionally substituted $C_2$-$C_8$ ether group, an optionally substituted $C_1$-$C_7$ amido or carboxamido group, a $C_1$-$C_7$ urethane or urea group, an optionally substituted $(CH_2)_j$-phenyl group, or an optionally substituted $(CH_2)_m$-heterocyclic (preferably heteroaryl) group or a pharmaceutically acceptable salt, stereoisomer (e.g. enantiomer or diastereomer), solvate or polymorph thereof.

In preferred aspects of compounds of formula (IV)(A), X is N—$R^{XN1}$, $R^{XN1}$ is H, an optionally substituted $C_1$-$C_8$ alkyl, alkene or alkyne group, or an optionally substituted $C_1$-$C_8$ acyl group, Y is N—$R^{YN1}$, $R^{YN1}$ is absent, and Rq is an optionally substituted $(CH_2)_j$-phenyl group.

In preferred aspects of compounds of formula (IV)(B), X is N—$R^{XN1}$, $R^{XN1}$ is an optionally substituted $(CH_2)_j$-phenyl group, $R_k$, together with the carbon to which it is bound, forms a carbonyl group, Y is O, and $R_z$ is an optionally substituted $(CH_2)_j$-phenyl group.

Preferred examples of the compounds of the formula (IV)(A) and (IV)(B) include:

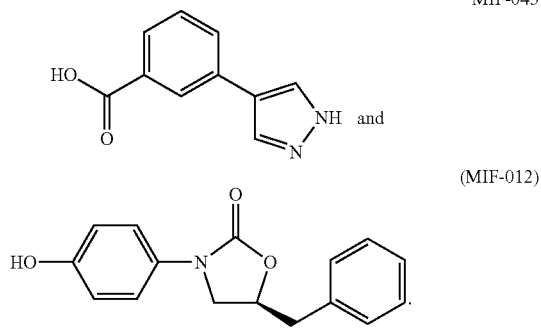

MIF-045

(MIF-012)

In another embodiment according to the present invention, pharmaceutical compositions comprise an effective amount of one or more compounds as described above, optionally in combination with a pharmaceutically acceptable carrier, excipient or additive. Pharmaceutical compositions may also include, in addition to the present compounds, at least one additional compound, including another agent which modulates MIF.

In another embodiment, the present application is directed to the modulation (enhancement or inhibition) of the action of MIF in a patient wherein said method comprises administering an effective amount of a compound according to the present invention in combination with a pharmaceutically acceptable carrier, additive or excipient.

In yet another embodiment, the present application is directed to the treatment of a "disease associated with high MIF expression" or a "disease associated with low MIF expression", as defined hereinafter, the method comprising administering to a patient in need thereof an effective amount of a pharmaceutical composition comprising any one or more of the compounds previously described above, optionally in combination (coadministered) with another active agent, preferably another agent which modulates levels of MIF expression as otherwise disclosed herein.

Pharmaceutical dosage forms comprising the aforementioned novel compounds are also provided by the invention.

DETAILED DESCRIPTION OF THE INVENTION

The following terms shall be used to describe the present invention. In cases where a term is not specifically defined herein, the term shall be given a common meaning used by those of ordinary skill in the art consistent with the use of that term within the context of describing the present invention.

As used herein and in the appended claims, the singular forms "a," "an," and "the" include plural reference unless the context clearly dictates otherwise. Thus, for example, a reference to "a compound" or other element of the present invention includes a plurality (for example, two or more elements) of such elements, and so forth. Under no circumstances is the patent to be interpreted to be limited to the specific examples or embodiments or methods specifically disclosed herein.

The term "compound", as used herein, unless otherwise indicated, refers to any specific chemical compound disclosed herein and includes tautomers, regioisomers, geometric isomers, and where applicable, optical isomers thereof, as well as pharmaceutically acceptable salts thereof. Within its use in context, the term compound generally refers to a single compound, but also may include other compounds such as stereoisomers, regioisomers and/or optical isomers (including racemic mixtures) as well as specific enantiomers or enantiomerically enriched mixtures of disclosed compounds.

The symbol ------ is used in chemical compounds according to the present invention to signify that a bond between atoms is a single bond or double bond according to the context of the bond's use in the compound, which depends on the atoms (and substituents) used in defining the present compounds. Thus, where a carbon (or other) atom is used and the context of the use of the atom calls for a double bond or single bond to link that atom with an adjacent atom in order to maintain the appropriate valence of the atoms used, then that bond is considered a double bond or a single bond.

The term "patient" or "subject" is used throughout the specification within context to describe an animal, generally a mammal and preferably a human, to whom treatment, including prophylactic treatment, with the compositions according to the present invention is provided. For treatment of those infections, conditions or disease states which are specific for a specific animal such as a human patient, the term patient refers to that specific animal.

The term "effective" is used herein, unless otherwise indicated, to describe an amount of a compound or composition which, in context, is used to produce or effect an intended result, whether that result relates to the treatment of a disorder or condition associated with high or low MIF expression or alternatively, is used to produce another compound, agent or composition. This term subsumes all other effective amount or effective concentration terms which are otherwise described in the present application.

"Hydrocarbon" or "hydrocarbyl" refers to any monovalent (or divalent in the case of alkylene groups) radical containing carbon and hydrogen, which may be straight, branch-chained or cyclic in nature. Hydrocarbons include linear, branched and cyclic hydrocarbons, including alkyl groups, alkylene groups, saturated and unsaturated hydrocarbon groups, including aromatic groups both substituted and unsubstituted, alkene groups (containing double bonds between two carbon atoms) and alkyne groups (containing triple bonds between two carbon atoms). In certain instances, the terms substituted alkyl and alkylene are sometimes synonymous.

"Alkyl" refers to a fully saturated monovalent radical containing carbon and hydrogen, and which may be cyclic, branched or a straight chain. Examples of alkyl groups are methyl, ethyl, n-butyl, n-hexyl, n-heptyl, n-octyl, n-nonyl, n-decyl, isopropyl, 2-methylpropyl, cyclopropyl, cyclopropylmethyl, cyclobutyl, cyclopentyl, cyclopentylethyl, cyclohexylethyl and cyclohexyl. Preferred alkyl groups are $C_1$-$C_6$ alkyl groups.

"Alkylene" refers to a fully saturated hydrocarbon which is divalent (may be linear, branched or cyclic) and which is optionally substituted. Preferred alkylene groups are $C_1$-$C_6$ alkylene groups. Other terms used to indicate substituent groups in compounds according to the present invention are as conventionally used in the art.

"Aryl" or "aromatic", in context, refers to a substituted or unsubstituted monovalent aromatic radical having a single ring (e.g., benzene or phenyl) or multiple condensed rings (e.g., naphthyl, anthracenyl, phenanthryl) and can be can be bound to the compound according to the present invention at any position on the ring(s) or as otherwise indicated in the chemical structure presented. Other examples of aryl groups, in context, may include heterocyclic aromatic ring systems "heteroaryl" groups having one or more nitrogen, oxygen, or sulfur atoms in the ring (moncyclic) such as imidazole, furyl, pyrrole, furanyl, thiene, thiazole, pyridine, pyrimidine, pyrazine, triazole, oxazole, indole or fused ring systems (bicyclic, tricyclic), among others, which may be substituted or unsubstituted as otherwise described herein.

The term "cyclic" shall refer to an optionally substituted carbocyclic or heterocyclic group, preferably a 5- or 6-membered ring or fused rings (two or three rings) preferably containing from 8 to 14 atoms. A heterocyclic ring or group shall contain at least one monocyclic ring containing between 3 and 7 atoms of which up to four of those atoms are other than carbon and are selected from nitrogen, sulfur and oxygen. Carbocyclic and heterocyclic rings according to the present invention may be unsaturated or saturated. Preferred carbocyclic groups are unsaturated, and include phenyl groups, among other groups. Preferred heterocyclic groups are heteroaryl or heteroaromatic.

The term "heterocyclic group" as used throughout the present specification refers to an aromatic or non-aromatic cyclic group having 3 to 14 atoms, preferably 5 to 14 atoms forming the cyclic ring(s) and including at least one hetero atom such as nitrogen, sulfur or oxygen among the atoms forming the cyclic ring, which is an aromatic heterocyclic group (also, "heteroaryl" or "heteroaromatic") in the former case and a "non-aromatic heterocyclic group" in the latter case. Specific examples of the heterocyclic group therefore include specific examples of the aromatic heterocyclic group and specific examples of the non-aromatic heterocyclic group, both of which groups fall under the rubric "heterocyclic group" as otherwise described herein. Among the heterocyclic groups which may be mentioned for use in the present invention within context include nitrogen-containing aromatic heterocycles such as pyrrole, pyridine, pyridone, pyridazine, pyrimidine, pyrazine, pyrazole, imidazole, triazole, tetrazole, indole, isoindole, indolizine, purine, indazole, quinoline, isoquinoline, quinolizine, phthalazine, naphthyridine, quinoxaline, quinazoline, cinnoline, pteridine, imidazopyridine, imidazotriazine, pyrazinopyridazine, acridine, phenanthridine, carbazole, carbazoline, perimidine, phenanthroline, phenacene, oxadiazole, benzimidazole, pyrrolopyridine, pyrrolopyrimidine and pyridopyrimidine; sulfur-containing aromatic heterocycles such as thiophene and benzothiophene; oxygen-containing aromatic heterocycles such as furan, pyran, cyclopentapyran, benzofuran and isobenzofuran; and aromatic heterocycles comprising 2 or more hetero atoms selected from among nitrogen, sulfur and oxygen, such as thiazole, thiadiazole, isothiazole, benzoxazole, benzothiazole, benzothiadiazole, phenothiazine, isoxazole, furazan, phenoxazine, pyrazoloxazole, imidazothiazole, thienofuran, furopyrrole, pyridoxazine, furopyridine, furopyrimidine, thienopyrimidine and oxazole. As examples of the "5- to 14-membered aromatic heterocyclic group" there may be mentioned preferably, pyridine, triazine, pyridone, pyrimidine, imidazole, indole, quinoline, isoquinoline, quinolizine, phthalazine, naphthyridine, quinazoline, cinnoline, acridine, phenacene, thiophene, benzothiophene, furan, pyran, benzofuran, thiazole, benzthiazole, phenothiazine, pyrrolopyrimidine, furopyridine and thienopyrimidine, more preferably pyridine, thiophene, benzothiophene, thiazole, benzothiazole, quinoline, quinazoline, cinnoline, pyrrolopyrimidine, pyrimidine, furopyridine and thienopyrimidine. The term "heterocyclic group" shall generally refer to 3 to 14-membered heterocyclic groups and all subsets of heterocyclic groups (including non-heteroaromatic or heteroaromatic) subsumed under the definition of heterocyclic group.

Among the heterocyclic groups for use in the present invention may preferably include pyrrolidine, piperidine, morpholine, pyrrole, pyridine, pyridone, pyrimidine, imidazole, indole, quinoline, isoquinoline, quinolizine, phthalazine, naphthyridine, quinazoline, cinnoline, acridine, phenacene, thiophene, benzothiophene, furan, pyran, benzofuran, thiazole, benzothiazole, phenothiazine and carbostyryl, alternatively, pyrrolidine, piperidine, morpholine, pyrrole, pyridine, pyridine-N-oxide, thiophene, benzothiophene, thiazole, benzothiazole, quinoline, quinazoline, cinnoline, benzofuran, indole, and carbostyryl, and further alternatively, thiazole, quinoline, quinazoline, cinnoline and carbostyryl, among others.

Among the bicyclic or tricyclic heterocyclic groups which may be used in the present invention include indole or 2,3-dihydroindole, isoindole, indolizine, purine, indazole, quinoline, isoquinoline, quinolizine, phthalazine, naphthyridine, quinoxaline, quinazoline, cinnoline, pteridine, imidazopyridine, imidazotriazine, pyrazinopyridazine, acridine, phenanthridine, carbazole, carbazoline, perimidine, phenanthroline, phenacene, benzimidazole, pyrrolopyridine, pyrrolopyrimidine and pyridopyrimidine; sulfur-containing aromatic heterocycles such as thiophene and benzothiophene; oxygen-containing aromatic heterocycles such as cyclopentapyran, benzofuran and isobenzofuran; and aromatic heterocycles comprising 2 or more hetero atoms selected from among nitrogen, sulfur and oxygen, such as benzoxazole, benzothiazole, benzothiadiazole, phenothiazine, benzofurazan, phenoxazine, pyrazoloxazole, imidazothiazole, thienofuran, furopyrrole, pyridoxazine, furopyridine, furopyrimidine and thienopyrimidine, among others.

The term "substituted" shall mean substituted at a carbon (or nitrogen) position within context, hydroxyl, carboxyl, cyano (CEN), nitro ($NO_2$), halogen (preferably, 1, 2 or 3 halogens, especially on an alkyl, especially a methyl group such as a trifluoromethyl), thiol, an optionally substituted alkyl, alkene or alkyne group (preferably, $C_1$-$C_6$, $C_2$-$C_6$, more preferably $C_1$-$C_3$, $C_2$-$C_3$), optionally substituted aryl (especially optionally substituted phenyl or benzyl), optionally substituted heterocyclic (especially optionally substituted heteroaryl for example, pyridinyl (2-, 3-, 4-), pyrimidinyl, thienyl (2- or 3-), furanyl (2- or 3-), alkoxy (preferably, $C_1$-$C_6$ alkyl or aryl), optionally substituted $C_2$-$C_{12}$ ether (preferably, $C_2$-$C_{10}$ alkyl ether, alkenylether, alkynyl ether or aryl ether, including phenyl or benzyl ether), acyl (preferably $C_2$-$C_8$ acyl which may include an aryl substituted acyl), optionally substituted ester (preferably, $C_1$-$C_6$ alkyl or aryl) including alkylene, alkenyl or alkynyl ester (alkylene attachment to compound), carboxyester (carbonyl attachment to compound) or hydroxyester (oxygen attachment to compound), thioether (preferably, $C_1$-$C_7$ alkyl or aryl), thioester (preferably, $C_1$-$C_7$ alkyl or aryl), amine (including a five- or six-membered cyclic alkylene amine, including an optionally substituted $C_1$-$C_6$ alkyl amine (e.g., monoalkanolamine) or an optionally substituted $C_1$-$C_6$ dialkyl amine (e.g. dialkanolamine), alkanol (preferably, $C_1$-$C_6$ alkyl or aryl), or alkanoic acid (preferably, $C_1$-$C_6$ alkyl or aryl), optionally substituted carboxyamide (carbonyl attached to the carbon atom with one or two substituents on the amine group—preferably H or an optionally substituted $C_1$-$C_6$ alkyl group), amido group (amine group with H or $C_1$-$C_3$ alkyl group attached to the carbon atom with a single group, preferably H or an optionally substituted $C_1$-$C_6$ alkyl group on the keto group) or an optionally substituted urethane group (with either the amine or the O-carboxy group attached to a carbon atom to which the urethane is a substituent—the amine group being substituted with one or two H or one or two $C_1$-$C_6$ alkyl groups), —O-alkyl aryl, —O-alkenyl aryl, —O-alkynyl aryl, —O-alkyl heteroaryl, —O-alkenyl heteroaryl, and —O-alkynyl heteroaryl. Preferably, the term "substituted" shall mean within the context of its use alkyl, alkoxy, halogen, hydroxyl, carboxylic acid, cyano, ether, ester, acyl, nitro, amine (including mono- or di-alkyl substituted amines) and amide, as otherwise described above. Any substitutable position in a compound according to the present invention may be substituted in the present invention. Preferably no more than 5, more preferably no more than 3 substituents are present on a single ring or ring system. Preferably, the term "unsubstituted" shall mean substituted with one or more H atoms. It is noted that in describing a substituent, all stable permutations of the substituent are intended.

Preferred substituents for use in the present invention include, for example, F, Cl, CN, $NO_2$, $NH_2$, $NHCH_3$, $N(CH_3)_2$, $CH_3$, $CH_2OH$, COOH, $CH_2CH_3$, $CH_2OCH_3$, $CF_3$, $COCH_3$, $CO_2CH_3$, $CH_2CO_2CH_3$, optionally substituted naphthyl (including 1-naphthyl), thienyl, optionally substituted furanyl (especially $CH_2OCH_2$-furanyl), optionally substituted 2- or 3-pyridyl (especially $CH_2$-pyridyl or $CH_2OCH_2$-pyridyl), optionally substituted isoquinoline (especially 4-isoquinoline), optionally substituted pyrimidyl and optionally substituted phenyl, including benzyl ($CH_2OCH_2$-phenyl).

As used herein, the term "MIF" refers to macrophage migration inhibitory factor or active fragments thereof. Accession number EMBL Z23063 describes the nucleic acid sequence encoding human MIF (Bernhagen et al., *Biochemistry* 33:14144-14155 (1994)). An active fragment of MIF may comprise a fragment or a portion of the MIF protein encoding the tautomerase enzymatic activity of MIF, or a fragment that is capable of binding CD74.

As used herein a "MIF agonist" refers to any agent that mimics, activates, stimulates, potentiates or increases the biological activity of MIF. A MIF agonist may be MIF or an agent that mimics MIF (such as a small molecule); an agent that increases or enhances the expression of MIF, CD74 or CD44; an agent that enhances the binding of MIF to CD74; an agent than enhances the interaction between CD74 and CD44 (including, without limitation, a bivalent agent).

As used herein, the "biological function of MIF" refers to the ability of MIF to carry out one or more of the biological functions of MIF including, without limitation, sustaining immune cell survival or activation, promoting cytokine promotion, down-regulating CCR5, binding to CD74, activating MAP kinase signaling (e.g., ERK1/2, JNK, and SAPK MAP kinase signaling), inhibiting p53, acting as a tautomerase, and/or acting as a thiol reductase.

As used herein a "MIF antagonist" refers to any agent that attenuates, inhibits, opposes, counteracts, or decreases the biological activity of MIF. A MIF antagonist may be an agent that inhibits or neutralizes MIF activity (including, without limitation, small molecules and anti-MIF antibodies); an agent that inhibits or decreases the expression of MIF (including, without limitation, an antisense molecule); an agent that inhibits or decreases the expression of the CD44 receptor (including, without limitation, an antisense molecule or an RNAi molecule); an agent that prevents the binding of MIF to CD74 (including, without limitation, an anti-CD74 antibody or an anti-MIF antibody or a fragment thereof); an agent that prevents the interaction between CD74 and CD44 (such as an anti-CD74 antibody or an anti-CD44 antibody or a fragment thereof); or an agent that prevents the interaction between CD74 and CD44. Examples of such molecules are fragments of CD74 and CD44, such as soluble fragments of such receptors. Examples of MIF antagonists have been disclosed previously, see, e.g., U.S. Pat. No. 6,774,227, Bernhagen et al., *Nature* 365, 756-759 (1993), Senter et al., *Proc Natl Acad Sci USA* 99:144-149 (2002); Dios et al., *J. Med. Chem.* 45:2410-2416 (2002); Lubetsky et al., *J Biol Chem* 277: 24976-24982 (2002), which are hereby incorporated by reference.

"Modulate levels of MIF expression" means to increase or decrease levels of MIF expression.

As used herein, the term "treating" refers to preventing, slowing, delaying, stopping or reversing the progression of a disease and/or condition.

Methods of Treating Diseases Associated with High or Low MIF Expression

In certain embodiments, the invention features methods of treating diseases associated with high or low MIF expression comprising administering to a subject in need thereof a therapeutically effective amount of a MIF agonist or a MIF antagonist. In one embodiment, the invention comprises administering to a subject having, or at risk of developing, a disease associated with high MIF expression a therapeutically effective amount of a MIF antagonist. In another embodiment, the invention comprises administering to a subject having, or at risk of developing, a disease associated with low MIF expression a therapeutically effective amount of a MIF agonist.

As described further hereinafter, diseases associated with high MIF expression include, without limitation, diseases caused by infection by a protozoan (for example malaria) fungus, bacteria and viruses, including flavivirus, such as West Nile, Dengue, Japanese encephalitis, St Louis encephalitis, or equine encepahalitis viruses; anemia of chronic disease; asthma and autism spectrum disorder (ASD).

As described further hereinafter, diseases associated with low MIF expression include, without limitation, any infection and the diseases caused by infections. In one embodiment, the infection is an acute infection. In one embodiment, the infection is a bacterial infection. In another embodiment, the infection is a viral infection. In another embodiment, the infection is a fungal infection. In one embodiment, the disease associated with low MIF expression is sepsis. In another embodiment, the disease associated with low MIF expression is an infection that leads to a respiratory disease (or a respiratory disease resulting from an infection), including without limitation, infections and diseases caused by gram positive and gram negative bacteria, mycobacteria (such as *mycobacterium tuberculosis*), fungal infections (e.g., infections of *Pneumocystis, Candida*, and *Histoplasma*) and viral infections (e.g., infections of influenza, varicella, and corona virus such as SARS-associated coronoavirus). In another embodiment, the disease associated with low MIF expression is meningitis. In another embodiment, the disease associated with low MIF expression is influenza. In one embodiment, the disease associated with low MIF expression is pneumonia (regardless of whether it is caused by a bacterial, viral or fungal infection). In a specific embodiment, the pneumonia is Community Acquired Pneumonia (CAP). In one embodiment, the viral infection is a retroviral infection. In one embodiment, the retroviral infection is HIV infection. In another embodiment, the disease associated with low MIF expression is infection by a virus or other pathogen that use the CCR5 receptor for infection, including, without limitation, HIV-1, HCV, Epstein-Barr Virus, and *Yersinia pestis*.

The Use of MIF Antagonists to Treat Anemia of Chronic Disease

In one embodiment, the invention provides a method of treating anemia of chronic disease comprising administering to a subject a therapeutically effective amount of a MIF antagonist. In certain embodiment, the subject has or is at risk of developing anemia of chronic disease. In one embodiment, the subject has anemia of chronic disease and the subject is not responsive to erythropoietin (EPO) prior to the administration of the MIF antagonist. In one embodiment, the subject is has a genotype that is associated with high MIF expression. In one embodiment, the subject is Caucasian.

Anemia of chronic disease may result from, among other conditions, pathogenic infection (e.g., a malaria infection), cancer, autoimmune diseases or disorders (lupus erythematosis, arthritis, including rheumatoid arthritis, kidney diseases or disorders, organ transplant rejection and aging. The invention provides a method of treating anemia of chronic disease regardless of its cause.

The methods described herein may also comprise the administration of one or more other therapeutic agents. In certain embodiments, the invention provides a method of treating anemia of chromic disease comprising administering to a subject a therapeutically effective amount of a MIF antagonist in combination with one or more other agents that stimulate erythropoiesis. Examples of erythropoiesis-stimulating agents include, without limitation: erythropoietin ("EPO"), iron, folate, vitamin B12, blood, blood substitute, and plasma or serum that contains a composition with the activity of blood. In a specific embodiment, the invention provides a method of treating anemia of chromic disease, comprising administering to a subject in need thereof a MIF antagonist in combination with EPO.

In another embodiment, the invention provides a method of treating anemia of chronic disease, comprising administering to a subject a MIF antagonist in combination with a tumor necrosis factor-α (TNFα) antagonist or an interferon (IFN) antagonist (e.g., an IFNγ antagonist) to a subject. Examples of TNFα and IFNγ antagonists include, without limitation, anti-TNF, soluble TNF receptor, anti-IFNγ, soluble IFNγ receptor, p38 MAPK inhibitors, and JAK-STAT inhibitors.

The Use of MIF Antagonists to Malaria

The invention also comprises a method of treating malaria comprising administering to a subject in need thereof a MIF antagonist. In one embodiment, the subject has malaria or is at risk of developing malaria. In one embodiment, the subject is has a genotype that is associated with high MIF expression. In one embodiment, the subject is Caucasian.

The methods described herein may also comprise the administration of one or more other therapeutic agents.

The Use of MIF Agonists to Treat or Prevent Infections

The invention also comprises a method of treating an infection comprising administering to a subject a therapeutically effective amount of a MIF agonist. In one embodiment, the subject is has a genotype that is associated with low MIF expression.

Infections and diseases that are amenable to treatment with a MIF agonist include, without limitation, viral infections (including retroviral infections), bacterial infections, fungal infections, infections leading to respiratory disease, infections with HIV, pneumonia, Community Acquired Pneumonia (CAP), meningitis, and influenza. In certain embodiments, a MIF agonist is used to treat pathogenic infections during acute stages of infection, including during a flare-up of the infection, during a change of therapy, when signs of resistance to therapy are displayed in the subject, or as an early intervention.

In one embodiment, the invention provides a method of treating an infection that leads to a respiratory disease comprising administering to a subject a therapeutically effective amount of a MIF agonist. Infections that lead or may lead to respiratory disease include, without limitation, infections by gram positive and gram negative bacteria, mycobacteria (such as *mycobacterium tuberculosis*), fungal infections (e.g., infections of *Pneumocystis, Candida*, and *Histoplasma*) and viral infections (e.g., infections of influenza, varicella, and corona virus such as SARS-associated coronoavirus).

The invention also provides a method of treating a respiratory disease resulting from an infection comprising administering to a subject a therapeutically effective amount of a MIF agonist.

In certain embodiments, the invention provides a method of treating pneumonia in a subject comprising administering to the subject a therapeutically effective amount of a MIF agonist. Microbial infections that lead to pneumonia include, without limitation, bacterial infections (e.g., infections of gram positive bacteria, gram negative bacteria, and mycobacteria such as *mycobacterium tuberculosis*), fungal infections (e.g., infections of *Pneumocystis, Candida*, and *His-*

*toplasma*) and viral infections (e.g., infections of influenza, varicella, and corona virus such as SARS-associated coronoavirus).

In certain embodiments, the invention provides a method of treating a retroviral infection comprising administering to a subject a therapeutically effective amount of a MIF agonist.

In certain embodiments, the invention provides a method of treating HIV infection comprising administering to a subject a therapeutically effective amount of a MIF agonist.

The invention also comprises the use of a MIF agonist as an immunoadjuvant.

The methods described herein may also comprise the administration of one or more other therapeutic agents, including without limitation anti-bacterial agents, anti-fungal agents and anti-microbial agents.

Examples of anti-viral agents include, without limitation, reverse transcriptase inhibitors such as, for example, zidovudine, didanosine, zalcitabine, stavudine, lamivudine, abacavir, nevirapine, delavirdine, and efavirenz; protease inhibitors such as, for example, saquinavir, ritonavir, nelfinavir, indinavir, amprenavir, and lopinavir; agents for treating herpes viruses such as, for example, acyclovir, valacyclovir, famciclovir, ganciclovir, foscarnet, and cidolovir; and, agents for treating influenza such as, for example, oseltamivir, amantadine, rimatadine, and zanamivir. Examples of anti-bacterial agents include, without limitation, penicillins, cephalosporins, quinolones, tetracyclines, macrolides. Examples of anti-fungal agents include, without limitation, amphotericin, fluconozole.

Methods of Using a MIF Agonist to Attenuate Expression of CCR5 and Treat HIV Infection In one embodiment, the invention provides a method of attenuating the expression of CCR5 mRNA or protein, comprising the use of a MIF agonist. For example, in one embodiment, cells expressing a CCR5 receptor are contacted with a MIF agonist wherein said contacting results in the attenuation of the expression of CCR5 mRNA or protein.

In another embodiment, the invention provides a method of inhibiting the life-cycle of a virus in a subject infected with said virus or at risk of being infected with said virus, wherein the virus uses the CCR5 as a receptor, administering to the subject a MIF agonist. In one embodiment, the pathogen that uses the CCR5 for infection is HIV-1.

As used herein the "inhibiting the life cycle of a virus" includes, inhibiting viral replication, inhibiting viral infection, latency and oncogenesis.

In a specific embodiment, the invention provides a method of treating HIV infection in a subject infected or at risk of being infected with HIV, comprising administering to the subject a MIF agonist. In one embodiment, the subject is has a genotype that is associated with low MIF expression. In certain embodiments, a MIF agonist is administered to a subject during acute HIV infection or during a flareup.

The methods described herein may also comprise the administration of one or more other therapeutic agents. In one embodiment, the methods described herein comprise the administration of a MIF agonist in combination with anti-viral agents. Examples of anti-viral agents include, without limitation, reverse transcriptase inhibitors such as, for example, zidovudine, didanosine, zalcitabine, stavudine, lamivudine, abacavir, nevirapine, delavirdine, and efavirenz; protease inhibitors such as, for example, saquinavir, ritonavir, nelfinavir, indinavir, amprenavir, and lopinavir; agents for treating herpes viruses such as, for example, acyclovir, valacyclovir, valacyclovir, famciclovir, ganciclovir, foscarnet, and cidolovir; and, agents for treating influenza such as, for example, oseltamivir, amantadine, rimatadine, and zanamivir.

In another aspect, the invention provides a method of treating HIV infection in a subject comprising administering to the subject a therapeutically effective amount of a MIF agonist. In one embodiment, the HIV infection is at an acute stage. In one embodiment, the method further comprises administering to the subject another anti-viral agent.

In one aspect, the invention provides a method of modulating the biological function of MIF, comprising the use of an agent that interacts modulates the interaction of CD44 with CD74.

In one embodiment, the invention provides a method of attenuating the biological function of MIF, comprising the use of an agent that inhibits the interaction between CD44 and CD74. The agent may be any agent. In one embodiment, the agent is selected from the group consisting of: a fragment of CD44, an extracellular fragment of CD44, an agent that binds CD44, an antibody or fragment thereof that binds to CD44, a small molecule, a small molecule mimic of chondroitin sulfate, heparin and a macromolecular mimic of chondroitin sulphate.

In another embodiment, the invention provides a method of attenuating the biological function of MIF, comprising the use of an agent that inhibits the expression of CD44. The agent may be any agent. In one embodiment, the agent is an siRNA or antisense polynucleotide that targets CD44.

In one embodiment, the invention provides a method of increasing the biological function of MIF, comprising the use of an agent that increases the interaction between MIF, CD44 and CD74.

In one embodiment, the invention provides a method of increasing the biological function of MIF, comprising the use of an agent that increases the interaction between CD44 and CD74.

The compounds of the invention may also be effective for modulating (e.g. increasing or decreasing) the action of MIF at other CD74-associated receptors and coreceptors, such as CXCR2 and CXCR4. The compounds may modulate (e.g. increase or decrease) the interaction between CD74 and such CD74-associated receptors and coreceptors.

As used herein, a "disease associated with high MIF expression" or a "disease associated with low MIF expression" is a disease associated with high or low MIF expression, respectively. This association can be established using well known methods. For example, diseases that are associated with high MIF expression include: autoimmunity, cancer, anemia of chronic disease, malaria, and asthma. Diseases that are associated with low, or insufficient, MIF expression include: infections (including viral, bacterial and fungal infections) and diseases resulting from, or caused by, infections, including respiratory diseases resulting from any infection, meningitis, pneumonia, CAP, influenza, sepsis, HIV infection, and infection with a pathogen that uses CCR5 as a receptor (such as HIV-1, Hepatitis C Virus (HCV), Epstein-Barr Virus, or *Yersinia pestis*).

Representative cancers which may be treated using compounds according to the present invention include, for example, stomach, colon, rectal, liver, pancreatic, lung, breast, cervix uteri, corpus uteri, ovary, prostate, testis, bladder, renal, brain/CNS, head and neck, throat, Hodgkin's disease, non-Hodgkin's lymphoma, multiple myeloma, leukemia, melanoma, non-melanoma skin cancer, acute lymphocytic leukemia, acute myelogenous leukemia, Ewing's sarcoma, small cell lung cancer, choriocarcinoma, glioma, teratoma, rhabdomyosarcoma, Wilms' tumor, neuroblastoma, hairy cell leukemia, mouth/pharynx, oesophagus, larynx, kidney cancer and other lymphoma, among others.

Compounds according to the present invention may be administered in combination with additional anticancer agents. These agents include, for example, antimetabolites, inhibitors of topoisomerase I and II, alkylating agents and microtubule inhibitors (e.g., taxol). Specific anticancer compounds for use in the present invention include, for example, adriamycin aldesleukin; alemtuzumab; alitretinoin; allopurinol; altretamine; amifostine; anastrozole; arsenic trioxide; Asparaginase; BCG Live; bexarotene capsules; bexarotene gel; bleomycin; busulfan intravenous; busulfan oral; calusterone; capecitabine; carboplatin; carmustine; carmustine with Polifeprosan 20 Implant; celecoxib; chlorambucil; cisplatin; cladribine; cyclophosphamide; cytarabine; cytarabine liposomal; dacarbazine; dactinomycin; actinomycin D; Darbepoetin alfa; daunorubicin liposomal; daunorubicin, daunomycin; Denileukin diftitox, dexrazoxane; docetaxel; doxorubicin; doxorubicin liposomal; Dromostanolone propionate; Elliott's B Solution; epirubicin; Epoetin alfa estramustine; etoposide phosphate; etoposide (VP-16); exemestane; Filgrastim; floxuridine (intraarterial); fludarabine; fluorouracil (5-FU); fulvestrant; gemcitabine, gemtuzumab ozogamicin; goserelin acetate; hydroxyurea; Ibritumomab Tiuxetan; idarubicin; ifosfamide; imatinib mesylate; Interferon alfa-2a; Interferon alfa-2b; irinotecan; letrozole; leucovorin; levamisole; lomustine (CCNU); mechlorethamine (nitrogen mustard); megestrol acetate; melphalan (L-PAM); mercaptopurine (6-MP); mesna; methotrexate; methoxsalen; mitomycin C; mitotane; mitoxantrone; nandrolone phenpropionate; Nofetumomab; LOddC; Oprelvekin; oxaliplatin; paclitaxel; pamidronate; pegademase; Pegaspargase; Pegfilgrastim; pentostatin; pipobroman; plicamycin; mithramycin; porfimer sodium; procarbazine; quinacrine; Rasburicase; Rituximab; Sargramostim; streptozocin; talbuvidine (LDT); talc; tamoxifen; temozolomide; teniposide (VM-26); testolactone; thioguanine (6-TG); thiotepa; topotecan; toremifene; Tositumomab; Trastuzumab; tretinoin (ATRA); uracil mustard; valrubicin; valtorcitabine (monoval LDC); vinblastine; vinorelbine; zoledronate; and mixtures thereof, among others.

A "disease associated with high MIF expression" or a "disease associated with low MIF expression" also includes a disease in which an endogenous MIF response to treatment causes or exacerbates the disease. For example, a "disease associated with high MIF expression" includes an inflammatory or atherosclerotic lesion or a disorder that proves resistant to steroid treatment. Inflammatory diseases or disorders which may be treated using compounds according to the present invention include inflammatory diseases or disorders including arthritis, especially including rheumatoid arthritis, costochondritis, lupus, multiple sclerosis, Perthes' disease, the secondary arthritic effects of Lyme disease and inflammatory bowel disease, including Crohn's disease, gastritis, uncontrolled skin inflammation and pulmonary pneumonitis, among others.

As used herein, "anemia of chronic disease" refers to anemia that is immune driven. Anemia of chronic disease also known as "anemia of inflammation." This condition can result from a condition selected from the group consisting of: a pathogenic infection, cancer, an autoimmune disease or disorder, a kidney disease or disorder, organ transplant rejection, and aging. See, e.g., Weiss and Goodnought, "Anemia of Chronic Disease", N. Engl. J. Med. 352(10): 1011-23 (2005).

As used herein, the term "therapeutically effective amount" refers to the amount of a MIF agonist or antagonist (isolated or recombinantly produced), or a composition comprising a MIF agonist or antagonist, that is in sufficient quantities to treat a subject having, or at risk of developing, a disease associated with high or low MIF expression, or to treat a disease associated with high or low MIF expression itself. For example, an effective amount is sufficient to delay, slow, or prevent the onset or progression of a disease associated with high or low MIF expression, or related symptoms.

The term "pharmaceutically acceptable" refers to a carrier, additive or excipient which is not unacceptably toxic to the subject to which it is administered. Pharmaceutically acceptable excipients are described at length by E. W. Martin, in "Remington's Pharmaceutical Sciences", among others well-known in the art.

A "pharmaceutically acceptable salt" of the present compound generally refers to pharmaceutically acceptable salts form of a compound which can form a salt, because of the existence of for example, amine groups, carboxylic acid groups or other groups which can be ionized in a sample acid-base reaction. A pharmaceutically acceptable salt of an amine compound, such as those contemplated in the current invention, include, for example, ammonium salts having as counterion an inorganic anion such as chloride, bromide, iodide, sulfate, sulfite, nitrate, nitrite, phosphate, and the like, or an organic anion such as acetate, malonate, pyruvate, propionate, fumarate, cinnamate, tosylate, and the like. Certain compounds according to the present invention which have carboxylic acid groups or other acidic groups which may form pharmaceutically acceptable salts, for example, as carboxylate salts, are also contemplated by the present invention.

Aspects of the present invention include compounds which have been described in detail hereinabove or to pharmaceutical compositions which comprise an effective amount of one or more compounds according to the present invention, optionally in combination with a pharmaceutically acceptable carrier, additive or excipient.

The term "pharmaceutically acceptable derivative" is used throughout the specification to describe any pharmaceutically acceptable prodrug form (such as an ester or ether or other prodrug group) which, upon administration to a patient, provides directly or indirectly the present compound or an active metabolite of the present compound.

The term "inhibitory effective concentration" or "inhibitory effective amount" is used throughout the specification to describe concentrations or amounts of compounds according to the present invention which substantially or significantly modulate levels of MIF expression.

The term "preventing effective amount" is used throughout the specification to describe concentrations or amounts of compounds according to the present invention which are prophylactically effective in preventing, reducing the likelihood of infection or delaying the onset of a disease associated with high or low levels of MIF expression. The terms inhibitory effective amount or preventive effective amount also generally fall under the rubric "effective amount".

The term "co-administration" is used to describe the administration of two active compounds, in this case a compound according to the present invention, in combination with an additional MIF-modulating agent or other biologically active agent, in effective amounts. Although the term co-administration preferably includes the administration of two active compounds to the patient at the same time, it is not necessary that the compounds actually be administered at the exact same time, only that amounts of compound will be administered to a patient or subject such that effective concentrations are found in the blood, serum or plasma, or in the pulmonary tissue at the same time.

General Information Relating to Methods of Treatment Using MIF Agonists or MIF Antagonist The methods described herein for treating a subject suffering from or at risk of developing a disease or condition associated with high or low levels of MIF expression may be used for the prophylactic treatment of individuals who have been diagnosed or predicted to be at risk for developing a disease or condition associated with high or low MIF expression. Thus, in one embodiment, a composition comprising a MIF agonist or antagonist is administered in an amount and dose that is sufficient to delay, slow, or prevent the onset of a disease or condition associated with high or low MIF expression, or related symptoms, or to reverse a disease or condition associated with high or low MIF expression. It is understood that an effective amount of a composition for treating a subject who has been diagnosed or predicted to be at risk for developing a disease or condition associated with high or low MIF expression is a dose or amount that is in sufficient quantities to treat a subject or to treat the disorder itself.

MIF agonists and antagonists may be formulated with a pharmaceutically acceptable carrier. For example, a MIF agonist or antagonist can be administered alone or as a component of a pharmaceutical formulation (therapeutic composition). The MIF agonist or antagonist may be formulated for administration in any convenient way for use in human medicine.

In certain embodiments, the therapeutic methods of the invention include administering the composition topically, systemically, or locally. For example, therapeutic compositions of the invention may be formulated for administration by, for example, injection (e.g., intravenously, subcutaneously, or intramuscularly), inhalation or insufflation (either through the mouth or the nose) or oral, buccal, sublingual, transdermal, nasal, or parenteral administration. The compositions described herein may be formulated as part of an implant or device. When administered, the therapeutic composition for use in this invention is in a pyrogen-free, physiologically acceptable form. Further, the composition may be encapsulated or injected in a viscous form for delivery to the site where the target cells are present. Techniques and formulations generally may be found in Remington's Pharmaceutical Sciences, Meade Publishing Co., Easton, Pa. In addition to MIF agonists or antagonists, therapeutically useful agents may optionally be included in any of the compositions described herein. Furthermore, therapeutically useful agents may, alternatively or additionally, be administered simultaneously or sequentially with a MIF agonist or antagonist according to the methods of the invention.

In certain embodiments, compositions comprising a MIF agonist or antagonist can be administered orally, e.g., in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of an agent as an active ingredient. An agent may also be administered as a bolus, electuary or paste.

In solid dosage forms for oral administration (capsules, tablets, pills, dragees, powders, granules, and the like), one or more compositions comprising a MIF agonist or antagonist may be mixed with one or more pharmaceutically acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose, and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, cetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof; and (10) coloring agents. In the case of capsules, tablets and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols and the like.

Liquid dosage forms for oral administration include pharmaceutically acceptable emulsions, microemulsions, solutions, suspensions, syrups, and elixirs. In addition to the active ingredient, the liquid dosage forms may contain inert diluents commonly used in the art, such as water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor, and sesame oils), glycerol, tetrahydrofuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, coloring, perfuming, and preservative agents.

Suspensions, in addition to the active compounds, may contain suspending agents such as ethoxylated isostearyl alcohols, polyoxyethylene sorbitol, and sorbitan esters, microcrystalline cellulose, aluminum metahydroxide, bentonite, agar-agar and tragacanth, and mixtures thereof.

Certain compositions disclosed herein may be administered topically, either to skin or to mucosal membranes. The topical formulations may further include one or more of the wide variety of agents known to be effective as skin or stratum corneum penetration enhancers. Examples of these are 2-pyrrolidone, N-methyl-2-pyrrolidone, dimethylacetamide, dimethylformamide, propylene glycol, methyl or isopropyl alcohol, dimethyl sulfoxide, and azone. Additional agents may further be included to make the formulation cosmetically acceptable. Examples of these are fats, waxes, oils, dyes, fragrances, preservatives, stabilizers, and surface active agents. Keratolytic agents such as those known in the art may also be included. Examples are salicylic acid and sulfur.

Dosage forms for the topical or transdermal administration include powders, sprays, ointments, pastes, creams, lotions, gels, solutions, patches, and inhalants. The active compound may be mixed under sterile conditions with a pharmaceutically acceptable carrier, and with any preservatives, buffers, or propellants that may be required. The ointments, pastes, creams and gels may contain, in addition to a MIF agonist or antagonist, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to a MIF agonist or antagonist, excipients such as lactose, talc, silicic acid, aluminum hydroxide, calcium silicates, and polyamide powder, or mixtures of these substances. Sprays can additionally contain customary propellants, such as chlorofluorohydrocarbons and volatile unsubstituted hydrocarbons, such as butane and propane.

In certain embodiments, pharmaceutical compositions suitable for parenteral administration may comprise a MIF agonist or antagonist in combination with one or more pharmaceutically acceptable sterile isotonic aqueous or non-aqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents. Examples of suitable aqueous and nonaqueous carriers which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

A composition comprising a MIF agonist or antagonist may also contain adjuvants, such as preservatives, wetting agents, emulsifying agents and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption, such as aluminum monostearate and gelatin.

General Chemistry for Producing Compositions According to the Present Invention

Chemical syntheses of compounds of structure (I) above are generally prepared by cyclizing intermediates to form five or 6:5 fused heterocyclic rings. The intermediates which are initially prepared or purchased may be readily cyclized to form the various compounds according to the present invention. Various analogous chemical schemes are presented which result in the present compounds.

Benzooxazolone derivatives of the invention can be prepared as follows.

Representative procedure for
5-methyl-3H-benzooxazol-2-one derivatives 1, 5, 6 and 7

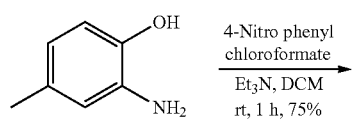

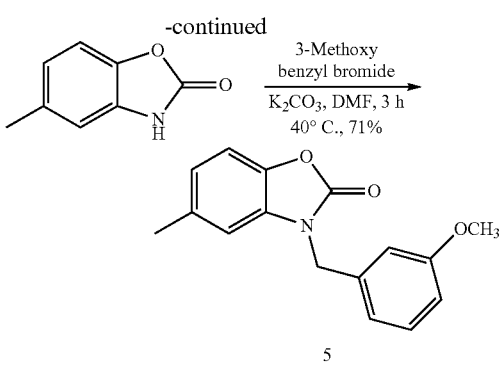

To a solution of 2-amino-4-methylphenol (1.0 gm, 8.13 mmol) and Et$_3$N (1.6 gm, 16.26 mmol) in CH$_2$Cl$_2$ (20 ml) was added 4-nitrophenylchloroformate (1.8 gm, 8.94 mmol) as a CH$_2$Cl$_2$ solution at 0° C. for 10 min under nitrogen atmosphere and the reaction mixture was allowed to warm to rt (room temperature) and stirred for 1 h. The reaction mixture was diluted with CH$_2$Cl$_2$ (15 ml) and washed with water and brine. The organic phase was dried over anhydrous MgSO$_4$ and evaporated under vacuum. The product was purified by column chromatography, eluting with n-hexane:AcOEt (2:8) on silica gel to give 5-methylbenzo[d]oxazol-2(3H)-one as an off-white solid (900 mg, 75%).

To a solution of 5-methylbenzo[d]oxazol-2(3H)-one (95 mg, 0.63 mmol) and K$_2$CO$_3$ (342 mg, 1.89 mmol) in CH$_3$CN (3 ml) was added 3-methoxybenzyl bromide (230 mg, 0.69 mmol) at 40° C. and the reaction was stirred under nitrogen atmosphere for 3 h. The reaction mixture was poured into ice water and extracted with AcOEt (2×5 ml), the combined organic layers were dried over anhydrous MgSO$_4$ and evaporated under vacuum. The product was purified by column chromatography, eluting with n-hexane:AcOEt (1:1) on silica gel to yield 5 as a colorless solid (120 mg, 71%).

Synthesis of
3-benzyl-6-methyl-3H-benzooxazol-2-one (2)

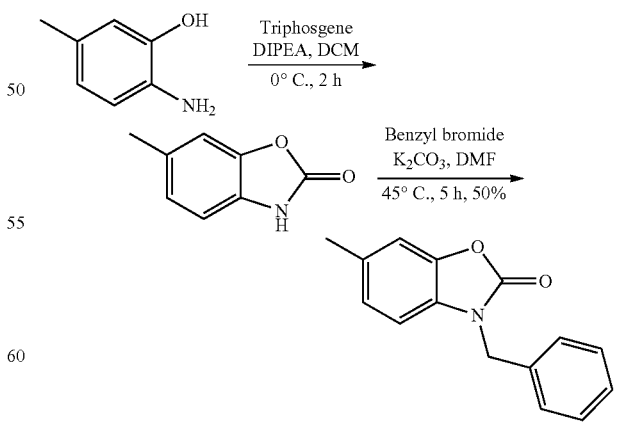

A solution of 2-amino-5-methyl-phenol (1.0 gm, 8.1 mmol) in CH$_2$Cl$_2$ (30 ml) was cooled to 0° C. Triphosgene (721 mg, 2.43 mmol) was added followed by diisopropylethylamine (7.0 ml, 17.6 mmol) and the reaction mixture was stirred under nitrogen atmosphere for 2 h. The reaction mixture was washed with water and brine. The organic phase was dried over anhydrous MgSO$_4$ and evaporated under vacuum. The crude product 6-methylbenzo[d]oxazol-2(3H)-one was used for the next step without any purification.

To a solution of 6-methylbenzo[d]oxazol-2(3H)-one (300 mg, 1.98 mmol) and K$_2$CO$_3$ (668 mg, 4.95 mmol) in DMF was added benzyl bromide (375 mg, 2.1 mmol) at 45° C. and the reaction was stirred under nitrogen atmosphere for 5 h. The reaction mixture was poured into ice water and the precipitate was filtered, washed with n-hexane and dried under vacuum to give compound 2 (250 mg, 50%) as a white solid.

Synthesis of 5-methoxy-3-(3-methoxy-benzyl)-3H-benzooxazol-2-one (3)

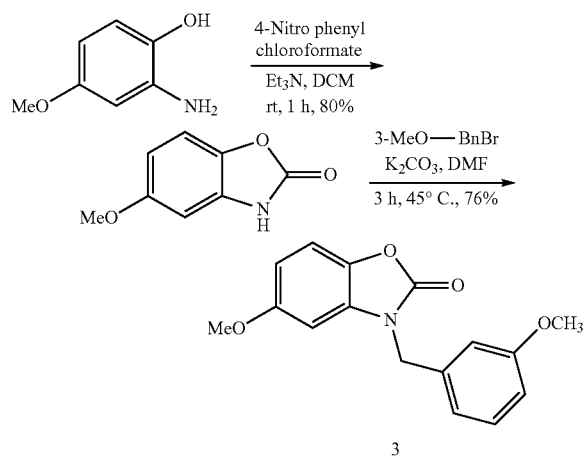

3

To a solution of 2-amino-4-methoxy-phenol (2.46 gm, 17.7 mmol) and Et$_3$N (5.3 gm, 53.1 mmol) in CH$_2$Cl$_2$ (40 ml) was added 4-nitro phenylchloroformate (3.75 gm, 19.47 mmol) as a CH$_2$Cl$_2$ (20 ml) solution at 0° C. for 10 min under nitrogen atmosphere and the reaction mixture was stirred to rt for 1 h. The reaction mixture was diluted with CH$_2$Cl$_2$ (40 ml) and washed with water and brine. The organic phase was dried over anhydrous MgSO$_4$ and evaporated under vacuum. The product was purified by column chromatography, eluting with n-hexane:AcOEt (4:6) to give 5-methoxy-3H-benzooxazol-2-one as off white solid (2.3 gm, 80%).

To a solution of 5-methoxy-3H-benzooxazol-2-one (150 mg, 0.90 mmol) and K$_2$CO$_3$ (376 mg, 2.7 mmol) in DMF (5 ml) was added 3-methoxybenzyl bromide (200 mg, 0.99 mmol) at 45° C. and the reaction mixture was stirred under nitrogen atmosphere for 3 h. The reaction mixture was poured into ice water and extracted with ethyl acetate (2×8 ml), the combined organic layers were dried over anhydrous MgSO$_4$ and evaporated under vacuum. The residue was purified by column chromatography, eluting with n-hexane:AcOEt (1:1) to yield 3 (181 mg, 76%) as a colorless solid.

Synthesis of 5-hydroxymethyl-3-(3-methoxy-benzyl)-3H-benzooxazol-2-one (4)

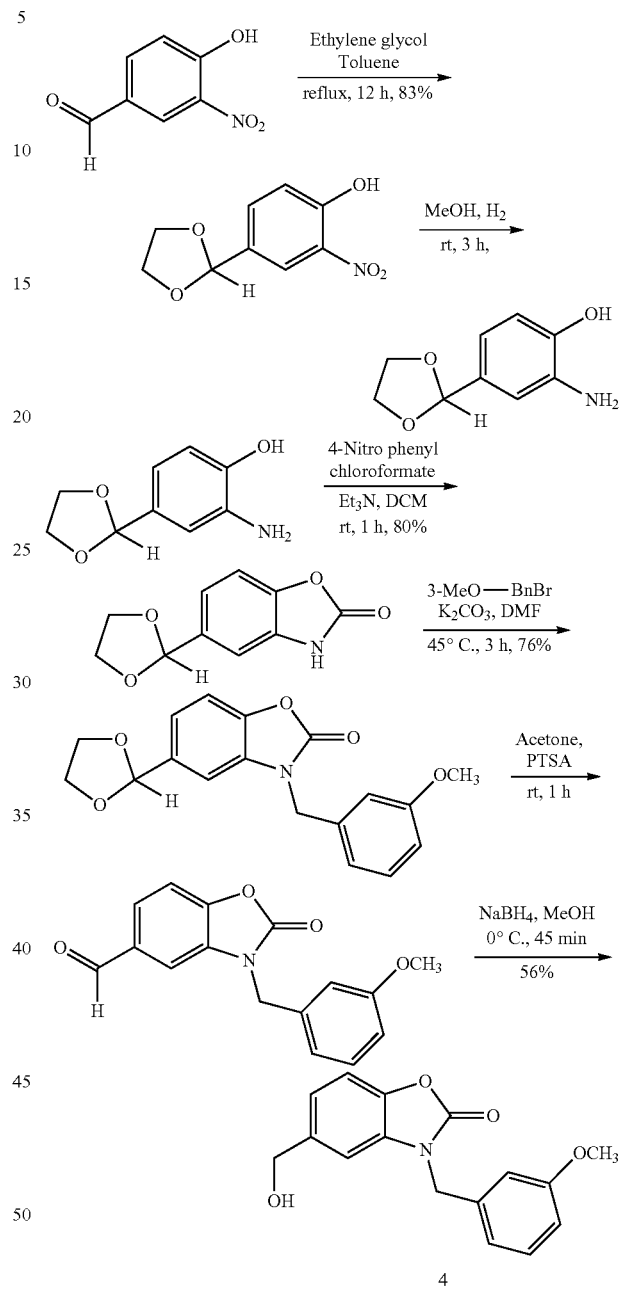

4

A mixture of 4-hydroxy-3-nitro-benzaldehyde (1.0 gm, 5.9 mmol), ethylene glycol (885 mg, 14.75 mmol) and catalytic amount of PTSA (pyridiniump-toluenesulfonate) were refluxed in toluene (30 ml) under nitrogen atmosphere for 12 h. The reaction mixture was concentrated and poured into ice water and extracted with AcOEt (2×15 ml), the combined organic layers were dried over anhydrous MgSO$_4$ and evaporated under vacuum. The reaction mixture was purified by column chromatography, eluting with n-hexane:AcOEt (1:1) to yield 4-[1,3]dioxolan-2-yl-2-nitro-phenol (1.0 gm, 83%) as a yellow solid.

A mixture of 4-[1,3]dioxolan-2-yl-2-nitro-phenol (900 mg, 4.26 mmol) and Pd/C (10%, 150 mg) in MeOH (15 ml)

was stirred at rt under H₂ pressure (30 psi) for 3 h. The reaction mixture was filtered through celite and evaporated under vacuum to obtain 2-amino-4-[1,3]dioxolan-2-yl-phenol (771 mg). This was used as such for the next step.

To a solution of 2-amino-4-[1,3]dioxolan-2-yl-phenol (290 mg, 1.6 mmol) and diisopropylethylamine in CH₂Cl₂ (15 ml) was added triphosgene (166 mg, 0.56 mmol) as a CH₂Cl₂ (3 ml) solution for 5 min at 0° C. under nitrogen atmosphere and the reaction mixture was allowed to come to rt, and stirred for 2 h. The reaction mixture was washed with water and brine. The organic phase was dried over MgSO₄ and evaporated under vacuum. The reaction mixture was purified by chromatography, eluting with n-hexane:AcOEt (4:6) to obtain 5-[1,3]dioxolan-2-yl-3H-benzooxazol-2-one (220 mg, 66%) as a white solid.

To a solution of 5-[1,3]dioxolan-2-yl-3H-benzooxazol-2-one (100 mg, 0.48 mmol) and K₂CO₃ (132 mg, 0.96 mmol) in DMF (5 ml) was added 3-methoxybenzyl bromide (132 mg, 0.48 mmol) at 45° C. and the reaction was stirred under nitrogen for 3 h. The reaction mixture was poured into ice water and extracted with ethyl AcOEt (2×5 ml) the combined organic layers were dried over anhydrous MgSO₄ and evaporated under vacuum. The residue was purified by column chromatography, eluting with n-hexane:AcOEt (1:1) to yield 5-[1,3]dioxolan-2-yl-3-(3-methoxy-benzyl)-3H-benzooxazol-2-one (120 mg, 76%) as a colorless solid.

To a solution of 5-[1,3]dioxolan-2-yl-3-(3-methoxy-benzyl)-3H-benzooxazol-2-one in acetone (5 ml) was added catalytic amount of PTSA and stirred at rt under nitrogen atmosphere for 1 h. The reaction mixture was diluted with ethyl acetate, to this water and brine wash was given. The organic layer was dried over anhydrous MgSO₄ and evaporated under vacuum to obtain 3-(3-methoxy-benzyl)-2-oxo-2,3-dihydro-benzooxazole-5-carbaldehyde (110 mg) as a solid. This was used as it is for the next step.

To a solution of 3-(3-methoxy-benzyl)-2-oxo-2,3-dihydro-benzooxazole-5-carbaldehyde (110 mg, 0.38 mmol) in MeOH (5 ml) was added NaBH₄ (5 mg, 0.11 mmol) at ice temperature and stirred for 45 min under nitrogen atmosphere, reaction mixture was diluted with ethyl acetate (10 ml) and washed with water and brine. The organic layer was dried over MgSO₄ and evaporated under vacuum. The residue was purified by column chromatography eluting with n-hexane:AcOEt (3:7) to yield compound 4 (60 mg, 56%) as colorless solid Representative procedure for
5-fluoro-benzooxazol-2-one derivatives 8, 9, and 10

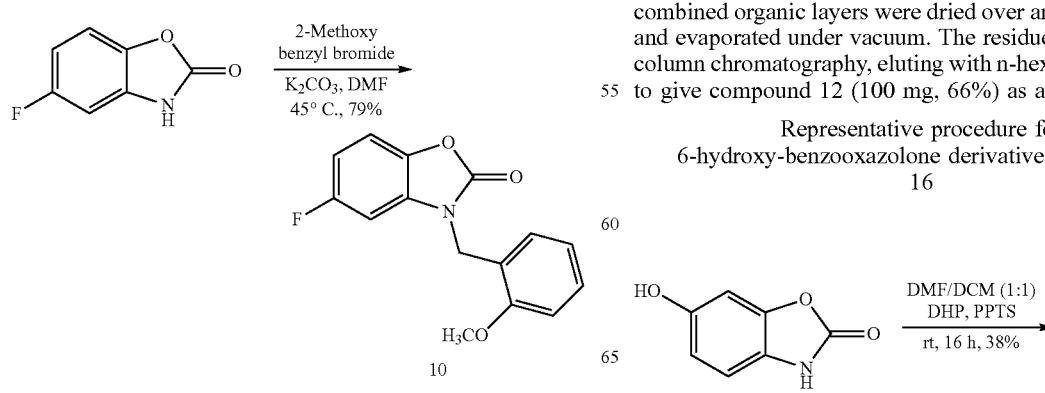

To a solution of 5-fluorobenzo[d]oxazol-2(3H)-one (100 mg, 0.65 mmol) and K₂CO₃ (278 mg, 1.95 mmol) in DMF (3 ml) was added 2-methoxybenzyl bromide (375 mg, 2.1 mmol) at 45° C. and the reaction was stirred under nitrogen atmosphere for 5 h. The reaction mixture was poured into ice water and the precipitate was filtered, washed with n-hexane and dried under vacuum to give compound 10 (140 mg, 79%) as a white solid.

Representative procedure
5-hydroxy-benzooxazol-2-one derivatives 11, 12 and 13

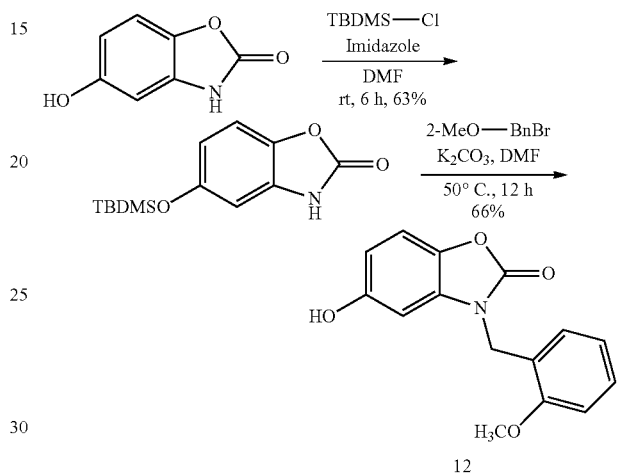

To a mixture of 5-hydroxy-3H-benzooxazol-2-one [Naoki, I.; Takeshi, S.; Etsuko, M.; Yasuo, K. *J. Org. Chem.* 2002, 67, 7424-7428] (100 mg, 0.71 mmol) and imidazole (97.7 mg, 1.42 mmol) in DMF (4 ml) was added t-butyldimethylsilyl chloride (TBDMS-Cl, 161.7 mg, 1.06 mmol) at ice temperature under nitrogen atmosphere and the reaction was stirred for 6 h at rt. The reaction mixture was poured in to ice water and extracted with ethyl acetate for (3×5 ml), the combined organic layers were dried over anhydrous MgSO₄ and evaporated under vacuum. The residue was purified by column chromatography eluting with n-hexane:AcOEt (2:8) to give 5-(tert-butyl-dimethyl-silanyloxy)-3H-benzooxazol-2-one (120 mg, 63%) as white solid.

To a solution of 5-(tert-butyl-dimethyl-silanyloxy)-3,4-benzooxazol-2-one (195 mg, 1.4 mmol) in DMF (5 ml) was added 2-methoxybenzyl bromide (129 mg, 0.56 mmol) at 50° C. under nitrogen atmosphere and the reaction was stirred for 12 h. The reaction mixture was poured in to ice water and extracted with ethyl acetate for (3×5 ml), the combined organic layers were dried over anhydrous MgSO₄ and evaporated under vacuum. The residue was purified by column chromatography, eluting with n-hexane:AcOEt (1:1) to give compound 12 (100 mg, 66%) as a white solid.

Representative procedure for
6-hydroxy-benzooxazolone derivatives 14, 15 and 16

47
-continued

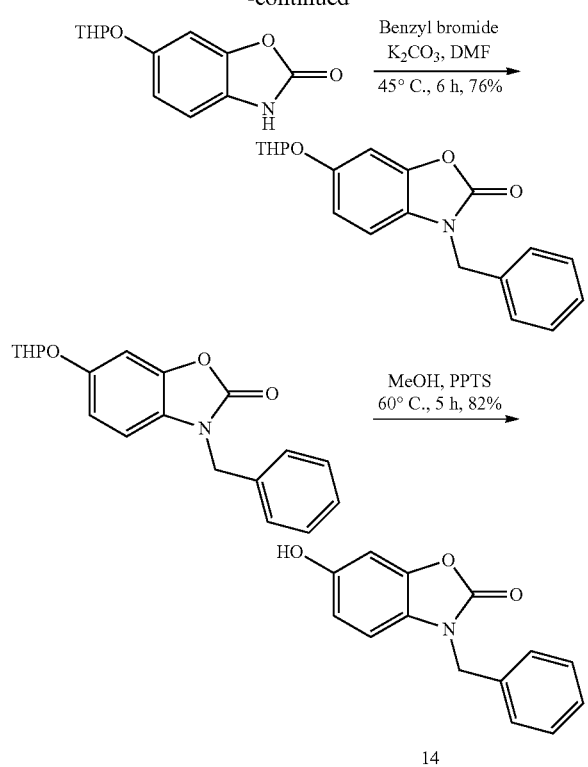

To a mixture of commercially available 6-hydroxy-3H-benzooxazol-2-one (500 mg, 3.3 mmol) and DHP (1.38 gm, 16.5 mmol) in DMF/CH$_2$Cl$_2$ (10 ml) was added a catalytic amount of PPTS and the reaction was stirred for 16 h at rt. The reaction mixture was diluted with CH$_2$Cl$_2$ (25 ml) and washed with water and brine. The organic phase was dried over anhydrous MgSO$_4$ and evaporated under vacuum. The product was purified by column chromatography, eluting with n-hexane:AcOEt (7:3) to give 6-(tetrahydro-2H-pyran-2-yloxy)benzo[d]oxazol-2(3H)-one (300 mg, 1.25 mmol, 38%) as colorless solid.

To a solution of 6-(tetrahydro-2H-pyran-2-yloxy)benzo[d]oxazol-2(3H)-one (120 mg, 0.51 mmol) and K$_2$CO$_3$ (211 mg, 1.5 mmol) in DMF (3 ml) was added benzyl bromide (86 mg, 0.50 mmol) at 45° C. and the reaction was stirred under nitrogen atmosphere for 6 h. The reaction mixture was poured into ice water and extracted with AcOEt (3×5 ml) the combined organic layers were dried over anhydrous MgSO$_4$ and evaporated under vacuum. The residue was purified by column chromatography, eluting with n-hexane:AcOEt (1:1) on silica gel to yield 3-(benzyl)-6-(tetrahydro-2H-pyran-2-yloxy)benzo[d]oxazol-2(3H)-one (140 mg, 85%) as a colorless solid.

To a solution of 3-(benzyl)-6-(tetrahydro-2H-pyran-2-yloxy)benzo[d]oxazol-2(3H)-one (140 mg, 0.43 mmol) in MeOH (5 ml) was added catalytic amount of PPTS and the reaction was stirred for 5 h at 60° C. The reaction mixture was diluted with CH$_2$Cl$_2$ (10 ml) and washed with water and brine. The organic phase was dried over MgSO$_4$ and evaporated under vacuum. The product was purified by column chromatography, eluting with n-hexane:AcOEt (2:8) to give compound 14 (73.3 mg, 82%) as white solid.

48

Synthesis of
4-(1-benzyl-1,1-benzo[d]imidazol-2-yl)thiazole (17)

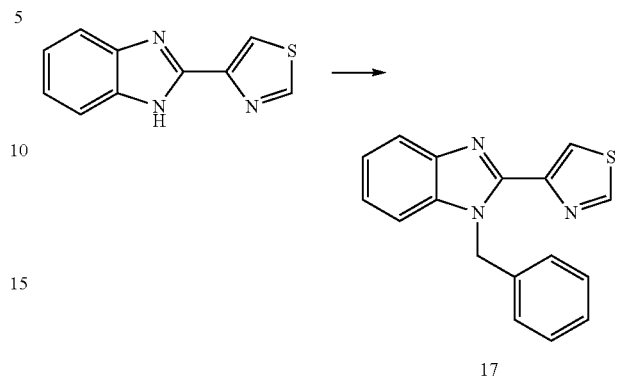

To solution of commercially available thiabendazole (100 mg, 0.49 mmol) and K$_2$CO$_3$ (132 mg, 0.98 mmol) in DMF was added benzyl bromide (92.7 mg, 0.53 mmol) at 60° C. and the reaction was stirred under nitrogen atmosphere for 12 h. The reaction mixture was poured into ice water and extracted with AcOEt (3×5 ml), the combined organic layers were dried over MgSO$_4$ and evaporated under vacuum. The residue was purified by column chromatography to yield 17 (135 mg, 0.46 mmol, 94%) as a colorless solid.

Synthesis of
1-Benzyl-1H-benzoimidazole-2-carbonitrile (18)

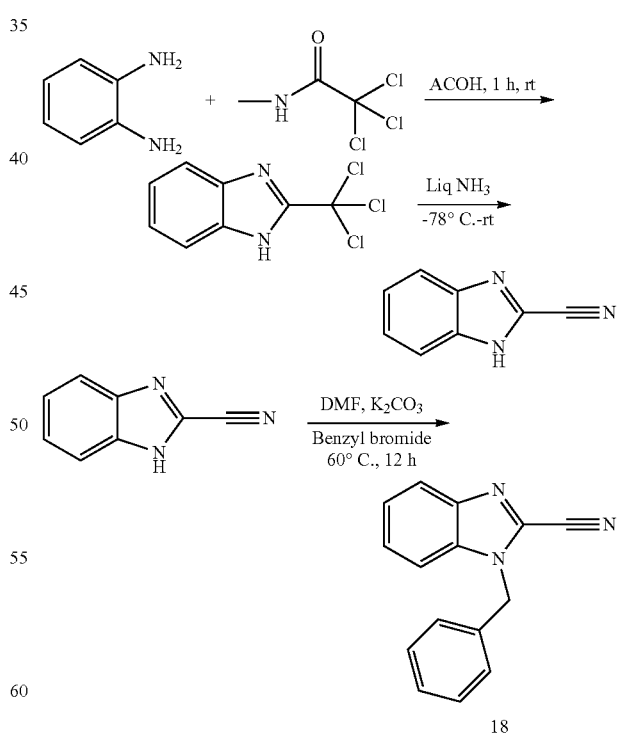

Methyl 2,2,2-trichloroacetamide (1.83 gm, 17 mmol) was added to a solution of o-phenylenediamine (3 gm, 17.0 mmol) in acetic acid, which was then stirred at room temperature for 1 h. Water was added (20 mL) to the mixture, and resultant precipitate was filtered. The filtrate was washed with water and dried under vacuum to afford 2-Trichloromethyl-1H-benzoimidazole (3.4 gm, 14.4 mmol, 85%) as a dark yellow color solid.

2-Trichloromethylbenzamidazole (500 mg, 2.1 mmol) was added proportion wise to anhydrous ammonia at −78° C. The mixture was stirred 5 min at −78° C. and the cooling bath was removed. The reaction mixture was allowed to warm to room temperature. After the ammonia had evaporated the solid was extracted with boiling ethyl acetate. The organic layer was dried over MgSO$_4$ and concentrated under vacuum. The residue was purified by column chromatography to yield 1H-Benzoimidazole-2-carbonitrile (267 mg, 1.86 mmol, 88%) as a white solid.

To solution of 1H-Benzoimidazole-2-carbonitrile (70 mg, 0.48 mmol) and K$_2$CO$_3$ (132 mg, 0.96 mmol) in DMF was added benzyl bromide (82 mg, 0.48 mmol) at 60° C. and the reaction was stirred at rt under nitrogen atmosphere for 12 h. The reaction mixture was poured into ice water and extracted with ethyl acetate for 3 times, the combined organic layers were dried over MgSO$_4$ and evaporated under vacuum. The residue was purified by column chromatography to yield 34 (100 mg, 0.42 mmol, 89%) as a colorless solid.

Representative procedure for bisbenzofuran-2-yl methanone (20) derivatives

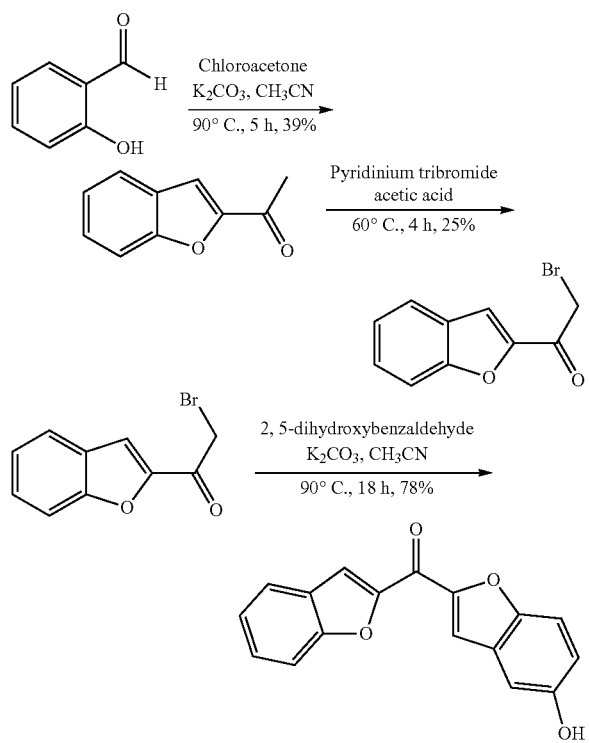

To a solution of 2-hydroxybenzaldehyde (0.96 ml, 10 mmol) and K$_2$CO$_3$ (1.382 g, 10 mmol) in CH$_3$CN (20 ml) was added chloroacetone (0.876 ml, 11 mmol) dropwise, via syringe, at room temperature. The reaction flask then was fitted with a reflux condenser and the solution was heated to 90° C. The reaction was stirred at reflux, under nitrogen atmosphere, for 5 h. The reaction then was allowed to cool to room temperature and the reaction mixture was diluted with CH$_2$Cl$_2$ (20 ml). The solid salts were filtered off and the filtrate reduced under vacuum. The product was purified by column chromatography, eluting with n-hexane:AcOEt (9:1). Further purification by recrystallization from EtOH yielded 1-(benzofuran-2-yl)ethanone (630.5 mg, 39%) as a white solid.

To a solution of 1-(benzofuran-2-yl)ethanone (448 mg, 2.8 mmol) in acetic acid (10 ml) was added pyridinium tribromide (1.12 g, 3.5 mmol) in portions. The reaction was warmed to 60° C. and the reaction was stirred under nitrogen atmosphere for 4 h. The reaction was then quenched with H$_2$O (20 ml) and neutralized with saturated NaHCO$_3$ solution. The product was extracted with AcOEt and washed with water and brine. The organic phase was dried over MgSO$_4$ and evaporated under vacuum. The product was purified recyrstallization from EtOH to give 1-(benzofuran-2-yl)-2-bromoethanone (170 mg, 25%) as a white solid.

To a solution of 2,5-dihydroxybenzaldehyde (86 mg, 0.62 mmol) and K$_2$CO$_3$ (85 mg, 0.62 mmol) in CH$_3$CN (5 ml) was added 1-(benzofuran-2-yl)-2-bromoethanone (60 µl, 0.62 mmol) in portions. The reaction flask was then fitted with a reflux condenser and the solution was heated to 90° C. The reaction was stirred at reflux, under nitrogen atmosphere, for 18 h. The reaction was allowed to cool to room temperature and the reaction mixture was diluted with CH$_2$Cl$_2$ (20 ml). The solid salts were filtered off and the filtrate reduced under vacuum. The product was purified by column chromatography, eluting with n-hexane:AcOEt (9:1). Further purification by recrystallization from EtOH yielded benzofuran-2-yl(5-hydroxybenzofuran-2-yl)methanone (135 mg, 78%) as a white solid.

In addition to the syntheses described above, representative syntheses of formula (II)(A) compounds also include (but are not limited to) the following syntheses:

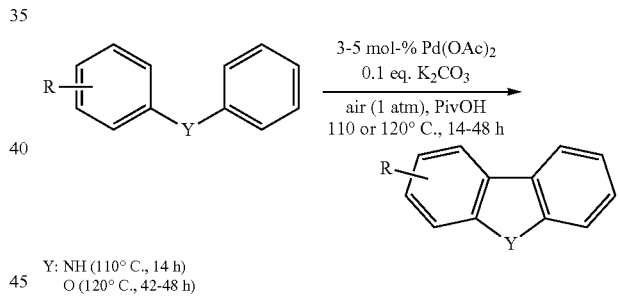

Y: NH (110° C., 14 h)
O (120° C., 42-48 h)

The above process provides an intramolecular palladium (II)-catalyzed oxidative carbon-carbon bond formation under air in the presence of pivalic acid as the reaction solvent, instead of acetic acid, results in greater reproducibility, higher yields, and broader substrate scope. The reaction allows the conversion of both electron-rich and electron-deficient diarylamines. B. Liegault, D. Lee, M. P. Huestis, D. R. Stuart, K. Fagnou, *J. Org. Chem.*, 2008, 73, 5022-5028.

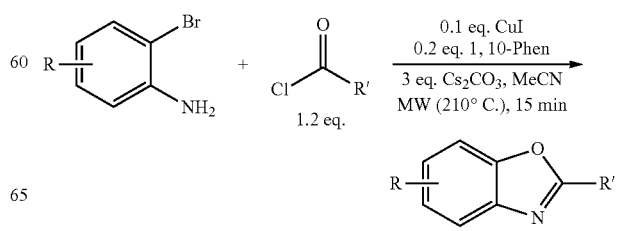

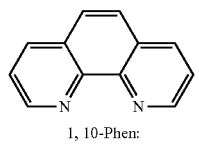

1, 10-Phen:

The above process provides a versatile one-pot domino acylation annulation reaction of 2-bromoanilines with acyl chlorides in the presence of $Cs_2CO_3$, catalytic CuI, and 1,10-phenanthroline under microwave conditions and was applied to the synthesis of benzoxazoles. These copper-catalyzed approaches complement existing strategies for benzoxazole synthesis, which typically utilize 2-aminopheonls as precursors. R. D. Viirre, G. Evindar, R. A. Batey, *J. Org. Chem.*, 2008, 73, 3452-3459.

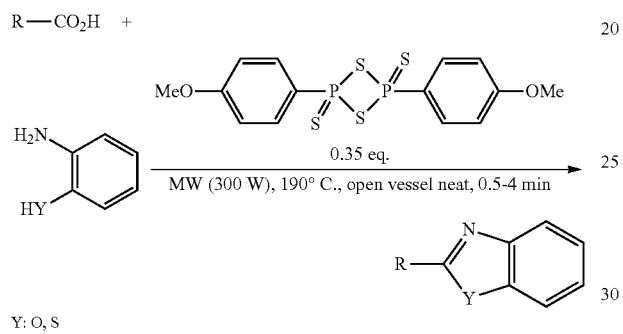

Y: O, S

In the above process, Lawesson's reagent is an efficient promoter in the solvent-free microwave-assisted synthesis of 2-substituted benzoxazoles and benzothiazoles from carboxylic acids and 2-aminophenol or 2-aminothiophenol, respectively. Various aromatic, heteroaromatic and aliphatic carboxylic acids react under the conditions developed with good yields. J. A. Seijas, M. P. Vázquez-Tato, M. R. Carballido-Reboredo, J. Crecente-Campo, L. Romar-López, *Synlett*, 2007, 313-316.

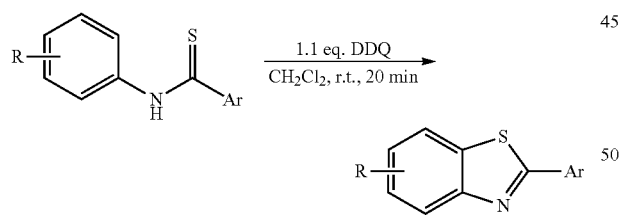

In the above process, various benzothiazoles were synthesized by the intramolecular cyclization of thioformanilides using 2,6-dichloro-3,5-dicyano-1,4-benzoquinone (DDQ) in dichloromethane at ambient temperature in high yields. D. S. Bose, M. Idrees, B. Srikanth, *Synthesis*, 2007, 819-823.

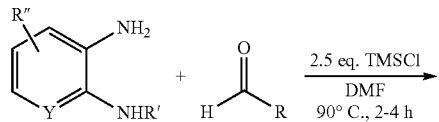

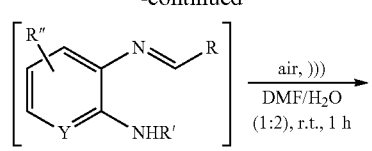

Y: CH, N

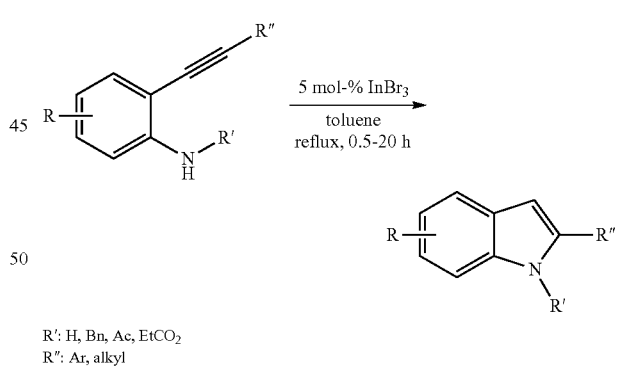

In the above process, a set of benzimidazoles, 3H-imidazo[4,5-b]pyridines, purines, xanthines and benzothiazoles was readily prepared from (hetero)aromatic ortho-diamines or ortho-aminothiophenol and aldehydes using chlorotrimethylsilane in DMF as a promoter and water-acceptor agent, followed by oxidation with air oxygen. S. V. Ryabukhin, A. S. Plaskon, D. M. Volochnyuk, A. A. Tolmachev, *Synthesis*, 2006, 3715-3726.

R': H, Bn, Ac, $EtCO_2$
R": Ar, alkyl

In the above process, indium-catalyzed cyclization of 2-ethynylanilines produced various polyfunctionalized indole derivatives in good yields for substrates having an alkyl or aryl group on the terminal alkyne. In contrast, substrates with a trimethylsilyl group or without substituent on the triple bond afforded polysubstituted quinoline derivatives in good yields via an intermolecular dimerization. N. Sakai, K. Annaka, A. Fujita, A. Sato, T. Konakahara, *J. Org. Chem.*, 2008, 73, 4160-4165.

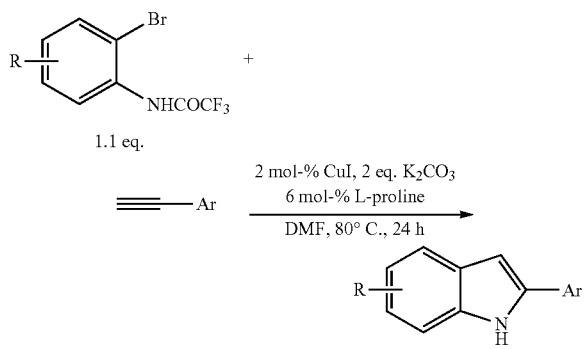

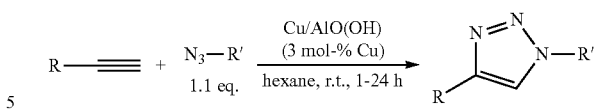

In the above process, immobilized copper nanoparticles in aluminum oxyhydroxide fiber showed high catalytic activity for the cycloaddition of various alkynes to azides at room temperature. The catalyst can be recycled up to five times without significant loss of activity. I. S. Park, M. S. Kwon, Y. Kim, J. S. Lee, J. Park, *Org. Lett.*, 2008, 10, 497-500; or In the above process, cross-coupling of 1-alkynes with vinyl iodides catalyzed by CuI/N,N-dimethylglycine affords conjugated enynes in good to excellent yields. Heating a mixture of 2-bromotrifluoroacetanilide, 1-alkyne in the presence of CuI/L-proline leads to the formation of the corresponding indole. F. Liu, D. Ma, *J. Org. Chem.*, 2007, 72, 4844-4850.

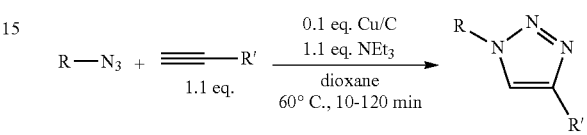

In the above process, highly efficient click chemistry between azides and terminal alkynes can be heterogeneously catalyzed by copper nanoparticles mounted within the pores of activated charcoal. Reactions can be accelerated with stoichiometric Et$_3$N or by increasing the reaction temperature using microwave irradiation.

B. H. Lipshutz, B. R. Taft, *Angew. Chem. Int. Ed.*, 2006, 45, 8235-8238; or

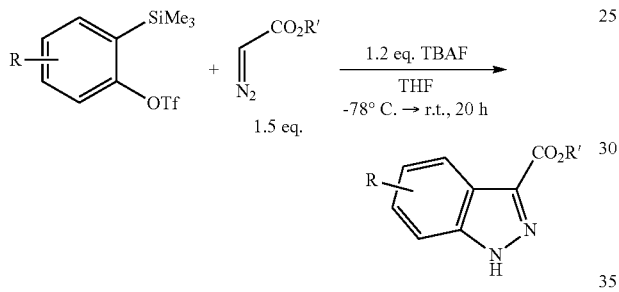

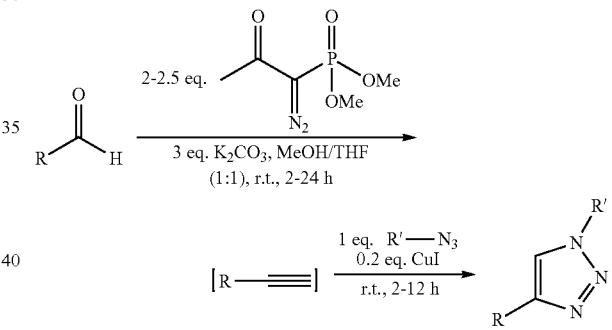

In the above process, the [3+2] cycloaddition of a variety of diazo compounds with o-(trimethylsilyl)aryl triflates in the presence of CsF or TBAF at room temperature provides a very direct, efficient approach to a wide range of potentially biologically and pharmaceutically interesting substituted indazoles in good to excellent yields under mild reaction conditions. Z. Liu, F. Shi, P. D. G. Martinze, C. Raminelli, R. C. Larock. *J. Org. Chem.*, 2008, 73, 219-226

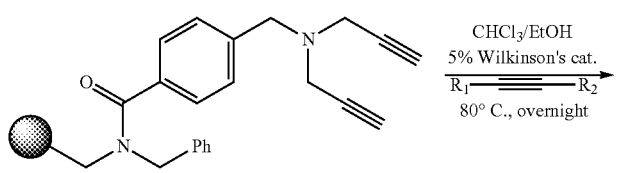

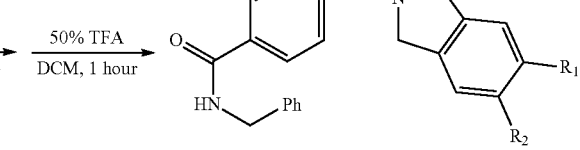

In the above process, an efficient solid-phase synthesis of isoindolines is reported. The key reaction step is a rhodium-catalyzed [2+2+2] cycloaddition of alkynes to give isoindolines in good yield. Q. Sun, X. Zhou, K. Islam, D. J. Kyle, *Tetrahedron Lett.*, 2001, 42(37), 6495-97.

For isoindol-1-one derivatives, processes as disclosed in Hyu Ji Lee, et al., *Bioorg. Med. Chem. Lett.*, 2008, 18(5), 1628-31 can be used.

Synthesis of 1,2,3-triazoles of formula (III) may be achieved using a variety of processes that are well-known to those of ordinary skill in the art, including (but not limited to) the following processes:

The above process provides a reliable and operationally simple one-pot reaction for a one-carbon homologation of various aldehydes followed by Cu-catalyzed azide-alkyne click chemistry gives 1,4-disubstituted 1,2,3-triazoles in good yields without the need for isolation of the alkyne intermediates. D. Luvino, C. Amalric, M. Smietana, J.-J. Vasseur, *Synlett*, 2007, 3037-3041.

Synthesis of compounds of formulae (IV)(A) and (IV)(B) (e.g. pyrazoles, isoxazoles, imidazolines, imidazolidones, oxazolines, and oxazolidinones) may be achieved using a variety of processes that are well-know to those of ordinary skill in the art, including (but not limited to) the following processes:

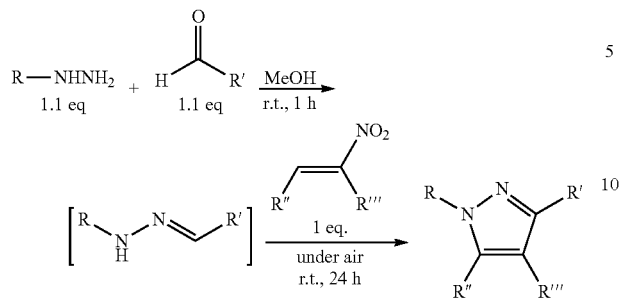

The above process provides a regioselective one-pot synthesis of substituted pyrazoles from N-monosubstituted hydrazones and nitroolefins gives products in good yields. A key nitropyrazolidine intermediate is characterized and a plausible mechanism is proposed. X. Deng, N. S. Mani, *Org. Lett.*, 2006, 8, 3505-3508.

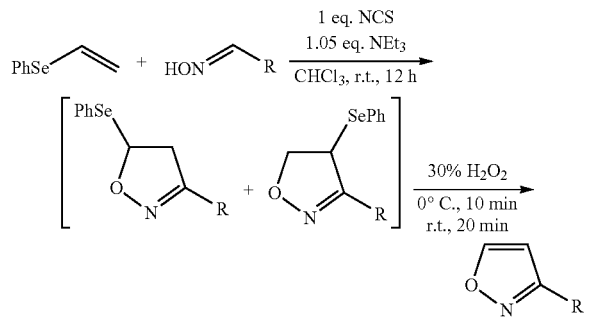

In the above process, a 1,3-dipolar cycloaddition of phenyl vinylic selenide to nitrile oxides and subsequent oxidation-elimination furnished 3-substituted isoxazoles with good yields in a one-pot, two-step transformation. S.-R. Sheng, X.-L. Liu, Q. Xu, C.-S. Song, *Synthesis*, 2003, 2763-2764.

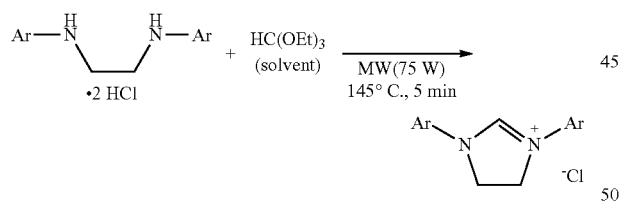

The above process provides a very simple and efficient, microwave-assisted procedure for the synthesis of 1,3-diarylimidazolinium chlorides by cyclization of N,N'-diarylethylenediamines dihydrochlorides with triethyl orthoformate. A. Aidouni, A. Demonceau, L. Delaude, *Synlett*, 2006, 493-495.

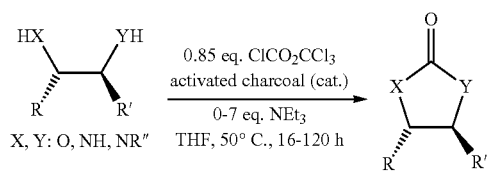

In the above process, an efficient, versatile and practical gram-scale preparation of oxazolidinone, imidazolidinone and dioxolanone is achieved. N. Alouane, A. Boutier, C. Baron, E. Vrancken, P. Mangeney, *Synthesis*, 2006, 860-864.

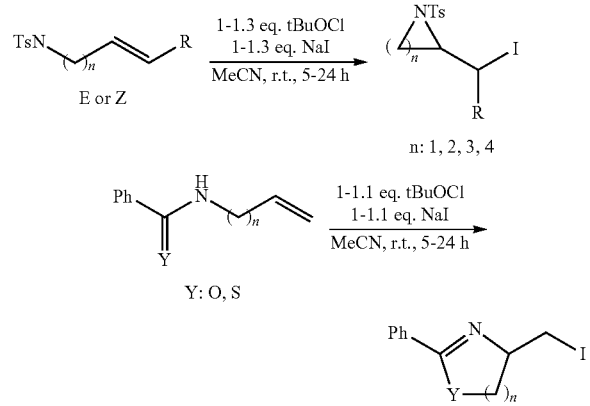

In the above process, tert-Butyl hypoiodite is a mild and powerful reagent for the cyclization of N-alkenylamides leading to various N-heterocycles. N-alkenylsulfonamides gave three- to six-membered saturated N-heterocycles in good yields, whereas alkenylbenzamide derivatives afforded N—, O— or N—, S-heterocycles. S. Minakata, Y. Morino, Y. Oderaotoshi, M. Komatsu, *Org. Lett.*, 2006, 8, 3335-3337.

The aforementioned reactions schemes are illustrative, and those of ordinary skill in the art are aware of and may readily utilize alternative processes well known in the art for making the compounds according to the present invention described above.

Compound Characterization

The identity of all assayed compounds was confirmed by $^1$H-NMR, $^{13}$C-NMR, and high-resolution mass spectrometry (HRMS), and elemental analysis. The purity of all samples was demonstrated by high performance liquid chromatography. Examples of NMR spectra and HRMS data are given below for compounds 10 and 14.

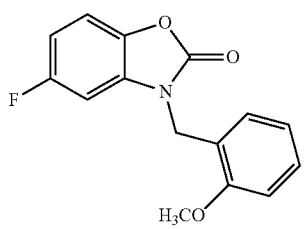

$^1$HNMR (500 MHz, CDCl$_3$), δ 7.32-7.26 (m, 2H), 7.10-7.08 (m, 1H), 6.95 (m, 2H), 6.77-6.73 (m, 2H), 5.0 (s, 2H), 3.89 (s, 3H); $^{13}$CNMR (125 MHz, CDCl$_3$), δ 160.44, 158.52, 157.24, 155.23, 138.66, 138.64, 130.06, 130.02, 122.50, 121.03, 110.72, 110.38, 110.30, 108.56, 108.36, 98.18, 97.94, 55.50, 41.38 HRMS (ESI-TOF) calcd for C$_{15}$H$_{12}$FNO$_3$ [M+H]$^+$ 274.0873. found 274.0873.

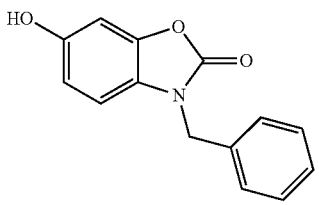

14

¹HNMR (500 MHz, CDCl₃), δ 7.33-7.28 (m, 5H), 6.78 (dd, j=8.5, 3 Hz, 1H), 6.73 (d, j=1 Hz, 1H), 6.58-6.56 (m, 1H); ¹³CNMR (125 MHz, MeOH-d₄), δ 156.89, 155.26, 144.67, 136.78, 129.91, 129.12, 128.63, 124.50, 111.60, 110.72, 99.33, 46.67. HRMS (ESI-TOF) calcd for $C_{14}H_{11}NO_3$ [M+H]⁺ 242.0811. found 242.0811.

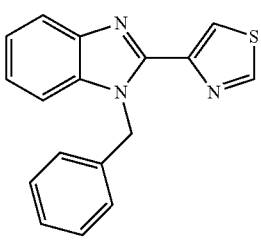

17

¹HNMR (500 MHz, CDCl₃), δ 8.65 (d, j=2 Hz, 1H), 8.35 (m, j 1H), 7.60 (d, j=8 Hz, 1H), 7.10-6.92 (m, 8H), 5.86 (s, 2H); ¹³CNMR (125 MHz, CDCl₃), δ 153.06, 148, 147.05, 143.19, 137.20, 136.11, 129.06, 128.78, 127.61, 126.83, 123.39, 122.94, 121.44, 119.90, 110.76, 48.67; MS (m/z): (M+1)=291.87 (100%)

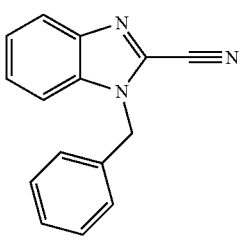

18

¹HNMR (500 MHz, CDCl₃), δ 7.80 (d, j=7 Hz, 1H), 7.35 (m, 6H), 7.18 (m, 2H), 5.50 (s, 2H); ¹³CNMR (125 MHz, CDCl₃), δ 142.96, 134.32, 134.24, 129.38, 128.92, 127.30, 126.87, 126.68, 124.68, 121.99, 111.38, 111.0, 49.29; MS (m/z): (M+1)=300.0 (100%).

Representative Procedure for Compound 098 Table 1

Compound 098 Table 1

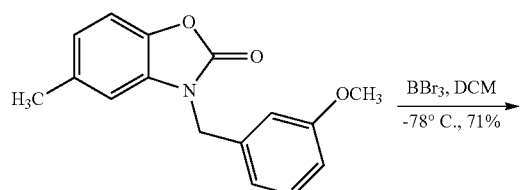

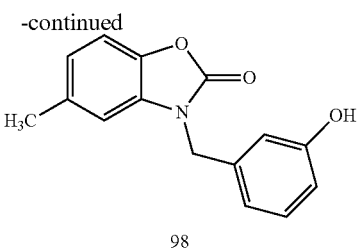

98

To a solution of 5 (7.42 g, 27.6 mmol) in DCM (500 ml) was added BBr₃ (138 mL, 138 mmol) at −78° C. as 1M DCM solution and stirred to rt for 2 hr. The reaction was quenched with aq.NaHCO₃ followed by dilution with DCM, to this water and brine wash was given and concentrated. The crude residue was purified by column chromatography, eluting with Hexanes:AcOEt (4:1) on silica gel to give compound 098 (098 of Table 1) as a white solid (2.00 g, 71%). ¹HNMR (400 MHz, MeOH-d₄), δ 6.94 (t, j=7.6 Hz, 1H), 6.80 (d, j=8.4 Hz, 1H), 6.63-6.56 (m, 3H), 6.55 (d, j=8.4 Hz, 1H), 5.85 (s, 1H), 4.65 (s, 2H), 2.06 (s, 3H); ¹³CNMR (125 MHz, CDCl₃), δ 156.66, 155.56, 140.82, 136.54, 134.16, 130.85, 130.31, 123.29, 119.78, 115.62, 114.54, 109.83, 109.67, 45.95, 21.63

The invention is described further in the following description of biological assays and examples, which are illustrative and are not limiting.

Biological Assays

Two principal assays have been performed, one for inhibition of MIF tautomerase activity and the other for MIF-CD74 binding. The tautomerase assay monitored the keto/enol interconversion for p-hydroxyphenylpyruvate (HPP) catalyzed by MIF (Stamps, S. L., (2000), Mechanism of the Phenylpyruvate Tautomerase Activity of Macrophage Migration Inhibitory Factor: Properties of the P1G, P1A, Y95F, and N97A Mutants *Biochemistry* 39, 9671-9678). The related procedure used dopachrome as the substrate, as has been used previously to identify MIF inhibitors including ISO-1 (Lubetsky, J. B. (2002), The tautomerase active site of macrophage migration inhibitory factor is a potential target for discovery of novel anti-inflammatory agents. *J. Biol. Chem.* 277, 24976-24982). However, it is noted that a compound may appear active in one tautomerase assay and not in the other; in fact, ISO-1 is inactive in the HPP tautomerase assay. The biologically more significant assay is a "capture" assay using immobilized, recombinant MIF receptor ectodomain and biotinylated recombinant MIF (Leng, L., et al. (2003), MIF signal transduction initiated by binding to CD74. *J. Exp. Med.* 197, 1467-1476). This allows measurement of the inhibition or enhancement of the binding of MIF to its receptor induced by an addend.

Two additional assays were performed on compounds according to the present invention. In the first, MIF-dependent signal transduction in cells as evidenced by a reduction in ERK1/2 phosphorylation and its inhibitory action is compared to the known small molecule MIF antagonist, isoxazoline-1 following the assay reported in Leng L., Metz C, Fang Y, Xu J, Donnelly S, Baugh J, Delonery T, Chen Y, Mitchell R A, and Bucala R. 2003. MIF Signal Transduction Initiated by Binding to CD74. *J Exp Med* 197, 1467-1476.

One particular compound, compound 098 of Table 1, showed significant inhibitory action in this assay.

In the second additional assay, compounds of the present invention were tested to determine whether the compound inhibits the growth of an ovarian cancer cell line, following the assay reported in Kim K H, Xie Y, Tytler E M, Woessner R, M or G, Alvero A B. 2009. KSP inhibitor ARRY-520 is used as a substitute for Paclitaxel in Type I ovarian cancer cells. J Transl Med. 7:63. Several compounds show significant activity in the ovarian cancer assay including MIF098 (Table 1), MIF108 (in Table 4), and MIF112 (37 in Table 3) and MIF112 in Table 6)

Sample Activity Data

Assay results are provided in Table 1, below for sixteen compounds in the N-benzyl-benzooxazolone series B of the invention. Strikingly potent compounds have been found for both inhibition of MIF-CD74 binding and MIF tautomerase activity. Table 1 also notes that ISO-1 is inactive in the capture assay, while a biologically-neutralizing anti-MIF antibody is a 0.4 μM inhibitor. As noted previously (Senter, P. D., et al. (2002), Inhibition of macrophage migration inhibitory factor (MIF) tautomerase and biological activities by acetaminophen metabolites. *Proc. Nat. Acad. Sci. USA* 99, 144-9 ("Senter 2002")), a compound may be potent in one assay and relatively inactive in the other, e.g., compound 15, while some are potent in both, e.g., compound 1.

Table 1 also notes that ISO-1 is inactive in the capture assay, while a biologically neutralizing anti-MIF antibody is a 0.4 μM inhibitor. Another reference compound, 4-iodo-6-phenylpyrimidine (4-IPP), also is inactive in the capture assay, but is a 4.5-μM inhibitor in the HPP tautomerase assay. 4-IPP has recently been licensed by Advanced Cancer Therapeutics from the University of Louisville; the press release notes that "4-IPP, a novel small molecule compound, exhibits anti-tumor activity by blocking tumor-specific angiogenesis, and thus far has demonstrated a favorable safety profile in laboratory studies.

As a macrophage migration inhibitory factor (MIF), this chemokine promotes multiple pro-angiogenic growth factors (VEGF and IL-8) and contributes to tumor cell division, metastases and tumor vascularization (i.e., angiogenesis). The University of Louisville researchers have shown in the laboratory that 4-IPP could serve as front-line therapy against bulk tumors and reduce the risk of recurrence of primary tumors or eventual metastasis. In addition, while initially targeted for development in oncology, 4-IPP has subsequently been evaluated for its potential to address various unmet medical needs in autoimmune related diseases such as Rheumatoid Arthritis, Lupus and Multiple Sclerosis." We view 4-IPP as an unattractive drug candidate owing to anticipated off-target activities associated with the highly electrophilic 4-iodo-pyrimidine subunit.

The following comprises tabular summaries of additional data relating to inhibition of MIF-CD74 binding and MIF tautomerase activity (HPP) by additional representative compounds of the invention as well as reference compounds. Various portions of the data in these tables were determined using techniques as described above. The tables also provide other criteria and values relevant to characterization of representative compounds of the invention for purposes of determining structure-activity relationships and other features.

TABLE 1

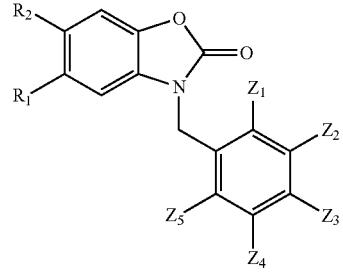

B

Assay Results for Inhibition of MIF-CD74 Binding and MIF Tautomerase Activity (HPP) by Benzooxazolones of structure B, above ($Z_4 = Z_5 = H$) in μM.

| Cmpd | $R_1$ | $R_2$ | $Z_1$ | $Z_2$ | $Z_3$ | MIF-CD74 $IC_{50}$ | HPP $IC_{50}$ | HPP Max. Inhib. |
|---|---|---|---|---|---|---|---|---|
| 1 | $CH_3$ | H | H | H | H | 1.5 | 0.5 | |
| 2 | H | $CH_3$ | H | H | H | | 3.4 | |
| 3 | $OCH_3$ | H | H | $OCH_3$ | H | 200 | | 41% |
| 4 | $CH_2OH$ | H | H | $OCH_3$ | H | 500 | | 44% |
| 5 | $CH_3$ | H | H | $OCH_3$ | H | 300 | 2.9 | |
| 6 | $CH_3$ | H | $OCH_3$ | H | H | 0.09 | | 35% |
| 7 | $CH_3$ | H | $OCH_3$ | $OCH_3$ | H | 7.0 | | 32% |
| 8 | F | H | H | H | H | 25 | 1.0 | |
| 9 | F | H | H | H | $OCH_3$ | >1000 | | 35% |
| 10 | F | H | $OCH_3$ | H | H | | | 17% |
| 11 | OH | H | H | $OCH_3$ | H | 30 | 26 | |
| 12 | OH | H | $OCH_3$ | H | H | >1000 | 30 | |
| 13 | OH | H | $OCH_3$ | $OCH_3$ | H | 300 | 2.1 | |
| 14 | H | OH | H | H | H | >1000 | | 28% |
| 15 | H | OH | H | H | $OCH_3$ | 3.0 | | 23% |
| 16 | H | OH | $OCH_3$ | H | H | | | 15% |
| 098 | $CH_3$ | H | H | OH | H | | 0.01 | |

TABLE 1-continued

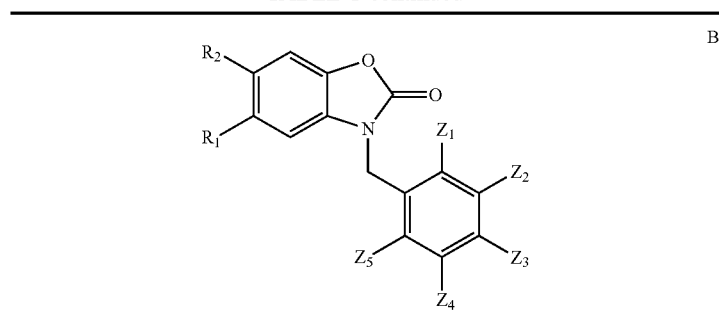

Assay Results for Inhibition of MIF-CD74 Binding and MIF Tautomerase Activity (HPP) by Benzooxazolones of structure B, above ($Z_4 = Z_5 = H$) in µM.

| Cmpd | $R_1$ | $R_2$ | $Z_1$ | $Z_2$ | $Z_3$ | MIF-CD74 $IC_{50}$ | HPP $IC_{50}$ | HPP Max. Inhib. |
|---|---|---|---|---|---|---|---|---|
| ISO-1 | | | | | | >10000 | >10000 | |
| 4-IPP | | | | | | >10000 | 4.5 | |
| anti-MIF | | | | | | 0.4 | | |

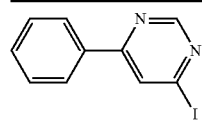

4-IPP

Additional data are provided in Table 2 for illustrative active compounds in multiple other series discussed above; the specific structures are illustrated below. It is noted that for some compounds including compound 25 we observe agonist behavior, i.e., an enhancement of MIF-CD74 binding upon addition of the compound.

TABLE 2

Assay Results for Inhibition of MIF-CD74 Binding and MIF Tautomerase Activity (HPP) in µM.

| Cmpd | MIF-CD74 $IC_{50}$ | HPP $IC_{50}$ | HPP Max. Inhib. |
|---|---|---|---|
| 17 | | | 40% |
| 18 | | | 36% |

TABLE 2-continued

Assay Results for Inhibition of MIF-CD74 Binding and MIF Tautomerase Activity (HPP) in µM.

| Cmpd | MIF-CD74 $IC_{50}$ | HPP $IC_{50}$ | HPP Max. Inhib. |
|---|---|---|---|
| 19 | | | 38% |
| 20 | | 510 | |
| 21 | 4.0 | 3.0 | |
| 22 | 2.5 | | |
| 23 | 1500 | | |
| 24 | 5000 | | |
| 25 | agonist | 4.2 | |

TABLE 3

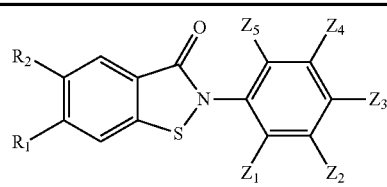

Assay Results for In48hibition of MIF-CD74 Binding and MIF Tautomerase Activity (HPP) by Benzothiazolones of the above structure ($Z_4 = Z_5 = H$) in µM.

| Cmpd | $R_1$ | $R_2$ | $Z_1$ | $Z_2$ | $Z_3$ | HPP $IC_{50}$ | Capture % Max. Inhib. | Capture IC50 |
|---|---|---|---|---|---|---|---|---|
| 26 | F | H | H | H | Cl | 4.2 | | agonist |
| 27 | F | H | H | H | $OCH_3$ | 6.2 | NA | |
| 28 | F | H | H | $OCH_3$ | H | 25 | NA | |
| 29 | F | H | H | $CH_2OH$ | H | 4.8 | 8 | |
| 30 | H | F | H | H | Cl | 2.8 | 7 | |

TABLE 3-continued

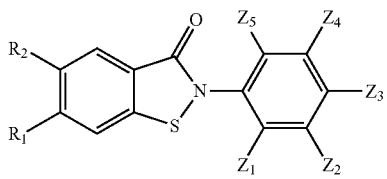

Assay Results for In48hibition of MIF-CD74 Binding and MIF Tautomerase Activity (HPP) by Benzothiazolones of the above structure ($Z_4 = Z_5 = H$) in μM.

| Cmpd | $R_1$ | $R_2$ | $Z_1$ | $Z_2$ | $Z_3$ | HPP $IC_{50}$ | Capture % Max. Inhib. | Capture IC50 |
|---|---|---|---|---|---|---|---|---|
| 31 | H | Cl | OCH$_3$ | H | H | 6.6 | 7 | |
| 32 | H | F | H | OH | H | 5.9 | 13 | |
| 33 | F | H | H | CH$_2$OAc | H | 2.3 | 12 | |
| 34 | H | NO$_2$ | H | H | Cl | 6.2 | 11 | |
| 35 | H | CF$_3$ | H | H | Cl | 8.5 | 12 | |
| 36 | Br | H | H | H | Cl | 11 | 10 | |
| 37 | CN | H | H | H | Cl | 3.1 | 16 | |
| 38 | H | F | H | OCH$_3$ | H | 8 | | agonist |
| 39 | H | Br | H | H | Cl | 7.9 | NA | |
| 40 | H | CN | H | H | Cl | 19 | | agonist |

TABLE 4

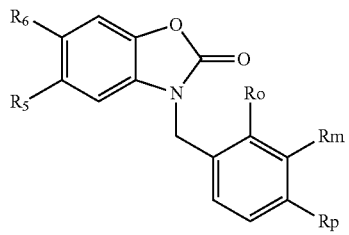

Assay Results for Inhibition of MIF-CD74 Binding and MIF Tautomerase Activity (HPP) by Benzooxazolones of above structure in μM

| cmpd | | R5 | R6 | Ro | Rm | Rp | CD74 % MaxInhib | CD74 IC50 | HPP IC50 | HPP Max Inhib |
|---|---|---|---|---|---|---|---|---|---|---|
| 1 | MIF-026 | CH3 | H | H | H | H | 24 @ 1.87 | 1.5 | 0.5 | |
| 5 | MIF-046 | CH3 | H | H | OCH3 | H | 42 @ 1.87 | 300 | 2.9 | |
| 7 | MIF-047 | CH3 | H | OCH3 | OCH3 | H | 36 @ 1.87 | 7 | | 32% @ 0.1 |
| 6 | MIF-048 | CH3 | H | OCH3 | H | H | 43 @ 0.039 | 0.09 | | 35% @ 25 |
| 3 | MIF-049 | OCH3 | H | H | OCH3 | H | 36 @ 1.87 | 200 | | 41% @ >500 |
| 11 | MIF-050 | OH | H | H | OCH3 | H | 24 @ 1.87 | 30 | 26 | |
| 13 | MIF-051 | OH | H | OCH3 | OCH3 | H | 34 @ 1.87 | 300 | 2.1 | |
| 12 | MIF-052 | OH | H | OCH3 | H | H | 27 @ 0.078 | >1000 | 30 | |
| 4 | MIF-053 | CH2OH | H | H | OCH3 | H | 27 @ 0.039 | 500 | | 44% @ 200 |
| 8 | MIF-054 | F | H | H | H | H | 36 @ 0.039 | 25 | 1 | |
| 9 | MIF-055 | F | H | H | H | OCH3 | 14 @ 0.039 | >1000 | | 35% @ 50 |
| 10 | MIF-067 | F | H | OCH3 | H | H | 33 @ 0.039 | | | 17% |
| 15 | MIF-056 | H | OH | H | H | OCH3 | 27 @ 0.078 | 3 | | 23% @ 500 |
| 16 | MIF-068 | H | OH | OCH3 | H | H | 18 @ 0.039 | | | 15% |
| 14 | MIF-057 | H | OH | H | H | H | 22 @ 0.039 | >1000 | | 28% @ 5 |
| 2 | MIF-059 | H | CH3 | H | H | H | 25 @ 1.87 | | 3.4 | |
| | MIF-080 | CH3 | H | H | H | OCH3 OCH2CH2— | 32 @ 0.12 | | | NA |
| | MIF-081 | CH3 | H | H | H | OCH3 OCH2CH2— | 25 @ 0.12 | | | 34% @ 1000 |
| | MIF-085 | H | OH | H | H | OCH3 | 34 @ 0.078 | | | 8% @ 25 |
| | MIF-091 | CH3 | H | H | H | F | 29 @ 0.94 | | 325 | |
| | MIF-092 | CH3 | H | H | H | OH | 10 @ 0.078 | | | 173% @ 0.05 |
| | MIF-093 | CH3 | H | H | F | H | 14 @ 1.87 | | | 265% @ 5 |
| | MIF-097 | H | H | H | H | H | 18 @ 1.87 | | 21 | |
| | MIF-098 | CH3 | H | H | OH | H | 13 @ 0.0078 | | 0.01 | |
| | MIF-099 | OH | H | H | H | H | 23 @ 1.87 | | 720 | |
| | MIF-107 | CH3 | H | H | NH2 | H | 27 @ 3.87 | | | 31% @ 0.03 |
| | MIF-108 | F | H | H | OH | H | 18 @ 0.078 | | | 32% @ 0.5 |
| | MIF-116 | H | F | H | OH | H | | | agonist | agonist |

TABLE 4-continued

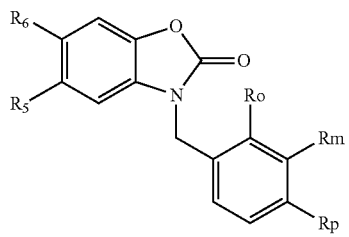

Assay Results for Inhibition of MIF-CD74 Binding and MIF Tautomerase Activity (HPP) by Benzooxazolones of above structure in μM

| cmpd | R5 | R6 | Ro | Rm | Rp | CD74 % MaxInhib | CD74 IC50 | HPP IC50 | HPP Max Inhib |
|---|---|---|---|---|---|---|---|---|---|
| MIF-117 | F | H | H | OCH3 | H | 17 @ 0.24 | | | agonist |
| MIF-118 | H | F | H | OCH3 | H | 15 @ 0.078 | | | 35% @ 500 |
| MIF-119 | CH3 | H | H | 3,5-dimethoxy | H | 11 @ 3.76 | | | 17% @ 0.1 |
| MIF-139 | H | CH3 | H | OH | H | 10 @ 0.078 | | 0.0075 | |
| MIF-140 | CH3CH2 | H | H | OH | H | 19 @ 0.078 | | 2.5 | |
| MIF-145 | CH3 | | OCH2CH3 | | H | 45 @ 0.078 | | | 21 @ 1.0 |
| MIF-146 | CH3 | | OBu | | H | | 3.76 | 500 | |
| MIF-147 | CH3 | | OBn | | H | 47 @ 3.76 | | 325 | |
| MIF-148 | Cl | | | CN | H | 34 @ 0.47 | | | NA |
| MIF-149 | H | CH3 | | OCH3 | H | | | | 16 @ 3 |
| MIF-150 | CH3CH2 | | | OCH3 | H | | | | 13 @ 12 |
| MIF-151 | OH | | | OH | H | | | | 25 @ 0.1 |
| MIF-152 | CH3 | | | OCH2CH3 | H | 42 @ 1.87 | | | 20 @ 3 |
| MIF-153 | OCH3 | | | OH | H | 36 @ 1.87 | 0.08 | | |
| MIF-154 | CH3 | CH3 | | OCH3 | H | 43 @ 0.039 | 0.115 | | |
| MIF-157 | CH3 | | | m-OH, m'-OEt | | 36 @ 1.87 | | | |

Note:
all activities in micromolar (μM)

TABLE 5

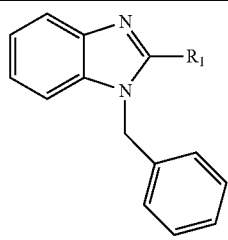

Assay Results for Inhibition of MIF-CD74 Binding and MIF Tautomerase Activity (HPP) by Benzimidazoles of above structure and Other Compounds in μM

| Compound | | R1 | CD74 % MaxInhib | CD74 IC50 | HPP IC50 | HPP Max Inhib |
|---|---|---|---|---|---|---|
| 17 | MIF-058 | 4-thiazole | 28 @ 0.039 | >1000 | | 40% at 5 |
| 19 | MIF-060 | (2-pyridinyl)methyl | 40 @ 1.87 | | | 38% |
| 18 | MIF-061 | nitrile | 20 @ 0.078 | | | 36% |
| | MIF-062 | amide | 25 @ 1.87 | | | 16% |
| | MIF-063 | N,N-dimethylamide | 27 @ 1.87 | | | 0% |
| | MIF-065 | N-methylamide | 16 @ 1.87 | | | 13% |
| | MIF-066 | CH3OCH2CH2 | 25 @ 1.87 | | | 18% |
| 20 | | | | | 510 | |
| 21 | | | | 4.0 | 3.0 | |
| 22 | | | | 2.5 | | |
| 23 | | | | 1500 | | |
| 24 | | | | 5000 | | |
| 25 | | | | agonist | 4.2 | |

TABLE 6

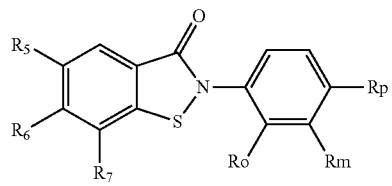

Assay Results for Inhibition of MIF-CD74 Binding and MIF Tautomerase Activity (HPP) by Benzothiazolones of above structure in μM

| Cmpd | R5 | R6 | R7 | Ro | Rm | Rp | HPP % MaxInhib | HPP IC50 | CD74 % MaxInhib | CD74 IC50 |
|---|---|---|---|---|---|---|---|---|---|---|
| MIF-044 | H | F | H | H | H | Cl | 4.2 | | agonist | |
| MIF-100 | H | F | H | H | H | OMe | 6.2 | | NA | |
| MIF-101 | H | F | H | H | OMe | H | 25 | | NA | |
| MIF-102 | H | F | H | H | CH2OH | H | 4.8 | | 8 | |
| MIF-103 | H | H | F | H | H | Cl | 2.8 | | 7 | |
| MIF-104 | H | H | Cl | H | H | Cl | 6.6 | | 7 | |
| MIF-105 | H | H | F | H | OH | H | 5.9 | | 13 | |
| MIF-106 | H | F | H | H | CH2OAc | H | 2.3 | | 12 | |
| MIF-109 | NO2 | H | H | H | H | Cl | 6.2 | | 11 | |
| MIF-110 | CF3 | H | H | H | H | Cl | 8.5 | | 12 | |
| MIF-111 | H | Br | H | H | H | Cl | 11 | | 10 | |
| MIF-112 | H | CN | H | H | H | Cl | 3.1 | | 16 | |
| MIF-113 | H | H | F | H | OMe | H | 8 | | agonist | |
| MIF-114 | Br | H | H | H | H | Cl | 7.9 | | NA | |
| MIF-115 | CN | H | H | H | H | Cl | 19 | | agonist | |
| MIF-132 | H | F | H | H | Cl | H | 5 | | 20 @ 0.078 | |
| MIF-133 | H | F | H | H | H | CN | 6.4 | | 49 @ 0.078 | |
| MIF-134 | H | F | F | H | H | Cl | 5.6 | | 11 @ 3.76 | |
| MIF-135 | H | F | H | H | CHO | H | 6 | | NA | |
| MIF-136 | H | F | H | H | CH2OMe | H | 2.4 | | NA | |
| MIF-141 | F | H | H | H | H | Cl | 5.6 | | agonist | |
| MIF-142 | F | H | H | H | H | OMe | 6.5 | | agonist | |
| MIF-143 | F | F | H | H | H | Cl | 4.9 | | agonist | |
| MIF-144 | F | H | H | H | OMe | H | 2.75 | | agonist | |

TABLE 7

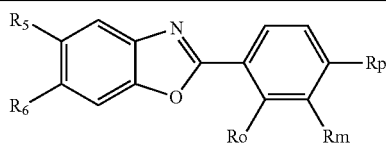

Assay Results for Inhibition of MIF-CD74 Binding and MIF Tautomerase Activity (HPP) by Benzoxazoles of above structure in μM

| Cmpd | R5 | R6 | Ro | Rm | Rp | HPP % MaxInhib | HPP IC50 | CD74 % MaxInhib | CD74 IC50 |
|---|---|---|---|---|---|---|---|---|---|
| MIF-120 | H | Cl | H | H | H | 13 @ 0.1 | | 11 @ 0.078 | |
| MIF-121 | H | Cl | H | H | Cl | 43 @ 500 mM | | 27 @ 0.078 | |
| MIF-122 | Cl | H | H | H | Cl | 31 @ 500 mM | | 13 @ 3.76 | |
| MIF-123 | H | CH3 | H | H | Cl | 14 @ 50 | | 26 @ 3.76 | |

TABLE 7-continued

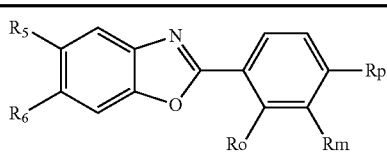

Assay Results for Inhibition of MIF-CD74 Binding and MIF Tautomerase Activity (HPP) by Benzoxazoles of above structure in μM

| Cmpd | R5 | R6 | Ro | Rm | Rp | HPP % MaxInhib | HPP IC50 | CD74 % MaxInhib | CD74 IC50 |
|---|---|---|---|---|---|---|---|---|---|
| MIF-124 | CH3 | H | H | H | Cl | 29 @ 1000 | | 11 @ 0.078 | |
| MIF-155 | H | H | H | H | Et | | | | |
| MIF-156 | H | H | H | H | nPr | | | | |

TABLE 8

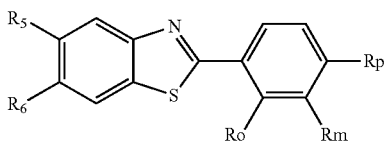

Assay Results for Inhibition of MIF-CD74 Binding and MIF Tautomerase Activity (HPP) by Benzothiazoles of above structure in μM

| Cmpd | R5 | R6 | Ro | Rm | Rp | HPP IC50 | CD74 % MaxInhib |
|---|---|---|---|---|---|---|---|
| MIF-137 | H | H | H | H | H | agonist | 18 @ 0.078 |
| MIF-138 | H | CH3 | H | H | H | agonist | 20 @ 0.078 |

TABLE 9

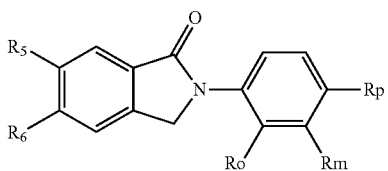

Assay Results for Inhibition of MIF-CD74 Binding and MIF Tautomerase Activity (HPP) by Isoindol-1-ones of above structure in μM

| Cmpd | R5 | R6 | Ro | Rm | Rp | HPP % MaxInhib | CD74 % MaxInhib |
|---|---|---|---|---|---|---|---|
| MIF-125 | F | H | H | H | Cl | 45 @ 500 mM | 19 @ 0.12 |
| MIF-126 | H | F | H | H | Cl | 32 @ 100 | 7 @ 0.078 |

TABLE 10

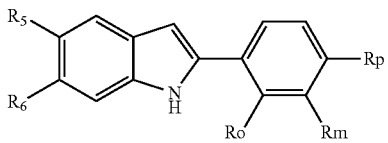

Assay Results for Inhibition of MIF-CD74 Binding and MIF Tautomerase Activity (HPP) by Indoles of above structure in μM

| Cmpd | R5 | R6 | Ro | Rm | Rp | HPP IC50 | CD74 % MaxInhib |
|---|---|---|---|---|---|---|---|
| MIF-127 | H | F | H | H | Cl | 240 | 22 @ 0.34 |
| MIF-128 | F | H | H | H | Cl | 280 | 20 @ 0.0039 |

TABLE 11

Assay Results for Inhibition of MIF-CD74 Binding and MIF Tautomerase Activity (HPP) by Benzopyrazoles of above structure in μM

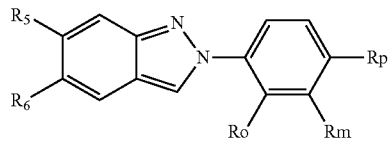

| Cmpd | R5 | R6 | Ro | Rm | Rp | HPP % MaxInhib | HPP IC50 | CD74 % MaxInhib |
|---|---|---|---|---|---|---|---|---|
| MIF-129 | H | F | H | H | Cl |  | 490 | 27 @ 0.12 |
| MIF-131 | F | H | H | H | Cl | 30 @ 500 mM |  | 29 @ 0.12 |

TABLE 12

Assay Results for Inhibition of MIF-CD74 Binding and MIF Tautomerase Activity (HPP) by Benzoimidazoles of above structure in μM

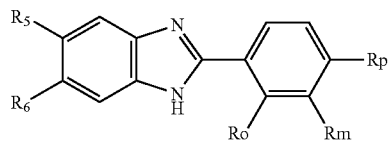

| Cmpd | R5 | R6 | Ro | Rm | Rp | HPP % MaxInhib | CD74 % MaxInhib |
|---|---|---|---|---|---|---|---|
| MIF-130 | F | H | H | H | Cl | 28 @ 500 mM | 21 @ 0.34 |

TABLE 13

Assay Results for Inhibition of MIF-CD74 Binding and MIF Tautomerase Activity (HPP) by Benzofurans of above structure in μM

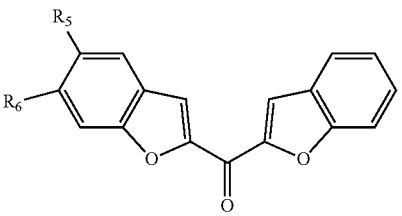

| Cmpd | R5 | R6 | CD74 % MaxInhib | CD74 IC50 | HPP IC50 | HPP Max Inhib |
|---|---|---|---|---|---|---|
| MIF-064 | H | H | 26 @ 0.058 |  | 510 |  |
| MIF-072 | OH | H | 9 @ 0.24 |  |  | 30% @ 1000 |
| MIF-073 | F | H | 17 @ 0.12 |  |  | 33 @ 700 |
| MIF-077 | H | CH3 | 16 @ 0.24 |  |  | 30% @ 1000 |
| MIF-078 | CH3 | H | NA |  |  | 47% @ 700 |

TABLE 14

Assay Results for Inhibition of MIF-CD74 Binding and MIF Tautomerase Activity (HPP) by Benzofurans of above structure in μM

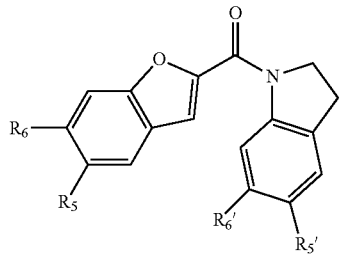

| Cmpd | R5 | R6 | R5' | R6' | CD74 % MaxInhib | CD74 IC50 | HPP IC50 | HPP Max Inhib |
|---|---|---|---|---|---|---|---|---|
| MIF-025 | H | H | H | H |  | 4 | 3 |  |
| MIF-082 | H | CH3 | H | H | 19% @ 0.24 |  | NA | NA |
| MIF-083 | H | OCH3 | H | H | 12% @ 0.078 |  |  | 33% @ 3 |
| MIF-088 | OCH3 | H | H | H | 30% @ 0.24 |  |  | 23% @ 5 |
| MIF-089 | F | H | H | H | 30% @ 0.12 |  |  | 19% @ 1 |
| MIF-094 | H | H | CH3 | H | 33% @ 0.95 |  | 760 |  |
| MIF-095 | H | H | H | CH3 | 33% @ 0.039 |  | 910 |  |
| MIF-096 | H | H | F | H | 19% @ 1.87 |  | 1360 |  |

TABLE 15

Assay Results for Inhibition of MIF-CD74 Binding and MIF Tautomerase Activity (HPP) by Benzofurans of above structure in μM

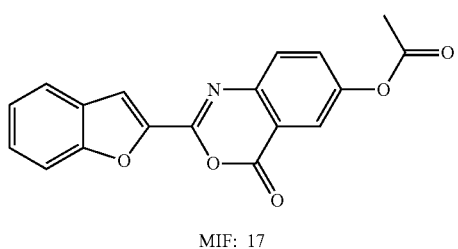 [SMILES: CC(=O)Oc1ccc2nc(-c3cc4ccccc4o3)oc(=O)c2c1]

MIF: 17

| Cmpd | CD74 IC50 | HPP IC50 |
|---|---|---|
| MIF-017 | 2.5 | 730 |

TABLE 16

Assay Results for Inhibition of MIF-CD74 Binding and MIF Tautomerase Activity (HPP) by Benzofurans of above structure in μM

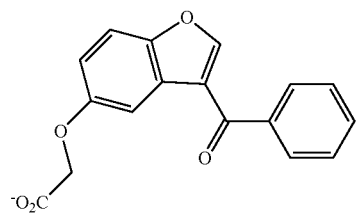

MIF022

| Cmpd | CD74 IC50 |
|---|---|
| MIF-022 | 1500 |

TABLE 17

Assay Results for Inhibition of MIF-CD74 Binding and MIF Tautomerase Activity (HPP) by Benzofurans of above structure in μM

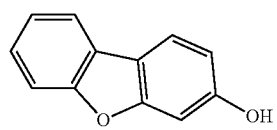 [SMILES: Oc1ccc2c(c1)oc1ccccc12]

| Cmpd | CD74 IC50 |
|---|---|
| MIF-039 | 900 |

TABLE 18

Assay Results for Inhibition of MIF-CD74 Binding and MIF Tautomerase Activity (HPP) by Triazoles

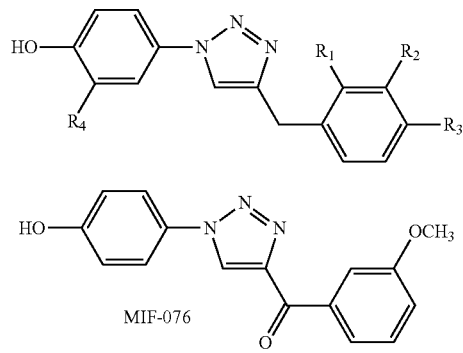

| | HPP | | | | CD74 C74 % MaxInhib | CD74 IC50 | CD74 HPP HPP IC50 | HPP Max Inhib |
|---|---|---|---|---|---|---|---|---|
| Cmpd | R1 | R2 | R3 | R4 | | | | |
| MIF-003 | H | H | H | H | | 3.5 | | |
| MIF-069 | H | H | H | F | 14% @ 0.0078 | | 760 | |
| MIF-070 | OCH3 | H | H | H | 14% @ 0.0078 | | | 35% @ 1000 |
| MIF-071 | OH | H | H | H | 9% @ 0.24 | | 1000 | |
| MIF-074 | H | OCH3 | H | H | 8% @ 0.24 | | | 40% @ 1000 |
| MIF-075 | H | OH | H | H | NA | | NA | |
| MIF-076 | see Figure above | | | | 12% @ 0.0078 | | 790 | |
| MIF-079 | H | CH3 | H | H | 30% @ 0.078 | | 475 | |
| MIF-084 | OCH3 | OCH3 | H | H | NA | | 530 | |
| MIF-086 | H | H | OCH3 | H | 36% @ 0.078 | | 65 | |
| MIF-087 | H | H | OH | H | 23% @ 0.078 | | 690 | |
| MIF-090 | H | OCH3 | OCH3 | H | 22% @ 0.078 | | 70 | |

TABLE 19

Assay Results for Inhibition of MIF-CD74 Binding and MIF Tautomerase Activity (HPP) by Triazoles as Depicted Above

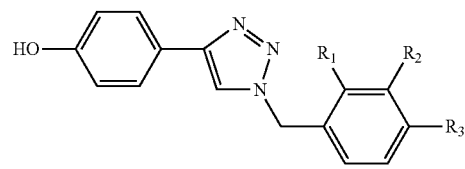

| Cmpd | R1 | R2 | R3 | % Bound | CD74 % MaxInhib | CD74 IC50 | HPP IC50 |
|---|---|---|---|---|---|---|---|
| MIF-002 | H | H | H | 96 | | 6000 | |
| MIF-004 | H | H | OCH3 | 94 | | na | |
| MIF-005 | H | OCH3 | H | 67 | | 100 | |
| MIF-031 | H | CH3 | H | 100 | | na | |
| MIF-032 | CH3 | H | H | 100 | | na | |
| MIF-033 | OCH3 | H | H | | | agonist | agonist |
| MIF-034 | OCH3 | OCH3 | H | | | 1.2 | 0.5-1.0 |
| MIF-036 | H | COOCH3 | H | | | 1.2 | 2.5 |
| MIF-037 | H | COOH | H | 70-90 | | na | |

TABLE 20

Assay Results for Inhibition of MIF-CD74 Binding and MIF Tautomerase Activity (HPP) by Triazoles as Depicted Above

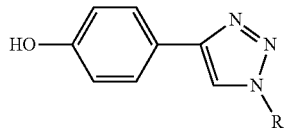

| Cmpd | R | CD74 % MaxInhib | CD74 IC50 | HPP IC50 |
|---|---|---|---|---|
| MIF-006 | 1-Np | | na | |
| MIF-007 | 3-Py | | na | 970 |
| MIF-008 | 4-IsoQ | | na | 32 |
| MIF-030 | 3-PyCH2 | | na | |
| MIF-035 | 2-PyCH2 | | 300 | |

TABLE 21

Assay Results for Inhibition of MIF-CD74 Binding and MIF Tautomerase Activity (HPP) by Triazoles as Depicted Above

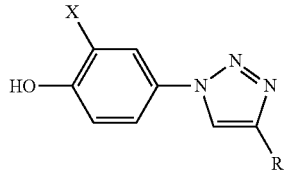

| Cmpd | R | IC50 | HPP IC50 |
|---|---|---|---|
| MIF-013 | 1-Np | Na | |
| MIF-020 | 3-Py | Agonist | agonist |
| MIF-021 | 4-Iso-Q | Agonist | agonist |

Np = naphthyl
Py = pyridinyl
Iso-Q = isoquinolinyl

TABLE 22

Assay Results for Inhibition of MIF-CD74 Binding and MIF Tautomerase Activity (HPP) by Indole as Depicted Above

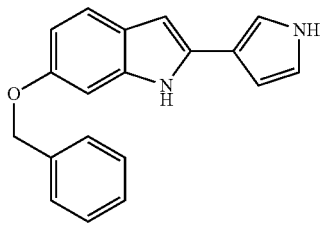

MIF-001

| Cmpd | CD74 IC50 |
|---|---|
| MIF-001 | 5000 |

TABLE 23

Assay Results for Inhibition of MIF-CD74 Binding and MIF Tautomerase Activity (HPP) by Phenyl Substituted Pyrazole as Depicted Above

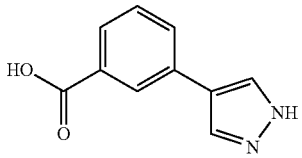 [SMILES: O=C(O)c1cccc(-c2cn[nH]c2)c1]

| Cmpd | CD74 IC50 |
|---|---|
| MIF-045 | 15 |

TABLE 24

Assay Results for Inhibition of MIF-CD74 Binding by Phenyl Substituted Tetrazole as Depicted Above

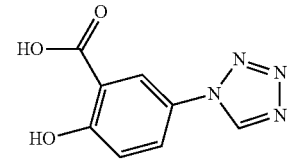

MIF: 15

| Cmpd | % Bound | IC50 |
|---|---|---|
| MIF-015 | | 550 |

TABLE 25

Assay Results for Inhibition of MIF-CD74 Binding and MIF Tautomerase Activity (HPP) by Phenyl Substituted Tetrazole as Depicted Above

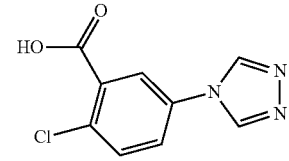

MIF: 16

| Cmpd | IC50 |
|---|---|
| MIF-016 | 250 |

Further details and descriptions of the assays used to generate the data in Tables 1-25 are presented below.

Example 1

MIF-CD74 Binding Assay

Materials and Methods

Coat 96 well plates with 60 μl/well of 26 ng/μl purified, recombinant human MIF receptor (CD74 ectodomain or CD74$^{73-232}$). Incubate at 4° C. overnight. Wash the plate 4 times with 250 μl/well TTBS and add 100 μl/well of superblock (Pierce, Ill.). Incubate at 4° C. overnight. Remove the superblock and add mixture of compound and biotin-labeled recombinant human MIF incubated at 4° C. overnight. (Each compound was pre-incubated at various concentrations with 2 ng/μl 0.2 μM biotin-MIF for 2 hours at room temperature in the dark). After washing the plate 4 times with 250 μl/well TTBS, 60 μl/well of Strepavidin-AP (R&D Systems) was added and incubated for 1 hr at room temperature in the dark. Wells were then washed as before and 60 μl/well of PNPP (Sigma) was added, allowing the color to develop in the dark at room temperature and then read at $OD_{405}$ nm.

Example 2

Inhibition of MIF Tautomerase Activity

Materials and Methods

The "capture" assay used immobilized, recombinant MIF receptor ectodomain and biotinylated recombinant MIF in accordance with Leng, L., et al. (2003), MIF signal transduction initiated by binding to CD74. *J. Exp. Med.* 197, 1467-1476.

HPP Tautomerase Assay Materials and Methods

The HPP assay used was adapted to the microtiter plate format. Human MIF protein was purified according to Bernhagen et al. Biochemistry, 33:14144-14155, 1994. Dilutions of the enzyme were prepared in 50 mM sodium phosphate buffer, 1 mM EDTA, pH 6.5. HPP was obtained from Aldrich. A stock solution of 60 mM HPP in ethanol is prepared and kept for maximally 4 hours on ice. The working solution (600 μM) of the substrate was prepared by diluting an aliquot of the stock solution with 50 mM sodium phosphate buffer, 1 mM EDTA, pH 6.5. UV-transparent microtiter plates (96-well) were obtained from Corning (Cat#3635). Inhibitor and enzyme solutions were pipetted manually using an Eppendorf 12-channel pipette. Addition of substrate to start the reaction was performed with an Igel 96 pipetting station (OpalJena, Jena, Germany), which allows simultaneous addition of fluid to all 96 wells of the plates. Optical density (OD) was determined using a SPECTRAmax 250 reader (Molecular Devices). The reader was operated with the SoftmaxPro 2.6.1 software. Assay: Three wells of the microtiter plates were filled with buffer only, to allow for blanking. Into the test wells were pipetted consecutively: 50 μl inhibitor dilution (or buffer for control), 50 μl enzyme dilution (55 nM; final concentration in assay: 18.3 nM), 50 μ.l freshly diluted substrate working solution (600 μ.M; final concentration: 200 μ.M). The last step was performed using the 96-channel pipetting device. The plate was then immediately (i.e. within a few seconds) transferred manually to the SPECTRAmax 250 reader and the optical density was determined (310 nm). From the data obtained, $IC_{50}$ values were calculated using Excel® and XLfit® software.

Additional Compounds

Compound 67

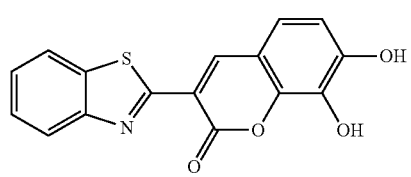

MIF: 9

Compound 68

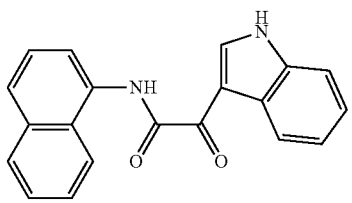

MIF: 14

Compound 69

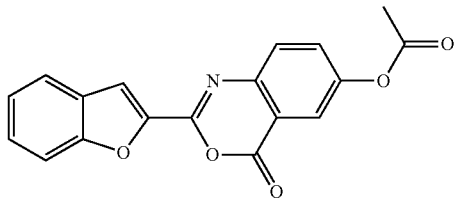

MIF: 17

Compound 70

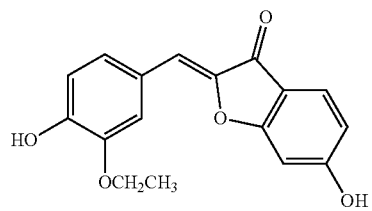

MIF: 19

The terms and expressions that have been employed in this application are used as terms of description and not of limitation, and there is no intent in the use of such terms and expressions to exclude any equivalent of the features shown and described or portions thereof, but it is recognized that various modifications are possible within the scope of the invention as claimed. Thus, it will be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

All references cited herein are hereby incorporated by reference in their entirety.

The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein.

In addition, where features or aspects of the invention are described in terms of Markush groups, those skilled in the art will recognize that the invention is also thereby described in terms of any individual member or subgroup of members of the Markush group.

REFERENCES

Cheng, K. F. & Al-Abed, Y. (2006) Critical modifications of the ISO-1 scaffold improve its potent inhibition of macrophage migration inhibitory factor (MIF) tautomerase activity. *Bioorg. Med. Chem. Lett.* 16, 3376-3379.

Jorgensen, W. L. (2004) The Many Roles of Computation in Drug Discovery. *Science* 303, 1813-1818.

Leng, L.; Metz, C.; Fang, Y.; Xu, J.; Donnelly, S.; Baugh, J.; Delonery, T.; Chen, Y.; Mitchell, R. A. & Bucala, R. (2003) MIF signal transduction initiated by binding to CD74. *J. Exp. Med.* 197, 1467-1476.

Lolis, E. & Bucala, R. (1996) Crystal structure of macrophage migration inhibitory factor (MIF), a glucocorticoid-induced regulator of cytokine production, reveals a unique architecture. *Proc. Assoc. Amer. Physicians* 108, 415-9.

Lolis, E. & Bucala, R. (2003) Macrophage migration inhibitory factor. *Expert Opin. Therap. Targets* 7, 153-164.

Lubetsky, J. B.; Swope, M.; Dealwis, C.; Blake, P. & Lolis, E. (1999) Pro-1 of macrophage migration inhibitory factor functions as a catalytic base in the phenylpyruvate tautomerase activity. *Biochemistry* 38, 7346-54.

Lubetsky, J. B.; Dios, A.; Han, J.; Aljabari, B.; Ruzsicska, B.; Mitchell, R.; Lolis, E. & Al Abed, Y. (2002) The tautomerase active site of macrophage migration inhibitory factor is a potential target for discovery of novel anti-inflammatory agents. *J. Biol. Chem.* 277, 24976-24982.

Morand, E. F.; Leech, M. & Bernhagen, J. (2006) MIF: a new cytokine link between rheumatoid arthritis and atherosclerosis. *Nature Rev. Drug Disc.* 5, 399-411.

Orita, M.; Yamamoto, S.; Katayama, N.; Aoki, M.; Kazuhisa, T.; Yamagiwa, Y.; Seki, N.; Suzuki, H.; Kurihara, H.; Sakashita, H.; Takeuchi, M.; Fujita, S.; Yamada, T. & Tanaka, A. (2001). Coumarin and Chromen-4-one Analogues as Tautomerase Inhibitors of Macrophage Migration Inhibitory Factor: Discovery and X-ray Crystallography. *J. Med. Chem.* 44, 540-547.

Orita, M.; Yamamoto, S.; Katayama, N. & Fujita, S. (2002) Macrophage migration inhibitory factor and the discovery of tautomerase inhibitors. *Curr. Pharm. Res.* 8, 1297-1317.

Pirrung, M. C.; Chen, J.; Rowley, E. G. & McPhail, A. T. (1993) Mechanistic and stereochemical study of phenylpyruvate tautomerase. *J. Am. Chem. Soc.* 115, 7103-10.

Rosengren, E.; Bucala, R.; Aman, P; Jacobsson, L.; Odh, G.; Metz, C. N. & Rorsman, H. (1996) The immunoregulatory mediator macrophage migration inhibitory factor (MIF) catalyzes a tautomerization reaction. *Molec. Med.* 2, 143-149.

Rosengren, E.; Aman, P.; Thelin, S.; Hansson, C.; Ahlfors, S.; Bjork, P.; Jacobsson, L. & Rorsman, H. (1997) The macrophage migration inhibitory factor MIF is a phenylpyruvate tautomerase. *FEBS Lett.* 417, 85-8.

Senter, P. D.; Al-Abed, Y.; Metz, C. N.; Benigni, F.; Mitchell, R. A.; Chesney, J.; Han, J.; Gartner, C. G.; Nelson, S. D.; Todaro, G. J.& Bucala, R. (2002) Inhibition of macrophage migration inhibitory factor (MIF) tautomerase and biological activities by acetaminophen metabolites. *Proc. Nat. Acad. Sci. USA* 99, 144-9.

Stamps, S. L.; Taylor, A. B.; Wang, S. C.; Hackert, M. L. & Whitman, C. P. (2000) Mechanism of the Phenylpyruvate Tautomerase Activity of Macrophage Migration Inhibitory Factor: Properties of the P1G, P1A, Y95F, and N97A Mutants *Biochemistry* 39, 9671-9678.

Sun, H. W.; Bernhagen, J.; Bucala, R. & Lolis, E. (1996) Crystal structure at 2.6-A resolution of human macrophage migration inhibitory factor. *Proc. Nat. Acad. Sci. USA* 93, 5191-5196.

Zhang, X. & Bucala, R. (1999) Inhibition of macrophage migration inhibitory factor (MIF) tautomerase activity by dopachrome analogs. *Bioorg. Med. Chem. Lett.* 9, 3193-3198.

The invention claimed is:

1. A compound according to formula III H:

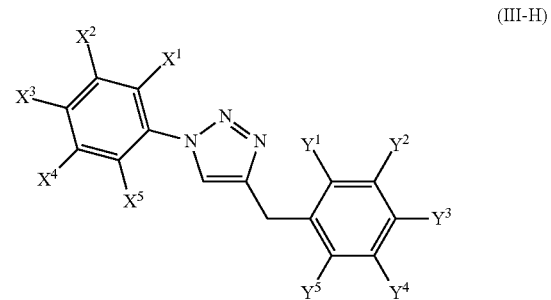

(III-H)

wherein
each $X^1$ is selected from —H, $R^a$; —OH; —$OR^a$; ($C_2$-$C_6$)alkenyl; ($C_2$-$C_6$)alkynyl; halogen; —C≡N; —$NO_2$; —C(=O)$R^b$; —C(=O)$OR^b$; —C(=O)$NR^c_2$; —C(=$NR^b$)$NR^c_2$; —OC(=O)($C_1$-$C_6$)alkyl; —OC(=O)O($C_1$-$C_6$)alkyl; —OC(=O)$NR^c_2$; —$NR^c_2$; —$NR^b$C(=O)$R^b$; —$NR^b$C(=O)O($C_1$-$C_6$)alkyl; —$NR^b$C(=O)$NR^c_2$; —$NR^b$$SO_2$$R^b$; —$SR^b$; —S(O)$R^b$; —$SO_2$$R^b$; —$OSO_2$($C_1$-$C_6$)alkyl; and —$SO_2$$NR^c_2$;

each $X^2$ is selected from —H, —$R^a$; —OH; —$OR^a$; ($C_2$-$C_6$)alkenyl; ($C_2$-$C_6$)alkynyl; halogen; —C≡N; —$NO_2$; —C(=O)$R^b$; —C(=O)$OR^b$; —C(=O)$NR^c_2$; —C(=$NR^b$)$NR^c_2$; —OC(=O)($C_1$-$C_6$)alkyl; —OC(=O)O($C_1$-$C_6$)alkyl; —OC(=O)$NR^c_2$; —$NR^c_2$; —$NR^b$C(=O)$R^b$; —$NR^b$C(=O)O($C_1$-$C_6$)alkyl; —$NR^b$C(=O)$NR^c_2$; —$NR^b$$SO_2$$R^b$; —$SR^b$; —S(O)$R^b$; —$SO_2$$R^b$; —$OSO_2$($C_1$-$C_6$)alkyl; and —$SO_2$$NR^c_2$;

each $X^3$ is —OH or —O($C_1$-$C_6$ alkyl);

each $X^4$ is selected from —H, —$R^a$; —OH; —$OR^a$; ($C_2$-$C_6$)alkenyl; ($C_2$-$C_6$)alkynyl; halogen; —C≡N; —$NO_2$; —C(=O)$R^b$; —C(=O)$OR^b$; —C(=O)$NR^c_2$; —C(=$NR^b$)$NR^c_2$; —OC(=O)($C_1$-$C_6$)alkyl; —OC(=O)O($C_1$-$C_6$)alkyl; —OC(=O)$NR^c_2$; —$NR^c_2$; —$NR^b$C(=O)$R^b$; —$NR^b$C(=O)O($C_1$-$C_6$)alkyl; —$NR^b$C(=O)$NR^c_2$; —$NR^b$$SO_2$$R^b$; —$SR^b$; —S(O)$R^b$; —$SO_2$$R^b$; —$OSO_2$($C_1$-$C_6$)alkyl; and —$SO_2$$NR^c_2$;

each $X^5$ is selected from —H, —$R^a$; —OH; —$OR^a$; ($C_2$-$C_6$)alkenyl; ($C_2$-$C_6$)alkynyl; halogen; —C≡N; —$NO_2$; —C(=O)$R^b$; —C(=O)$OR^b$; —C(=O)$NR^c_2$; —C(=$NR^b$)$NR^c_2$; —OC(=O)($C_1$-$C_6$)alkyl; —OC(=O)O($C_1$-$C_6$)alkyl; —OC(=O)$NR^c_2$; —$NR^c_2$; —$NR^b$C(=O)$R^b$; —$NR^b$C(=O)O($C_1$-$C_6$)alkyl; —$NR^b$C(=O)$NR^c_2$; —$NR^b$$SO_2$$R^b$; —$SR^b$; —S(O)$R^b$; —$SO_2$$R^b$; —$OSO_2$($C_1$-$C_6$)alkyl; and —$SO_2$$NR^c_2$;

each $Y^1$ is selected from —H, —$R^a$; —OH; —$OR^a$; ($C_2$-$C_6$)alkenyl; ($C_2$-$C_6$)alkynyl; halogen; —C≡N; —$NO_2$; —C(=O)$R^b$; —C(=O)$OR^b$; —C(=O)$NR^c_2$; —C(=$NR^b$)$NR^c_2$; —OC(=O)($C_1$-$C_6$)alkyl; —OC(=O)O($C_1$-$C_6$)alkyl; —OC(=O)$NR^c_2$; —$NR^c_2$; —$NR^b$C(=O)$R^b$; —$NR^b$C(=O)O($C_1$-$C_6$)alkyl; —$NR^b$C(=O)$NR^c_2$; —$NR^b$$SO_2$$R^b$; —$SR^b$; —S(O)$R^b$; —$SO_2$$R^b$; —$OSO_2$($C_1$-$C_6$)alkyl; and —$SO_2$$NR^c_2$;

each $Y^2$ is selected from —H, —$R^a$; —OH; —$OR^a$; ($C_2$-$C_6$)alkenyl; ($C_2$-$C_6$)alkynyl; halogen; —C≡N; —$NO_2$; —C(=O)$R^b$; —C(=O)$OR^b$; —C(=O)$NR^c_2$; —C(=$NR^b$)$NR^c_2$; —OC(=O)($C_1$-$C_6$)alkyl; —OC (=O)O($C_1$-$C_6$)alkyl; —OC(=O)NR$^c$$_2$; —NR$^c$$_2$; —NR$^b$C(=O)R$^b$; —NR$^b$C(=O)O($C_1$-$C_6$)alkyl; —NR$^b$C(=O)NR$^c$$_2$; —NR$^b$SO$_2$R$^b$; —SR$^b$; —S(O)R$^b$; —SO$_2$R$^b$; —OSO$_2$($C_1$-$C_6$)alkyl; and —SO$_2$NR$^c$$_2$;

each Y$^3$ is selected from —H, —R$^a$; —OH; —OR$^a$; ($C_2$-$C_6$)alkenyl; ($C_2$-$C_6$)alkynyl; halogen; —C≡N; —NO$_2$; —C(=O)R$^b$; —C(=O)OR$^b$; —C(=O)NR$^c$$_2$; —C(=NR$^b$)NR$^c$$_2$; —OC(=O)($C_1$-$C_6$)alkyl; —OC(=O)O($C_1$-$C_6$)alkyl; —OC(=O)NR$^c$$_2$; —NR$^c$$_2$; —NR$^b$C(=O)R$^b$; —NR$^b$C(=O)O($C_1$-$C_6$)alkyl; —NR$^b$C(=O)NR$^c$$_2$; —NR$^b$SO$_2$R$^b$; —SR$^b$; —S(O)R$^b$; —SO$_2$R$^b$; —OSO$_2$($C_1$-$C_6$)alkyl; and —SO$_2$NR$^c$$_2$;

each Y$^4$ is selected from —H, —R$^a$; —OH; —OR$^a$; ($C_2$-$C_6$)alkenyl; ($C_2$-$C_6$)alkynyl; halogen; —C≡N; —NO$_2$; —C(=O)R$^b$; —C(=O)OR$^b$; —C(=O)NR$^c$$_2$; —C(=NR$^b$)NR$^c$$_2$; —OC(=O)($C_1$-$C_6$)alkyl; —OC(=O)O($C_1$-$C_6$)alkyl; —OC(=O)NR$^c$$_2$; —NR$^c$$_2$; —NR$^b$C(=O)R$^b$; —NR$^b$C(=O)O($C_1$-$C_6$)alkyl; —NR$^b$C(=O)NR$^c$$_2$; —NR$^b$SO$_2$R$^b$; —SR$^b$; —S(O)R$^b$; —SO$_2$R$^b$; —OSO$_2$($C_1$-$C_6$)alkyl; and —SO$_2$NR$^c$$_2$; and each Y$^5$ is selected from —H, —R$^a$; —OH; —OR$^a$; ($C_2$-$C_6$)alkenyl; ($C_2$-$C_6$)alkynyl; halogen; —C≡N; —NO$_2$; —C(=O)R$^b$; —C(=O)OR$^b$; —C(=O)NR$^c$$_2$; —C(=NR$^b$)NR$^c$$_2$; —OC(=O)($C_1$-$C_6$)alkyl; —OC(=O)O($C_1$-$C_6$)alkyl; —OC(=O)NR$^c$$_2$; —NR$^c$$_2$; —NR$^b$C(=O)R$^b$; —NR$^b$C(=O)O($C_1$-$C_6$)alkyl; —NR$^b$C(=O)NR$^c$$_2$; —NR$^b$SO$_2$R$^b$; —SR$^b$; —S(O)R$^b$; —SO$_2$R$^b$; —OSO$_2$($C_1$-$C_6$)alkyl; and —SO$_2$NR$^c$$_2$;

provided that X$^3$ is OH or Y$^3$ is —O($C_1$-$C_6$)alkyl or —OH;

each R$^a$ is independently unsubstituted ($C_1$-$C_6$)alkyl or ($C_1$-$C_6$)alkyl substituted with up to five halogen atoms and up to two substituents selected from the group consisting of —C≡N; —C(=O)R$^b$; —C(=O)OR$^b$; —C(=O)NR$^4$$_2$; —OR$^b$; —OC(=O)($C_1$-$C_6$)alkyl; —OC(=O)O($C_1$-$C_6$)alkyl; —OC(=O)NR$^c$$_2$; —NR$^c$$_2$; —NR$^b$C(=O)R$^b$; —NR$^b$C(=O)NR$^c$$_2$; —S($C_1$-$C_6$)alkyl; —S(O)($C_1$-$C_6$)alkyl; and —SO$_2$($C_1$-$C_6$)alkyl;

each R$^b$ is independently hydrogen or ($C_1$-$C_6$)alkyl;

each R$^c$ is independently hydrogen; ($C_1$-$C_6$)alkyl; —($C_2$-$C_6$)alkylene-OR$^b$; —($C_1$-$C_6$)alkylene-C(=O)OR$^b$; —($C_1$-$C_6$)alkylene-OC(=O)R$^b$; —($C_2$-$C_6$)alkylene-NR$^b$$_2$; —($C_1$-$C_6$)alkylene-C(=O)NR$^c$$_2$; —($C_1$-$C_6$)alkylene-NR$^b$C(=O)R$^b$; —($C_1$-$C_6$)alkylene-NR$^b$C(=O)NR$^b$$_2$; or, optionally, within any occurrence of NR$^c$$_2$, independently of any other occurrence of NR$^c$$_2$, the two R$^c$ groups in combination are —(CH$_2$)$_\alpha$— or —(CH$_2$)$_\beta$Q(CH$_2$)$_2$—;

each α is independently selected from the group consisting of 4, 5, and 6;

each β is independently selected from the group consisting of 2 and 3;

each Q is independently selected from the group consisting of O, S, NR$^b$; NC(=O)R$^b$; NSO$_2$R$^b$; N($C_2$-$C_6$)alkylene-OR$^b$; N($C_1$-$C_6$)alkylene-C(=O)OR$^b$; N($C_1$-$C_6$)alkylene-OC(=O)R$^b$; N($C_2$-$C_6$)alkylene-NR$^b$$_2$; N($C_1$-$C_6$)alkylene-C(=O)NR$^c$$_2$; N($C_1$-$C_6$)alkylene-NR$^b$C(=O)R$^b$; and N($C_1$-$C_6$)alkylene-NR$^b$C(=O)NR$^b$$_2$, or a pharmaceutically acceptable salt, enantiomer, solvate or polymorph thereof.

2. A compound according to formula III-B:

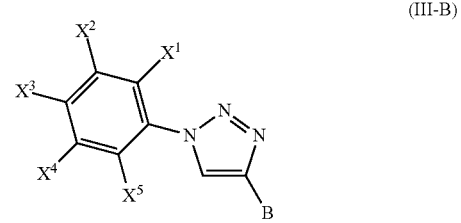

(III-B)

wherein

B is selected from the group consisting of —Ar$^2$ and —CH$_2$Ar$^2$;

Ar$^2$ is an unsubstituted or substituted aromatic ring which is a 5, 6, 8, 9, or 10-membered monocyclic or bicyclic heteroaryl group containing 0, 1, 2, 3 or 4 nitrogen atoms, 0, 1 or 2 oxygen atoms, and 0, 1 or 2 sulfur atoms as heteroatoms;

wherein the optional substituents of Ar$^2$ are each independently selected from —R$^a$; —OH; —OR$^a$; ($C_2$-$C_6$)alkenyl; ($C_2$-$C_6$)alkynyl; halogen; —C≡N; —NO$_2$; —C(=O)R$^b$; —C(=O)OR$^b$; —C(=O)NR$^c$$_2$; —C(=NR$^b$)NR$^c$$_2$; —OC(=O)($C_1$-$C_6$)alkyl; —OC(=O)O($C_1$-$C_6$)alkyl; —OC(=O)NR$^c$$_2$; —NR$^c$$_2$; —NR$^b$C(=O)R$^b$; —NR$^b$C(=O)O($C_1$-$C_6$)alkyl; —NR$^b$C(=O)NR$^c$$_2$; —NR$^b$SO$_2$R$^b$; —SR$^b$; —S(O)R$^b$; —SO$_2$R$^b$; —OSO$_2$($C_1$-$C_6$)alkyl; and —SO$_2$NR$^c$$_2$;

each X$^1$ is selected from —H, —R$^a$; —OH; —OR$^a$; ($C_2$-$C_6$)alkenyl; ($C_2$-$C_6$)alkynyl; halogen; —C≡N; —NO$_2$; —C(=O)R$^b$; —C(=O)OR$^b$; —C(=O)NR$^c$$_2$; —C(=NR$^b$)NR$^c$$_2$; —OC(=O)($C_1$-$C_6$)alkyl; —OC(=O)O($C_1$-$C_6$)alkyl; —OC(=O)NR$^c$$_2$; —NR$^c$$_2$; —NR$^b$C(=O)R$^b$; —NR$^b$C(=O)O($C_1$-$C_6$)alkyl; —NR$^b$C(=O)NR$^c$$_2$; —NR$^b$SO$_2$R$^b$; —SR$^b$; —S(O)R$^b$; —SO$_2$R$^b$; —OSO$_2$($C_1$-$C_6$)alkyl; and —SO$_2$NR$^c$$_2$;

each X$^2$ is selected from —H, —R$^a$; —OH; —OR$^a$; ($C_2$-$C_6$)alkenyl; ($C_2$-$C_6$)alkynyl; halogen; —C≡N; —NO$_2$; —C(=O)R$^b$; —C(=O)OR$^b$; —C(=O)NR$^c$$_2$; —C(=NR$^b$)NR$^c$$_2$; —OC(=O)($C_1$-$C_6$)alkyl; —OC(=O)O($C_1$-$C_6$)alkyl; —OC(=O)NR$^c$$_2$; —NR$^c$$_2$; —NR$^b$C(=O)R$^b$; —NR$^b$C(=O)O($C_1$-$C_6$)alkyl; —NR$^b$C(=O)NR$^c$$_2$; —NR$^b$SO$_2$R$^b$; —SR$^b$; —S(O)R$^b$; —SO$_2$R$^b$; —OSO$_2$($C_1$-$C_6$)alkyl; and —SO$_2$NR$^c$$_2$;

each X$^3$ is —OH or —O($C_1$-$C_6$ alkyl);

each X$^4$ is selected from —H, —R$^a$; —OH; —OR$^a$; ($C_2$-$C_6$)alkenyl; ($C_2$-$C_6$)alkynyl; halogen; —C≡N; —NO$_2$; —C(=O)R$^b$; —C(=O)OR$^b$; —C(=O)NR$^c$$_2$; —C(=NR$^b$)NR$^c$$_2$; —OC(=O)($C_1$-$C_6$)alkyl; —OC(=O)O($C_1$-$C_6$)alkyl; —OC(=O)NR$^c$$_2$; —NR$^c$$_2$; —NR$^b$C(=O)R$^b$; —NR$^b$C(=O)O($C_1$-$C_6$)alkyl; —NR$^b$C(=O)NR$^c$$_2$; —NR$^b$SO$_2$R$^b$; —SR$^b$; —S(O)R$^b$; —SO$_2$R$^b$; —OSO$_2$($C_1$-$C_6$)alkyl; and —SO$_2$NR$^c$$_2$;

each X$^5$ is selected from —H, —R$^a$; —OH; —OR$^a$; ($C_2$-$C_6$)alkenyl; ($C_2$-$C_6$)alkynyl; halogen; —C≡N; —NO$_2$; —C(=O)R$^b$; —C(=O)OR$^b$; —C(=O)NR$^c$$_2$; —C(=NR$^b$)NR$^c$$_2$; —OC(=O)($C_1$-$C_6$)alkyl; —OC(=O)O($C_1$-$C_6$)alkyl; —OC(=O)NR$^c$$_2$; —NR$^c$$_2$; —NR$^b$C(=O)R$^b$; —NR$^b$C(=O)O($C_1$-$C_6$)alkyl; —NR$^b$C(=O)NR$^c$$_2$; —NR$^b$SO$_2$R$^b$; —SR$^b$; —S(O)R$^b$; —SO$_2$R$^b$; —OSO$_2$($C_1$-$C_6$)alkyl; and —SO$_2$NR$^c$$_2$;

each R$^a$ is independently unsubstituted ($C_1$-$C_6$)alkyl or ($C_1$-$C_6$)alkyl substituted with up to five halogen atoms and up to two substituents selected from the group consisting of —C≡N; —C(=O)R$^b$; —C(=O)OR$^b$; —C(=O)NR$^4$$_2$; —OR$^b$; —OC(=O)(C$_1$-C$_6$)alkyl; —OC(=O)O(C$_1$-C$_6$)alkyl; —OC(=O)NR$^c$$_2$; —NR$^c$$_2$; —NR$^b$C(=O)R$^b$; —NR$^b$C(=O)NR$^c$$_2$; —S(C$_1$-C$_6$)alkyl; —S(O)(C$_1$-C$_6$)alkyl; and —SO$_2$(C$_1$-C$_6$)alkyl;

each R$^b$ is independently hydrogen or (C$_1$-C$_6$)alkyl;

each R$^c$ is independently hydrogen; (C$_1$-C$_6$)alkyl; —(C$_2$-C$_6$)alkylene-OR$^b$; —(C$_1$-C$_6$)alkylene-C(=O)OR$^b$; —(C$_1$-C$_6$)alkylene-OC(=O)R$^b$; —(C$_2$-C$_6$)alkylene-NR$^b$$_2$; —(C$_1$-C$_6$)alkylene-C(=O)NR$^b$$_2$; —(C$_1$-C$_6$)alkylene-NR$^b$C(=O)R$^b$; —(C$_1$-C$_6$)alkylene-NR$^b$C(=O)NR$^b$$_2$; or, optionally, within any occurrence of NR$^c$$_2$, independently of any other occurrence of NR$^c$$_2$, the two R$^c$ groups in combination are —(CH$_2$)$_\alpha$— or —(CH$_2$)$_\beta$Q(CH$_2$)$_2$—;

each α is independently selected from the group consisting of 4, 5, and 6;

each β is independently selected from the group consisting of 2 and 3; and each Q is independently selected from the group consisting of O, S, NR$^b$;

NC(=O)R$^b$; NSO$_2$R$^b$; N(C$_2$-C$_6$)alkylene-OR$^b$; N(C$_1$-C$_6$)alkylene-C(=O)OR$^b$; N(C$_1$-C$_6$)alkylene-OC(=O)R$^b$; N(C$_2$-C$_6$)alkylene-NR$^b$$_2$; N(C$_1$-C$_6$)alkylene-C(=O)NR$^b$$_2$; N(C$_1$-C$_6$)alkylene-NR$^b$C(=O)R$^b$; and N(C$_1$-C$_6$)alkylene-NR$^b$C(=O)NR$^b$$_2$, or a pharmaceutically acceptable salt, enantiomer, solvate or polymorph thereof.

3. A compound according to claim 2, wherein B is —CH$_2$Ar$^2$.

4. A compound according to claim 2, wherein the optional substituents of Ar$^2$ are independently selected from the group consisting of —(C$_1$-C$_6$)alkyl; —OH; —O(C$_1$-C$_6$)alkyl; (C$_2$-C$_6$)alkenyl; (C$_2$-C$_6$)alkynyl; halogen; —C≡N; —NO$_2$; —C(=O)R$^b$; —C(=O)OR$^b$; —C(=O)NR$^c$$_2$; —C(=NR$^b$)NR$^c$$_2$; —OC(=O)(C$_1$-C$_6$)alkyl; —OC(=O)O(C$_1$-C$_6$)alkyl; —OC(=O)NR$^c$$_2$; —NR$^c$$_2$; —NR$^b$C(=O)R$^b$; —NR$^b$C(=O)O(C$_1$-C$_6$)alkyl; —NR$^b$C(=O)NR$^c$$_2$; —NR$^b$SO$_2$R$^b$; —SR$^b$; —S(O)R$^b$; —SO$_2$R$^b$; —OSO$_2$(C$_1$-C$_6$)alkyl; and —SO$_2$NR$^c$$_2$.

5. A compound according to claim 2, wherein the optional substituents of Ar$^2$ are independently selected from the group consisting of —(C$_1$-C$_6$)alkyl; —OH; —O(C$_1$-C$_6$)alkyl; (C$_2$-C$_6$)alkenyl; (C$_2$-C$_6$)alkynyl; halogen; —C≡N; —NO$_2$; —C(=O)R$^b$; —C(=O)OR$^b$; —C(=O)NR$^c$$_2$; —C(=NR$^b$)NR$^c$$_2$; —OC(=O)(C$_1$-C$_6$)alkyl; —OC(=O)O(C$_1$-C$_6$)alkyl; —OC(=O)NR$^c$$_2$; —NR$^c$$_2$; —NR$^b$C(=O)R$^b$; —NR$^b$C(=O)O(C$_1$-C$_6$)alkyl; —NR$^b$C(=O)NR$^c$$_2$; —NR$^b$SO$_2$R$^b$; —SR$^b$; —S(O)R$^b$; —SO$_2$R$^b$; —OSO$_2$(C$_1$-C$_6$)alkyl; and —SO$_2$NR$^c$$_2$.

6. A compound according to claim 2, wherein the optional substituents of Ar$^2$ are independently selected from the group consisting of —(C$_1$-C$_6$)alkyl; —OH and —O(C$_1$-C$_6$)alkyl, —C(O)O(C$_1$-C$_6$)alkyl and —C(O)OH.

7. A compound according to claim 2, wherein the optional substituents of Ar$^2$ are independently selected from the group consisting of CH$_3$, CH$_2$CH$_3$, CHCH$_2$, C≡CH, NH$_2$, NHCH$_3$, N(CH$_3$)$_2$, OH, OCH$_3$, SH, SCH$_3$, F, Cl, Br and I.

8. A compound according to claim 1, wherein each one of X$^1$, X$^2$, X$^4$, X$^5$, Y$^1$, Y$^2$, Y$^3$, Y$^4$ and Y$^5$ is independently selected from the group consisting of —H, —(C$_1$-C$_6$)alkyl; —OH; —O(C$_1$-C$_6$)alkyl; (C$_2$-C$_6$)alkenyl; (C$_2$-C$_6$)alkynyl; halogen; —C≡N; —NO$_2$; —C(=O)R$^b$; —C(=O)OR$^b$; —C(=O)NR$^c$$_2$; —C(=NR$^b$)NR$^c$$_2$; —OC(=O)(C$_1$-C$_6$)alkyl; —OC(=O)O(C$_1$-C$_6$)alkyl; —OC(=O)NR$^c$$_2$; —NR$^c$$_2$; —NR$^b$C(=O)R$^b$; —NR$^b$C(=O)O(C$_1$-C$_6$)alkyl; —NR$^b$C(=O)NR$^c$$_2$; —NR$^b$SO$_2$R$^b$; —SR$^b$; —S(O)R$^b$; —SO$_2$R$^b$; —OSO$_2$(C$_1$-C$_6$)alkyl; and —SO$_2$NR$^c$$_2$.

9. A compound according to claim 1, wherein each one of X$^1$, X$^2$, X$^4$, X$^5$, Y$^1$, Y$^2$, Y$^3$, Y$^4$ and Y$^5$ is independently selected from the group consisting of —H, —(C$_1$-C$_6$)alkyl; —OH and —O(C$_1$-C$_6$)alkyl, —C(O)O(C$_1$-C$_6$)alkyl and —C(O)OH.

10. A compound according to claim 1, wherein each one of X$^1$, X$^2$, X$^4$, X$^5$, Y$^1$, Y$^2$, Y$^3$, Y$^4$ and Y$^5$ is independently selected from the group consisting of H, CH$_3$, CH$_2$CH$_3$, CHCH$_2$, C≡CH, NH$_2$, NHCH$_3$, N(CH$_3$)$_2$, OH, OCH$_3$, SH, SCH$_3$, F, Cl, Br and I.

11. A compound according to claim 1, wherein X$^3$ is —OH.

12. A compound according to claim 1, wherein X % X$^2$, X$^4$ and X$^5$ are H.

13. A compound according to claim 1, wherein Y$^3$ is —O(C$_1$-C$_6$)alkyl or —OH.

14. A compound according to claim 1, wherein Y$^3$ is —OH.

15. A compound according to claim 1, wherein Y$^2$, Y$^4$ and Y$^5$ are H.

16. A compound according to claim 2, wherein B is —Ar$^2$.

17. A compound according to claim 11, wherein X$^1$, X$^2$, X$^4$ and X$^5$ are H.

18. A compound according to claim 13, wherein Y$^1$, Y$^2$, Y$^4$ and Y$^5$ are H.

19. A compound according to claim 14, wherein Y$^1$, Y$^2$, Y$^4$ and Y$^5$ are H.

20. A pharmaceutical composition in dosage form comprising an effective amount of at least one compound or pharmaceutically acceptable salt thereof according to claim 1 in combination with a pharmaceutically acceptable carrier, additive or excipient.

21. A pharmaceutical composition in dosage form comprising an effective amount of at least one compound or pharmaceutically acceptable salt thereof according to claim 2 in combination with a pharmaceutically acceptable carrier, additive or excipient.

22. A compound according to claim 16, wherein Ar$^2$ is an unsubstituted or substituted aromatic ring which is a 5- or 6-membered monocyclic heteroaryl group.

23. A compound according to claim 16, wherein Ar$^2$ is an unsubstituted or substituted aromatic ring which is an 8, 9, or 10-membered bicyclic heteroaryl group.

24. A compound according to claim 2, wherein:

the optional substituents of Ar$^2$ are independently selected from the group consisting of —(C$_1$-C$_6$)alkyl; —OH and —O(C$_1$-C$_6$)alkyl, —C(O)O(C$_1$-C$_6$)alkyl and —C(O)OH; and each one of X$^1$, X$^2$, X$^4$, and X$^5$ and is independently selected from the group consisting of —H, —(C$_1$-C$_6$)alkyl; —OH and —O(C$_1$-C$_6$)alkyl, —C(O)O(C$_1$-C$_6$)alkyl and —C(O)OH.

25. A compound according to claim 24, wherein: X$^1$, X$^2$, X$^4$ and X$^5$ are H.

26. A compound according to claim 2, wherein:

the optional substituents of Ar$^2$ are independently selected from the group consisting of CH$_3$, CH$_2$CH$_3$, CHCH$_2$, C≡CH, NH$_2$, NHCH$_3$, N(CH$_3$)$_2$, OH, OCH$_3$, SH, SCH$_3$, F, Cl, Br and I; and each one of X$^1$, X$^2$, X$^4$, X$^5$ is independently selected from the group consisting of H, CH$_3$, CH$_2$CH$_3$, CHCH$_2$, C≡CH, NH$_2$, NHCH$_3$, N(CH$_3$)$_2$, OH, OCH$_3$, SH, SCH$_3$, F, Cl, Br and I.

27. A compound according to claim 2, wherein:
$X^1$, $X^2$, $X^4$ and $X^5$ are H.
28. A compound according to claim 1, wherein the compound is of the following formula:
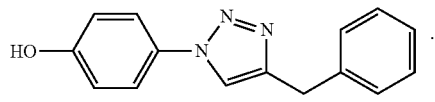
29. A compound of the following formula:
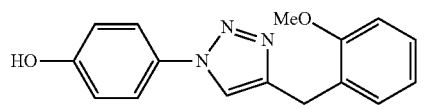 [SMILES: COc1ccccc1Cc1cn(-c2ccc(O)cc2)nn1]
or a pharmaceutically acceptable salt, enantiomer, solvate or polymorph thereof.
* * * * *

UNITED STATES PATENT AND TRADEMARK OFFICE
CERTIFICATE OF CORRECTION

PATENT NO. : 9,540,322 B2  
APPLICATION NO. : 13/100922  
DATED : January 10, 2017  
INVENTOR(S) : Jorgensen et al.

Page 1 of 1

It is certified that error appears in the above-identified patent and that said Letters Patent is hereby corrected as shown below:

In the Specification

In Column 1, Lines 17-21, replace the existing paragraph with the following:
--RESEARCH SUPPORT
This invention was made with government support under AI042310, AR049610, AR050498, and GM032136 awarded by National Institutes of Health. The government has certain rights in the invention.--

Signed and Sealed this
Eleventh Day of May, 2021

Drew Hirshfeld
*Performing the Functions and Duties of the*
*Under Secretary of Commerce for Intellectual Property and*
*Director of the United States Patent and Trademark Office*